(12) United States Patent
Bloom et al.

(10) Patent No.: US 9,943,356 B2
(45) Date of Patent: Apr. 17, 2018

(54) ELECTROSURGICAL DEVICES, ELECTROSURGICAL UNIT AND METHODS OF USE THEREOF

(71) Applicant: Medtronic Advanced Energy LLC, Minneapolis, MN (US)

(72) Inventors: Eliot F. Bloom, Hopkinton, NH (US); Brian M. Conley, South Berwick, ME (US); Jonathan J. Barry, Stratham, NH (US); Roger D. Greeley, Portsmouth, NH (US); Steven G. Miller, Milton, NH (US); Chad M. Greenlaw, Somersworth, NH (US)

(73) Assignee: MEDTRONIC ADVANCED ENERGY LLC, Minneapolis, MN (US)

( * ) Notice: Subject to any disclaimer, the term of this patent is extended or adjusted under 35 U.S.C. 154(b) by 403 days.

(21) Appl. No.: 14/593,312

(22) Filed: Jan. 9, 2015

(65) Prior Publication Data

US 2015/0157386 A1    Jun. 11, 2015

Related U.S. Application Data

(62) Division of application No. 13/006,940, filed on Jan. 14, 2011, now Pat. No. 9,050,113.

(Continued)

(51) Int. Cl.
*A61B 18/14*  (2006.01)
*A61B 18/12*  (2006.01)
(Continued)

(52) U.S. Cl.
CPC ...... *A61B 18/1206* (2013.01); *A61B 17/1671* (2013.01); *A61B 18/14* (2013.01);
(Continued)

(58) Field of Classification Search
CPC . A61B 18/1206; A61B 18/14; A61B 18/1402; A61B 18/082; A61B 2018/1253;
(Continued)

(56) References Cited

U.S. PATENT DOCUMENTS

| 4,074,718 A | 2/1978 | Morrison, Jr. |
| 5,405,269 A | 4/1995 | Stupecky |

(Continued)

FOREIGN PATENT DOCUMENTS

| DE | 20 2007 013012 U1 | 11/2007 |
| DE | 2065985 | 5/2012 |

(Continued)

OTHER PUBLICATIONS

International Search Report and Written Opinion for International Appl. No. PCT/US2011/021389, European Patent Office, The Netherlands, dated Aug. 9, 2011, 18 pages.

*Primary Examiner* — Michael Peffley
(74) *Attorney, Agent, or Firm* — Jeffrey J. Hohenshell

(57) ABSTRACT

An electrosurgical device includes a first electrode spaced alongside a second electrode. The device can be operated as either a bipolar device or a monopolar device and includes a switch to inhibit capacitive coupling to one of the electrodes when the other electrode is used in monopolar fashion.

40 Claims, 49 Drawing Sheets

Related U.S. Application Data

(60) Provisional application No. 61/295,513, filed on Jan. 15, 2010.

(51) Int. Cl.

| | |
|---|---|
| *A61B 17/16* | (2006.01) |
| *A61B 18/08* | (2006.01) |
| *A61B 17/00* | (2006.01) |
| *A61B 18/00* | (2006.01) |

(52) U.S. Cl.
CPC ....... *A61B 17/1664* (2013.01); *A61B 17/1675* (2013.01); *A61B 17/1684* (2013.01); *A61B 18/082* (2013.01); *A61B 18/1402* (2013.01); *A61B 2017/00261* (2013.01); *A61B 2018/0094* (2013.01); *A61B 2018/00178* (2013.01); *A61B 2018/00928* (2013.01); *A61B 2018/00958* (2013.01); *A61B 2018/00988* (2013.01); *A61B 2018/126* (2013.01); *A61B 2018/1253* (2013.01); *A61B 2018/1412* (2013.01); *A61B 2018/1415* (2013.01); *A61B 2018/1472* (2013.01); *A61B 2218/002* (2013.01)

(58) Field of Classification Search
CPC .. A61B 2018/0094; A61B 2018/00958; A61B 2018/00928; A61B 2018/1412; A61B 2018/126; A61B 2018/00178; A61B 2018/00988; A61B 2018/1472
See application file for complete search history.

(56) References Cited

U.S. PATENT DOCUMENTS

| | | | |
|---|---|---|---|
| 5,472,442 A * | 12/1995 | Klicek | A61B 18/1482 606/34 |
| 5,496,312 A | 3/1996 | Klicek | |
| 5,542,916 A | 8/1996 | Hirsch et al. | |
| 5,562,720 A * | 10/1996 | Stern | A61B 18/1206 606/32 |
| 5,599,344 A | 2/1997 | Paterson | |
| 5,620,481 A | 4/1997 | Desai et al. | |
| 6,080,149 A | 6/2000 | Huang et al. | |
| 6,113,596 A * | 9/2000 | Hooven | A61B 18/14 606/42 |
| 6,348,051 B1 | 2/2002 | Farin et al. | |
| 6,402,747 B1 * | 6/2002 | Lindemann | A61B 18/1445 606/37 |
| 6,488,678 B2 | 12/2002 | Sherman | |
| 6,514,248 B1 | 2/2003 | Eggers et al. | |
| 6,673,072 B1 | 1/2004 | Garito et al. | |
| 6,682,527 B2 | 1/2004 | Strul | |
| 6,730,078 B2 | 5/2004 | Simpson et al. | |
| 6,761,716 B2 | 7/2004 | Kadhiresan et al. | |
| 7,250,048 B2 | 7/2007 | Francischelli et al. | |
| 7,344,532 B2 | 3/2008 | Goble et al. | |
| RE40,388 E | 6/2008 | Gines | |
| 7,429,261 B2 | 9/2008 | Kunis et al. | |
| 7,892,230 B2 | 2/2011 | Woloszko | |
| 7,938,825 B2 | 5/2011 | Sturm et al. | |
| 7,942,872 B2 | 5/2011 | Ein-Gal | |
| 7,959,626 B2 | 6/2011 | Hong et al. | |
| 7,993,332 B2 | 8/2011 | Goble et al. | |
| 8,002,769 B2 | 8/2011 | Goble et al. | |
| 8,105,323 B2 | 1/2012 | Buysse et al. | |
| 8,216,233 B2 | 7/2012 | McClurken et al. | |
| 8,235,980 B2 | 8/2012 | Dunning et al. | |
| 8,273,084 B2 | 9/2012 | Kunis et al. | |
| 8,298,225 B2 | 10/2012 | Gilbert | |
| 8,298,226 B2 | 10/2012 | Hosier | |
| 8,303,583 B2 | 11/2012 | Hosier et al. | |
| 8,361,068 B2 | 1/2013 | McClurken | |
| 8,398,627 B2 | 3/2013 | Hosier | |
| 8,430,874 B2 | 4/2013 | Newton et al. | |
| 8,574,187 B2 | 11/2013 | Marion | |
| 8,652,128 B2 | 2/2014 | Ward | |
| 8,747,401 B2 | 6/2014 | Gonzalez et al. | |
| 2001/0020167 A1 | 9/2001 | Woloszko et al. | |
| 2001/0032002 A1 | 10/2001 | McClurken et al. | |
| 2002/0198519 A1 | 12/2002 | Qin et al. | |
| 2003/0130655 A1 | 7/2003 | Woloszko et al. | |
| 2003/0181909 A1 | 9/2003 | Kirwan, Jr. | |
| 2005/0010209 A1 * | 1/2005 | Lee, Jr. | A61B 18/1206 606/41 |
| 2005/0015085 A1 | 1/2005 | McClurken et al. | |
| 2005/0090816 A1 | 4/2005 | McClurken et al. | |
| 2005/0113820 A1 | 5/2005 | Goble et al. | |
| 2006/0084973 A1 * | 4/2006 | Hushka | A61B 18/1445 606/42 |
| 2006/0106375 A1 | 5/2006 | Werneth et al. | |
| 2006/0149225 A1 | 7/2006 | McClurken | |
| 2007/0083193 A1 | 4/2007 | Werneth et al. | |
| 2007/0083195 A1 | 4/2007 | Werneth et al. | |
| 2007/0270795 A1 | 11/2007 | Francischelli et al. | |
| 2008/0015562 A1 | 1/2008 | Hong et al. | |
| 2008/0207028 A1 | 8/2008 | Schutz | |
| 2008/0281312 A1 | 11/2008 | Werneth et al. | |
| 2008/0281322 A1 | 11/2008 | Sherman et al. | |
| 2009/0182325 A1 | 7/2009 | Werneth et al. | |
| 2009/0222001 A1 | 9/2009 | Greeley et al. | |
| 2009/0299365 A1 | 11/2009 | Stewart et al. | |
| 2009/0306655 A1 | 12/2009 | Stangenes et al. | |
| 2011/0130757 A1 | 6/2011 | Horlle et al. | |
| 2011/0178515 A1 | 7/2011 | Bloom et al. | |
| 2011/0190755 A1 | 8/2011 | Mathur et al. | |
| 2011/0230876 A1 | 9/2011 | Hong et al. | |
| 2011/0270120 A1 | 11/2011 | McFarlin et al. | |
| 2011/0270237 A1 | 11/2011 | Werneth et al. | |
| 2012/0136346 A1 | 5/2012 | Condie et al. | |
| 2012/0136348 A1 | 5/2012 | Condie et al. | |
| 2012/0197243 A1 | 8/2012 | Sherman et al. | |
| 2012/0265195 A1 | 10/2012 | Gilbert | |
| 2012/0310241 A1 | 12/2012 | Orszulak | |
| 2012/0316583 A1 | 12/2012 | Horlle et al. | |
| 2013/0006228 A1 | 1/2013 | Johnson et al. | |
| 2013/0006235 A1 | 1/2013 | Podhajsky et al. | |
| 2014/0018795 A1 | 1/2014 | Shiley et al. | |
| 2014/0155888 A1 | 6/2014 | Edwards et al. | |
| 2014/0236142 A1 | 8/2014 | Ward et al. | |
| 2014/0258800 A1 | 9/2014 | Gilbert | |
| 2014/0276750 A1 | 9/2014 | Gilbert | |
| 2014/0276798 A1 * | 9/2014 | Batchelor | A61B 18/1233 606/42 |
| 2014/0276803 A1 | 9/2014 | Hart | |

FOREIGN PATENT DOCUMENTS

| | | |
|---|---|---|
| EP | 1 977 706 | 10/2008 |
| EP | 1 977 706 A1 | 10/2008 |
| EP | 2065985 A3 | 4/2011 |
| WO | WO 1999/34743 | 1/1998 |
| WO | WO 2006/051252 | 5/2006 |
| WO | WO 2012/136956 | 10/2012 |

* cited by examiner

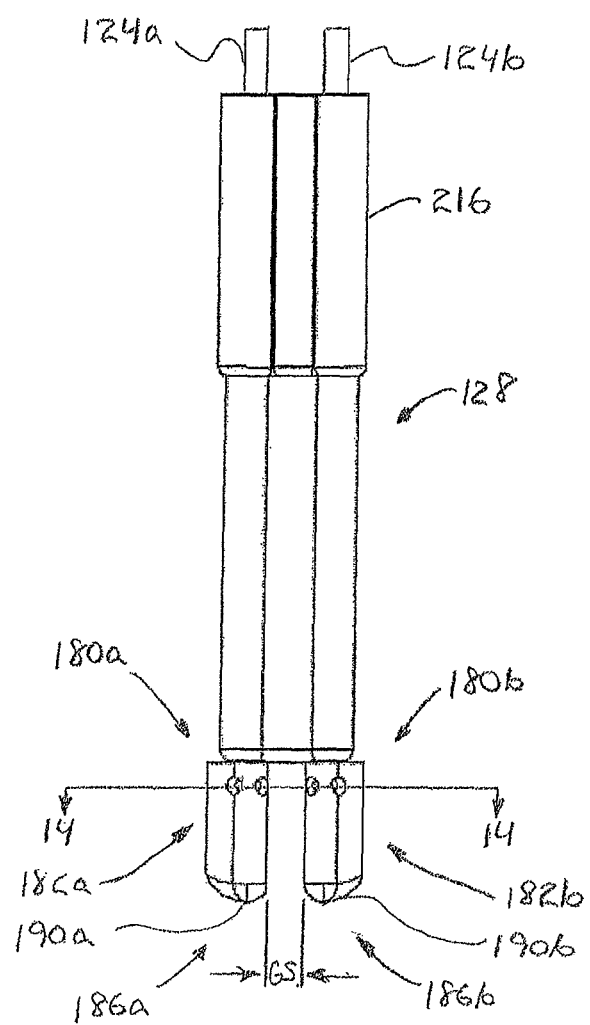

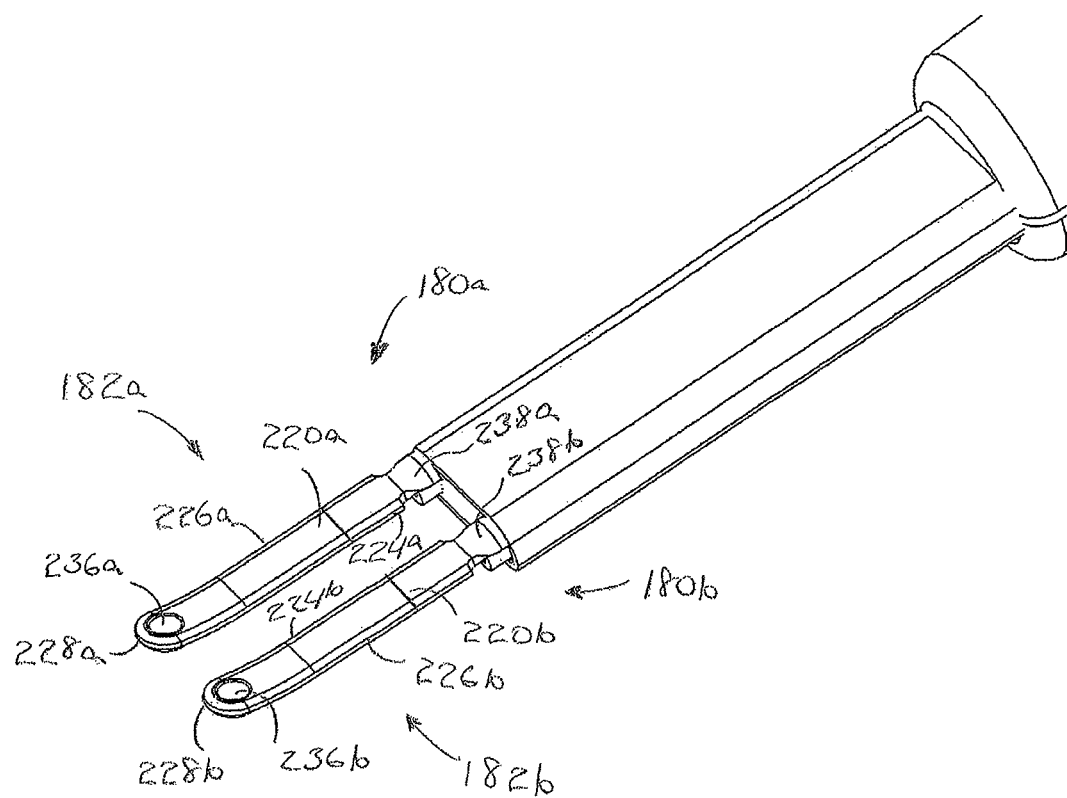

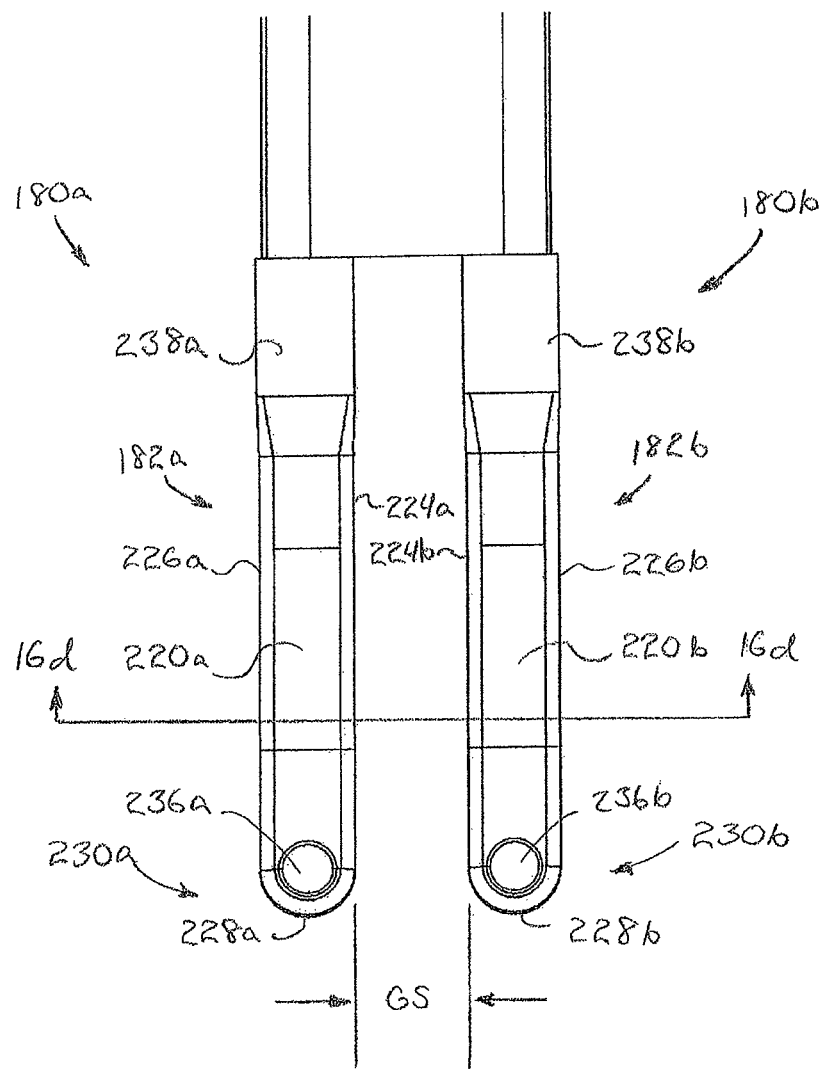

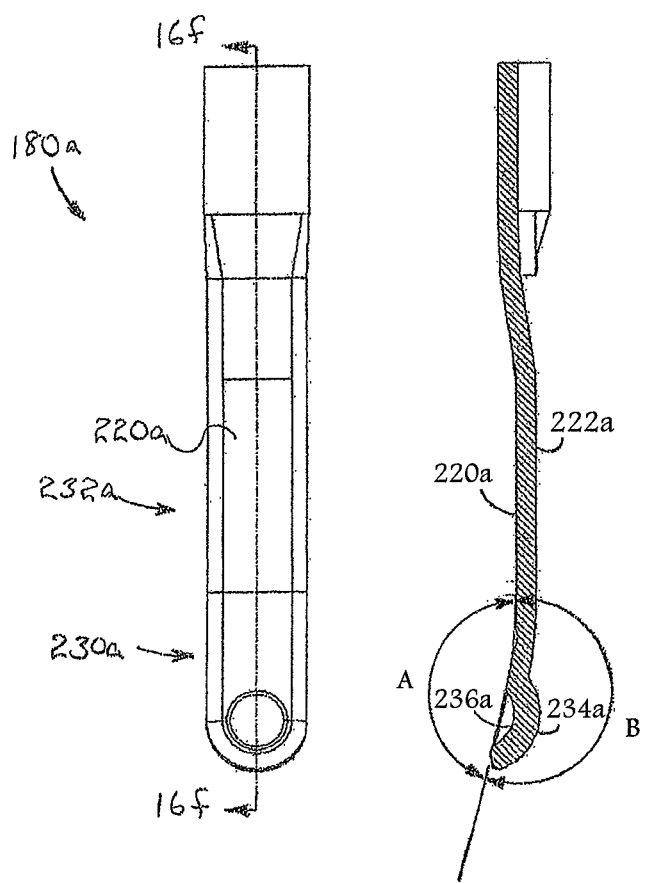

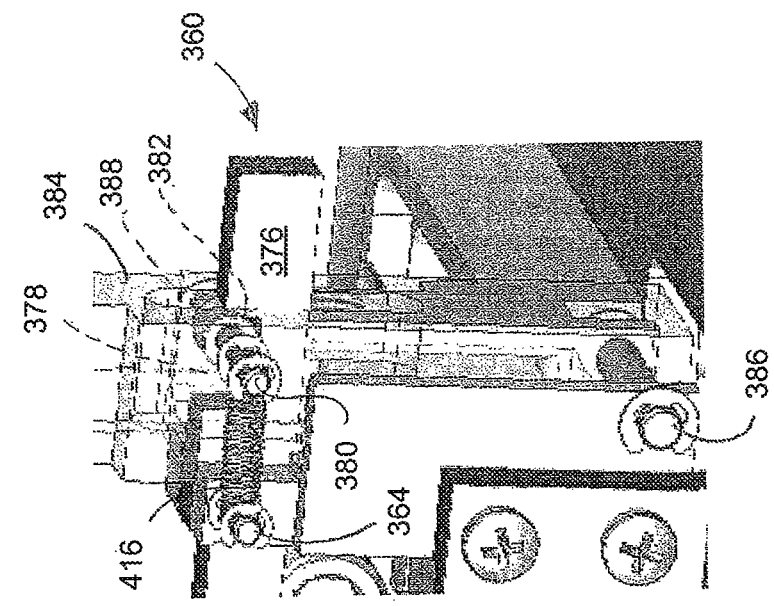
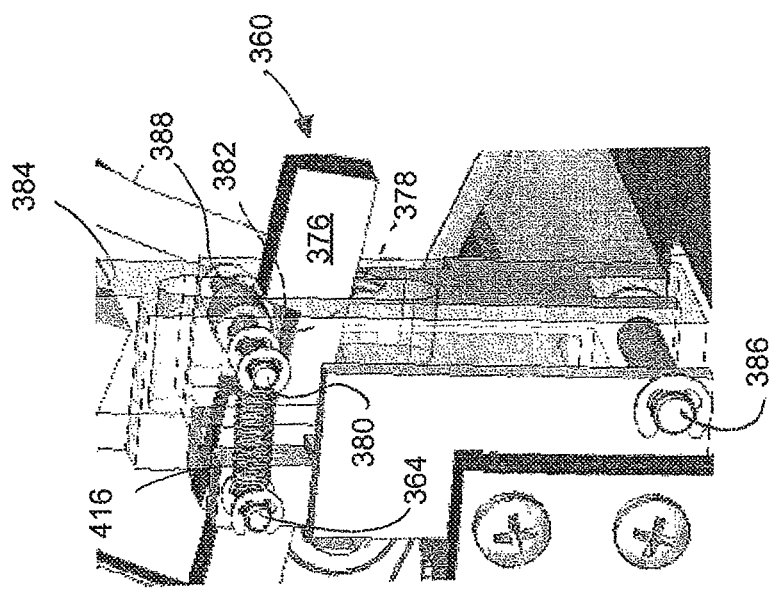

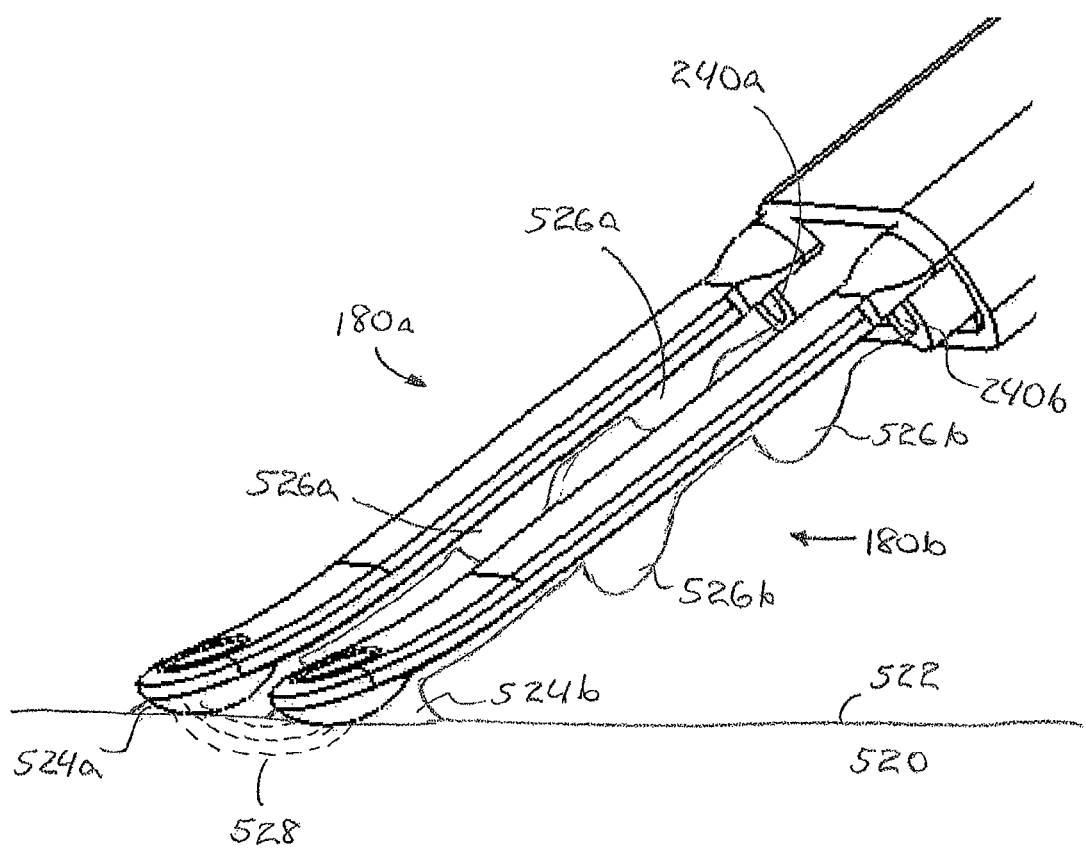

ELECTROSURGICAL DEVICES, ELECTROSURGICAL UNIT AND METHODS OF USE THEREOF

CROSS-REFERENCE TO RELATED APPLICATION

This application is a divisional of patent application Ser. No. 13/006,940, filed Jan. 14, 2011, now U.S. Pat. No. 9,050,113, issued on Jun. 9, 2015, entitled ELECTROSURGICAL DEVICES, ELECTROSURGICAL UNIT AND METHODS OF USE THEREOF, and claims the benefit of U.S. Provisional Patent Application No. 61/295,513, entitled ELECTRO SURGICAL DEVICES, ELECTROSURGICAL UNIT AND METHODS OF USE THEREOF, filed on Jan. 15, 2010, the entireties of which are incorporated herein by reference.

STATEMENT REGARDING FEDERALLY SPONSORED RESEARCH OR DEVELOPMENT n/a

FIELD OF THE INVENTION

This invention relates generally to the field of medical devices, systems and methods for use upon a human body during surgery. More particularly, the invention relates to electro surgical devices, systems and methods that provide for cutting of tissue in addition to coagulation, hemostasis, and sealing of tissue to inhibit blood and other fluid loss during surgery, such as abdominal, orthopedic, head, spine and thoracic surgery as well as general surgery of the body.

BACKGROUND OF THE INVENTION

U.S. Patent Application Publication 2002/0198519 published Dec. 26, 2002 in the name of Qin et al. discloses an integrated device having a radio frequency generator 38, controller 52 with I/O device 54, and a fluid delivery apparatus 44 (e.g., for the delivery of cooling liquid) are integrated within a single housing 400. Electrical connection of a disclosed treatment device 26a126b to the integrated device is performed by connecting an electrical connector 408 of the treatment device 26a126b to electrical connector 402 of the integrated device. Device 26a126b can also be separately connected via tubing 12 to the fluid delivery apparatus 44, to convey processing fluid for discharge by or near an operative element 36a136b.

From Qin et al., since the connection of electrical connector 408 to electrical connector 402 and tubing 12 to fluid delivery apparatus 44 are performed separately as separate steps and not integrated, the time for preparing the system for use may be increased or delayed if one individual is preparing the system, or two individuals may be required to prepare the system if the electrical connection and fluid connection are to be preformed simultaneously.

In addition, as shown in Qin et al., fluid delivery apparatus 44 includes a pump rotor 428. As indicated, the physician can couple the source of cooling liquid to the appropriate port on the handle of the device 26a126b and load the tubing leading from the source of cooling liquid (e.g., a bag containing sterile water) in the pump rotor 428. However, it may be possible to install the tubing improperly, for example, in the wrong direction (i.e. backwards) in such a way that the pump rotor 428 pumps fluid towards the source of cooling liquid rather than device 26a126b. Furthermore, even if the direction of the tubing is proper, it may be possible to misalign the tubing with the pump rotor 428 such that the rotor 428 does not interact properly with the tubing causing a restriction in fluid flow, such as by improperly pinching the tubing, or even damaging the tubing, such as causing a leak. Also, if fluid is introduced into the tubing 12 before the tubing 12 is installed in fluid delivery apparatus 44 it may be possible for the fluid to flow uninhibited through the tubing and leak from treatment device 26a126b. As a result, the foregoing installation errors, set-up and use of the equipment may be further delayed.

In light of the above, what is needed is a structure, method and system in which a medical device to treat tissue can be connected to a power delivery apparatus, such as a radio-frequency generator, and a fluid delivery apparatus, such as a pump, while overcoming the aforementioned deficiencies in the art, and may enable a single individual to connect the device to both of the power delivery apparatus and fluid delivery apparatus substantially simultaneously and without installation error to expedite use thereof.

SUMMARY OF THE INVENTION

In one embodiment, the invention provides source equipment for use with a device to treat tissue, with the source equipment comprising a power delivery apparatus to deliver power provided from a power source to the tissue treatment device and a fluid delivery apparatus to deliver a fluid provided from a fluid source to the tissue treatment device. The power delivery apparatus and the fluid delivery apparatus are arranged to operate with a cartridge member to be placed in a cartridge receptacle of the source equipment.

The source equipment may comprise an electrosurgical unit and the tissue treatment device may further comprise an electro surgical device.

The power delivery apparatus may comprise a radio-frequency power delivery apparatus to deliver radio-frequency power from a radio-frequency power source to the electro surgical device. The radio-frequency power source may comprise a radiofrequency generator located in the electro surgical unit.

The fluid delivery apparatus may further comprise a pump, more particularly a peristaltic pump and even more particularly a rotary peristaltic pump. The fluid source may comprise a container containing a fluid, such as a bag containing a liquid. More particularly, the fluid source may comprise an I.V. bag containing normal (physiologic or 0.9%) saline solution.

The source equipment may comprise a releasable engagement mechanism to engage and disengage with the cartridge member, as well as a releasable positioning mechanism to position the cartridge member.

The power delivery apparatus and/or the fluid delivery apparatus may be capable of being in a use position or a non-use position. The power delivery apparatus and/or the fluid delivery apparatus may be movable, such as by mechanical movement, to engage with the cartridge member or disengage from the cartridge member. The power delivery apparatus and/or fluid delivery apparatus may be movable by operation of an actuator (e.g. motor) or manually (e.g. by hand). The power delivery apparatus and fluid delivery apparatus may be simultaneously and/or jointly moveable.

In another embodiment, the invention provides a cartridge assembly to couple a device to treat tissue with source equipment, with the cartridge assembly comprising a cartridge member to be placed in a cartridge receptacle of the source equipment, and the cartridge member to operate with a power delivery apparatus of the source equipment and a fluid delivery apparatus of the source equipment.

The source equipment may comprise an electrosurgical unit and the tissue treatment device may further comprise an electrosurgical device.

The cartridge member may receive a radio-frequency power output from the electro surgical unit, which may comprise bipolar radio-frequency power or monopolar radio-frequency power. The cartridge member may be electrically coupled to one or more electrodes of the electro surgical device to provide the radio-frequency power output to the one or more electrodes.

The cartridge member may receive a control signal from the electrosurgical unit. The control signal may comprise a signal to control a radio-frequency power output of the electro surgical unit. The cartridge member may be electrically coupled to a radiofrequency power activation switch of the electrosurgical device to provide the signal to the radio-frequency power activation switch.

The cartridge member may include electrosurgical device information, and may provide the electro surgical device information to the electrosurgical unit, with the electrosurgical device information in a format which may be readable by the electro surgical unit. The electro surgical device information may be stored on a storage media.

The electro surgical device information may provide at least one operating parameter for a use of the electro surgical device. The electro surgical device information may provide at least one of a radio-frequency power level setting and a fluid flow level setting for a use of the electro surgical device. The electronic device information may also provide a default setting for a use of the electrosurgical device, a time interval for a use of the electro surgical device or at least one identifier unique to the electrosurgical device.

The cartridge member may provide an electrical contact which may be located on a printed circuit board. The electrical contact may be contacted by a pogo (spring loaded) pin of the electro surgical unit.

The cartridge member may provide a storage media. The storage media may comprise an electronic memory, which may further comprise a programmable read only memory.

The cartridge member may provide a fluid delivery passage to operate with the fluid delivery apparatus of the electro surgical unit. A length of the fluid delivery passage may be defined by a segment of tubing, which may be compressed by an operation of the fluid delivery apparatus. The cartridge member may provide a cartridge body, and a length of the fluid delivery passage may be defined by the cartridge body.

The cartridge member may provide a valve, with the valve in fluid communication with a fluid delivery passage. The valve may at least partially close the fluid delivery passage when the fluid delivery apparatus is inactive. The valve may comprise a check valve and more precisely a diaphragm check valve.

In another embodiment, the invention provides a method of providing an electrosurgical system, with the method comprising:

providing an electro surgical unit having a power delivery apparatus and a fluid delivery apparatus, wherein the power delivery apparatus and the fluid delivery apparatus are arranged to operate with a cartridge member to be placed in a cartridge receptacle of the electrosurgical unit; providing the cartridge member; placing the cartridge member in the cartridge receptacle of the electro surgical unit; engaging the cartridge member with the power delivery apparatus of the electro surgical unit; and engaging the cartridge member with the fluid delivery apparatus of the electro surgical unit.

Engaging the cartridge member with the power delivery apparatus of the electro surgical unit may comprise contacting an electrical contact of the cartridge member with an electrical contact of the power delivery apparatus.

Engaging the cartridge member with the fluid delivery apparatus of the electro surgical unit may comprise compressing a fluid delivery tubing segment of the cartridge member with a compression element of the fluid delivery apparatus.

Engaging the cartridge member with the power delivery apparatus of the electro surgical unit may comprise moving the power delivery apparatus from a non-use position to a use position; and engaging the cartridge member with the fluid delivery apparatus of the electro surgical unit may comprise moving the fluid delivery apparatus from a non-use position to a use position. The power delivery apparatus and fluid delivery apparatus may be moved simultaneously and/or jointly.

In another embodiment, the invention provides an electrosurgical device which comprises a first electrode spaced alongside a second electrode, with each electrode comprising a blade shaped member. Each blade shaped member has opposing sides bounded by edges, with the edges comprising a medial edge and a lateral edge. At least one fluid outlet is adjacent each blade shaped member and each fluid outlet in fluid communication with a fluid passage.

Each blade shaped member may have the same size and shape and comprise a sheet metal and/or a stamped metal strip. Each blade member may have a length in a range of and any increment between 6 mm to 15 mm, a width in a range of and any increment between 2 mm to 3 mm, and a thickness in a range of and any increment between 0.25 mm to 0.75 mm.

A distal end of each blade shaped member may be rounded from the medial edge to the lateral edge of the blade shaped member, and the rounded distal end of each blade shaped member may be defined by a radius.

A distal portion of each blade shaped member may be at an obtuse angle relative to a proximal portion of the blade shaped member. Each obtuse angle may have a vertex extending across a width of each blade shaped member, and be in a range of and any increment between 91 degrees to 179 degrees.

A distal portion of each blade shaped member may include a protrusion on at least one side of the blade shaped member. Each protrusion may comprise a convex curvature on one side of the blade shaped member.

A distal portion of each blade shaped member may include a protrusion on at least one side of the blade shaped member. Each protrusion may comprise a convex curvature on one side of the blade shaped member.

A distal portion of each blade shaped member may include a recess on at least one side of the blade shaped member. Each recess may comprise a concave curvature on one side of the blade shaped member.

The first electrode may be distal to a distal end of a first electrically conductive tube and the second electrode may be distal to a distal end of a second electrically conductive tube. The at least one fluid outlet adjacent the first blade shaped member may be located at a distal end of the first electrically conductive tube and the at least one fluid outlet adjacent the second blade shaped member may be located at a distal end of the second electrically conductive tube.

The blade members may be coplanar. At least a portion of one of the opposing sides of the first blade member may be coplanar and/or parallel with at least a portion of one of the opposing sides of the second blade member. At least a portion of each opposing side of the first blade member may be coplanar and/or parallel with a corresponding opposing side of the second blade member.

The first and second electrodes may be configured as bipolar electrodes, and at least one of the electrodes may be configured as a monopolar electrode.

The first and second electrodes may be configured to treat tissue by moving along a tissue surface in a presence of a bipolar power output and a fluid provided simultaneously from the fluid outlets.

In another embodiment, the invention provides an electrosurgical device, comprising a first electrode and a second electrode; a switch to activate and deactivate bipolar power to the first and second electrodes from a radio-frequency generator to be coupled to the device, the switch comprising a double pole, single throw switch, and a switch to activate and deactivate monopolar power to the first electrode from the radiofrequency generator to be coupled to the device, the switch comprising a single pole, single throw switch.

The double pole, single throw switch may form a control circuit with the radio-frequency generator to be coupled to the device, with the circuit to control activation of the bipolar power from the radio-frequency generator when the double pole, single throw switch is in a closed position, and control deactivation of the bipolar power from the radio-frequency generator when the double pole, single throw switch is in an open position.

The double pole, single throw switch may be in series between the second electrode and a bipolar power output of the radio-frequency generator to be coupled to the device.

The double pole, single throw switch may connect the second electrode with a bipolar power output of the radio-frequency generator in a closed position and disconnect the second electrode with the bipolar power output of the radio-frequency generator in an open position.

The single pole, single throw switch may form a control circuit with the radio-frequency generator to be coupled to the device, with the circuit to control activation of the monopolar power from the radio-frequency generator when the single pole, single throw switch is in a closed position, and control deactivation of the monopolar power from the radio-frequency generator when the single pole, single throw switch is in an open position.

The switch to activate and deactivate bipolar power and the switch to activate and deactivate monopolar power may be both located on a hand-piece of the device.

In another embodiment, the invention provides an electrosurgical device comprising a first electrode and a second electrode, a switch to activate and deactivate monopolar power to the first electrode of the device from a radio-frequency generator to be coupled to the device, and a switch to inhibit capacitive coupling of the second electrode to the monopolar power.

The switch to activate and deactivate monopolar power to the first electrode of the device from a radio-frequency generator to be coupled to the device may comprise a single pole, single throw switch.

The switch to activate and deactivate monopolar power to the first electrode of the device from a radio-frequency generator to be coupled to the device may form a control circuit with the radio-frequency generator to be coupled to the device, with the circuit to control activation of the monopolar power from the radio-frequency generator when the switch is in a closed position, and control deactivation of the monopolar power from the radio-frequency generator when the switch is in an open position.

The switch to inhibit capacitive coupling of the second electrode to the monopolar power may comprise a double pole, single throw switch.

The switch to inhibit capacitive coupling of the second electrode to the monopolar power may form a control circuit with the radio-frequency generator to be coupled to the device, with the circuit to control activation of bipolar power from the radio-frequency generator when the switch is in a closed position, and control deactivation of the bipolar power from the radio-frequency generator when the switch is in an open position.

The switch to inhibit capacitive coupling of the second electrode to the monopolar power may be in series between the second electrode and a bipolar power output of the radio-frequency generator to be coupled to the device.

The switch to inhibit capacitive coupling of the second electrode to the monopolar power may connect the second electrode with a bipolar power output of the radio-frequency generator in a closed position and disconnect the second electrode with the bipolar power output of the radio-frequency generator in an open position.

The switch to activate and deactivate monopolar power and the switch to inhibit capacitive coupling of the second electrode to the monopolar power may be both located on a hand-piece of the device.

In another embodiment, the invention provides an electro surgical device comprising a first electrode and a second electrode and a switch having a first position to activate monopolar power to the first electrode of the device from a radio-frequency generator to be coupled to the device and to inhibit capacitive coupling of the second electrode to the monopolar power.

The switch may have a second position to deactivate the monopolar power to the first electrode of the device from a radio-frequency generator to be coupled to the device and to connect the second electrode with a bipolar power output of the radio-frequency generator.

In another embodiment, the invention provides a first electrode and a second electrode, each electrode to receive radio frequency power from first and second wire conductors, respectively, and a switch having a first position to activate monopolar power to the first electrode of the device from a radio-frequency generator to be coupled to the device and to disconnect the second electrode from the second conductor.

The switch may have a second position to deactivate the monopolar power to the first electrode of the device from a radio-frequency generator to be coupled to the device and to connect the second electrode to the second conductor.

BRIEF DESCRIPTION OF THE DRAWINGS

The invention may be more completely understood in consideration of the following detailed description of various embodiments of the invention in connection with the accompanying drawings, in which:

FIG. 13 is a close-up view of the shaft assembly of the device;

FIG. 16b is a close-up perspective view of a distal portion of the device of FIG. 16a;

FIG. 16c is a close-up plan view of a distal portion of the device of FIG. 16a;

FIG. 16e is a close-up plan view of an electrode of the device of FIG. 16a;

FIG. 16f is a close-up cross sectional view of the electrode of FIG. 16e taken perpendicular to line 16f-16f of FIG. 16e;

FIG. 16g is another close-up perspective view of the distal portion of the device of FIG. 16a;

FIG. 16h is a close of perspective view of an alternative embodiment of the electrode of FIG. 16a;

FIG. 16i is a close of perspective view of an alternative embodiment of the electrode of FIG. 16a;

FIG. 16j is a close of perspective view of an alternative embodiment of the electrode of FIG. 16a;

FIG. 16k is a close of perspective view of an alternative embodiment of the electrode of FIG. 16a;

FIG. 16l is a close of perspective view of a distal portion of an alternative embodiment of the device of FIG. 16a;

FIG. 27 is a rear perspective view of a locking mechanism with the docking mechanism in the up position;

FIG. 28 is rear perspective view of the locking mechanism of with the docking mechanism in the down position;

FIG. 47 is a close-up view of a distal end portion of the device of FIG. 16a with an exemplary fluid coupling to a tissue surface of tissue.

DETAILED DESCRIPTION OF THE INVENTION

Figure 1:
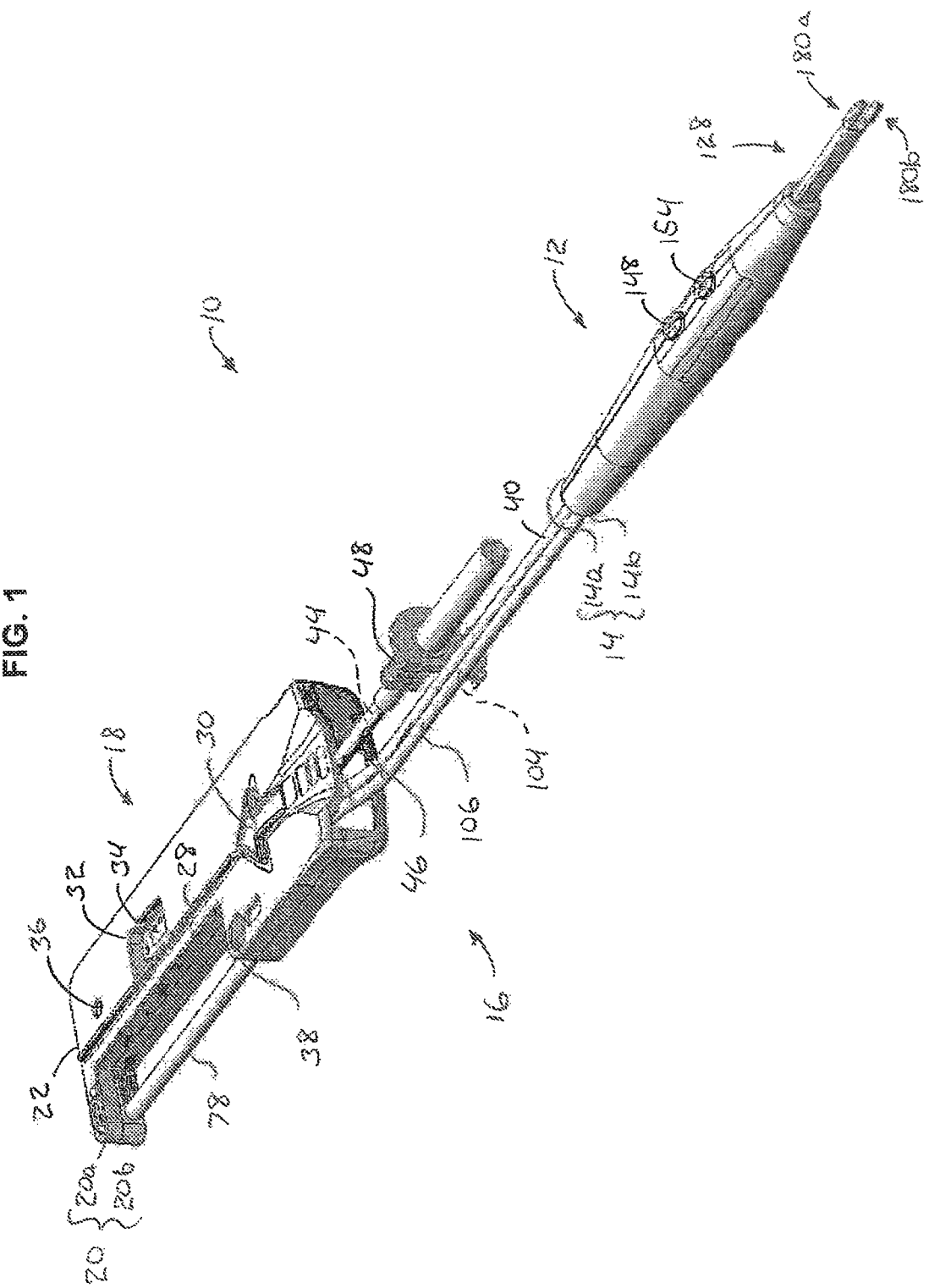
FIG. 1 is a perspective view of an electrosurgical device with a cartridge assembly having a cartridge member to connect a hand-piece to an electrosurgical unit according to one embodiment of the invention.

Throughout the description, like reference numerals and letters indicate corresponding structure as may also be shown in the figures. Also, any particular feature(s) of a particular embodiment may be equally applied to any other embodiment(s) of this specification as suitable. In other words, features between the various embodiments described herein are interchangeable as suitable, and not exclusive. From the specification, it should be clear that any use of the terms "distal" and "proximal" are made in reference from the user of the device, and not the patient.

The inventions disclosed herein provide devices, systems and methods for treating tissue at a tissue treatment site during an electrosurgical procedure. Among other features, the inventions disclosed herein are particularly useful for procedures where it may be desirable to cut tissue, as well as shrink, coagulate and seal tissue against blood and other fluid loss, for example, by shrinking lumens of blood vessels (e.g., arteries, veins).

The invention will now be discussed with reference to the figures, with FIG. 1 showing an exemplary handheld electrosurgical device 10 according to one embodiment of the present invention, which may be used in conjunction with a system of the present invention. Accordingly, it should be understood that the structure of device 10 is not intended to be limiting as to the scope of devices which can be used with the system of the invention.

As shown in FIG. 1, exemplary device 10 comprises an elongated hand-piece 12 having a handle 14 provided by mating handle portions 14a, 14b. Hand-piece 12 may be slender to enable a user of device 10 to hold and manipulate device 10 between the thumb and index finger like a writing instrument such as a pen. Hand-piece 12 may comprise a sterilizable, rigid, electrically insulative material, such as a plastic material. Exemplary plastic materials may comprise polycarbonate (PC) and acrylonitrile-butadiene-styrene (ABS).

Figure 2:
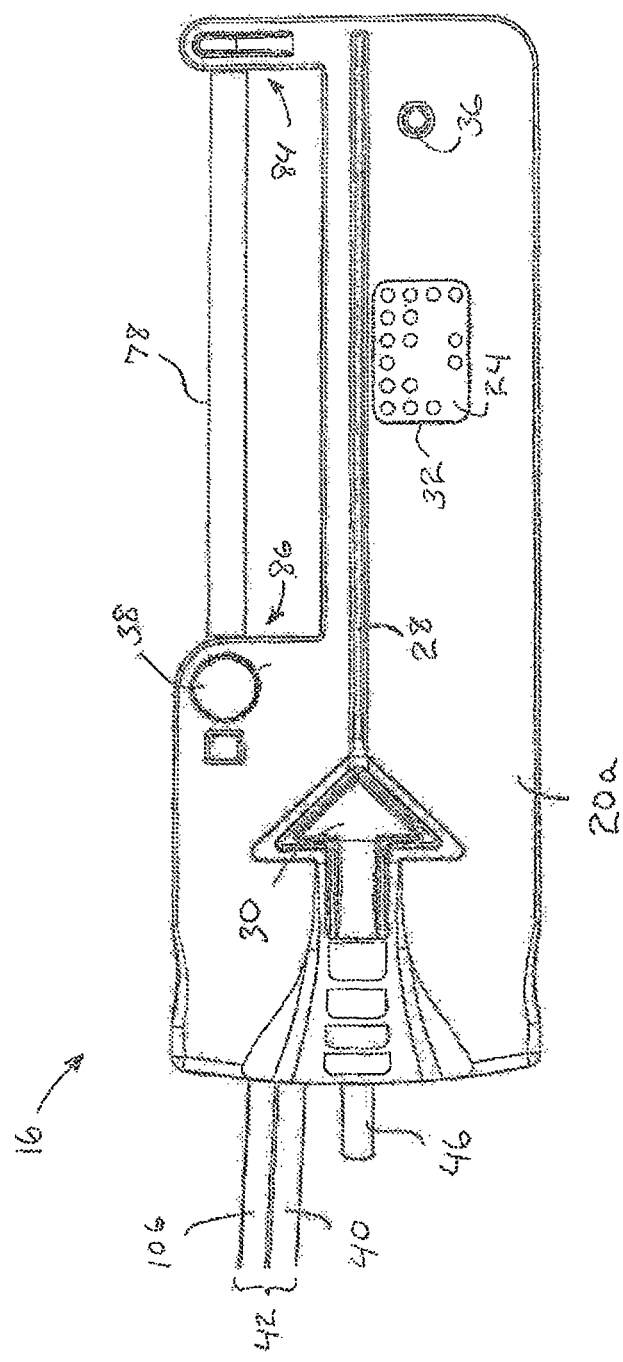
FIG. 2 is a top view of the cartridge member.
Figure 3:
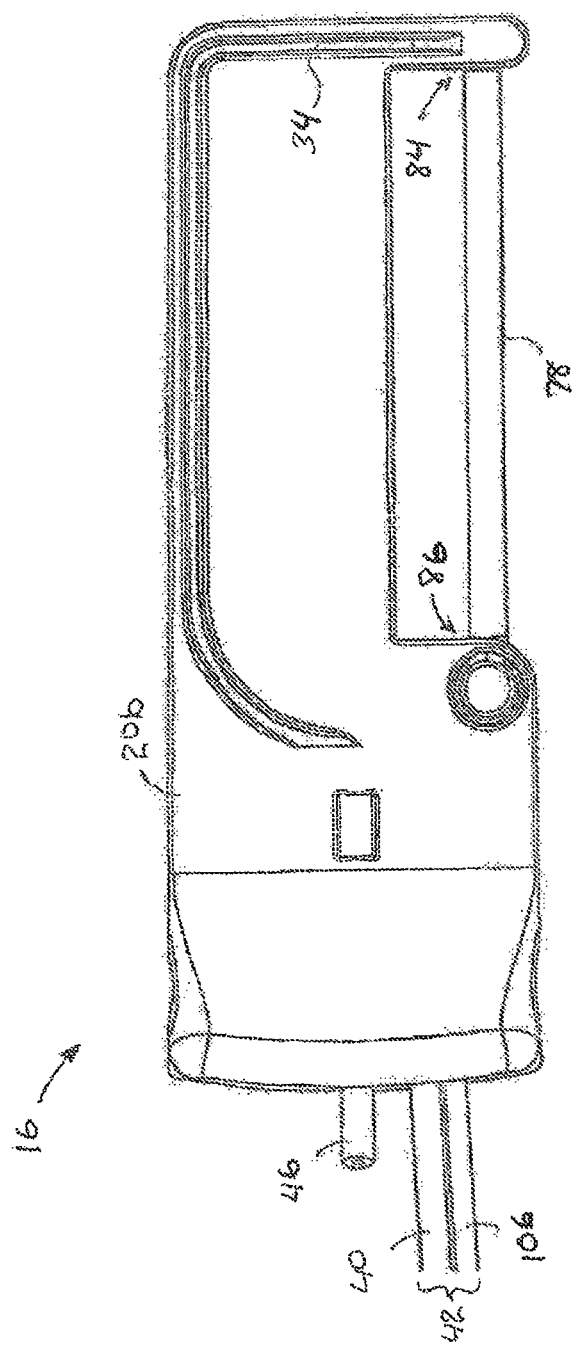
FIG. 3 is a bottom view of the cartridge member.

Device 10 may be coupled to an electro surgical unit 300 (shown in FIG. 17a) by a cartridge assembly 16 comprising cartridge member 18. As shown in FIGS. 2 and 3, cartridge member 18 comprises a substantially planar, elongated, rectangular cartridge body 20 comprising mating cartridge body portions 20a, 20b. To facilitate proper installation of cartridge member 18 with electro surgical device 300, cartridge body 20a may include a directional indicator 30 to show the direction in which cartridge member 18 is to be installed in electrosurgical unit 300, as well as which side of the cartridge member 18 is the top surface. Furthermore, cartridge body 20a includes a protruding element 28, shown in the form of an elongated rib, to physically prevent installation of the cartridge assembly 16 upside down. Cartridge body 20 may be made of a sterilizable, rigid, electrically insulative material, such as a plastic material. Exemplary plastic materials may comprise polycarbonate (PC) and acrylonitrile-butadiene-styrene (ABS).

Figure 37:
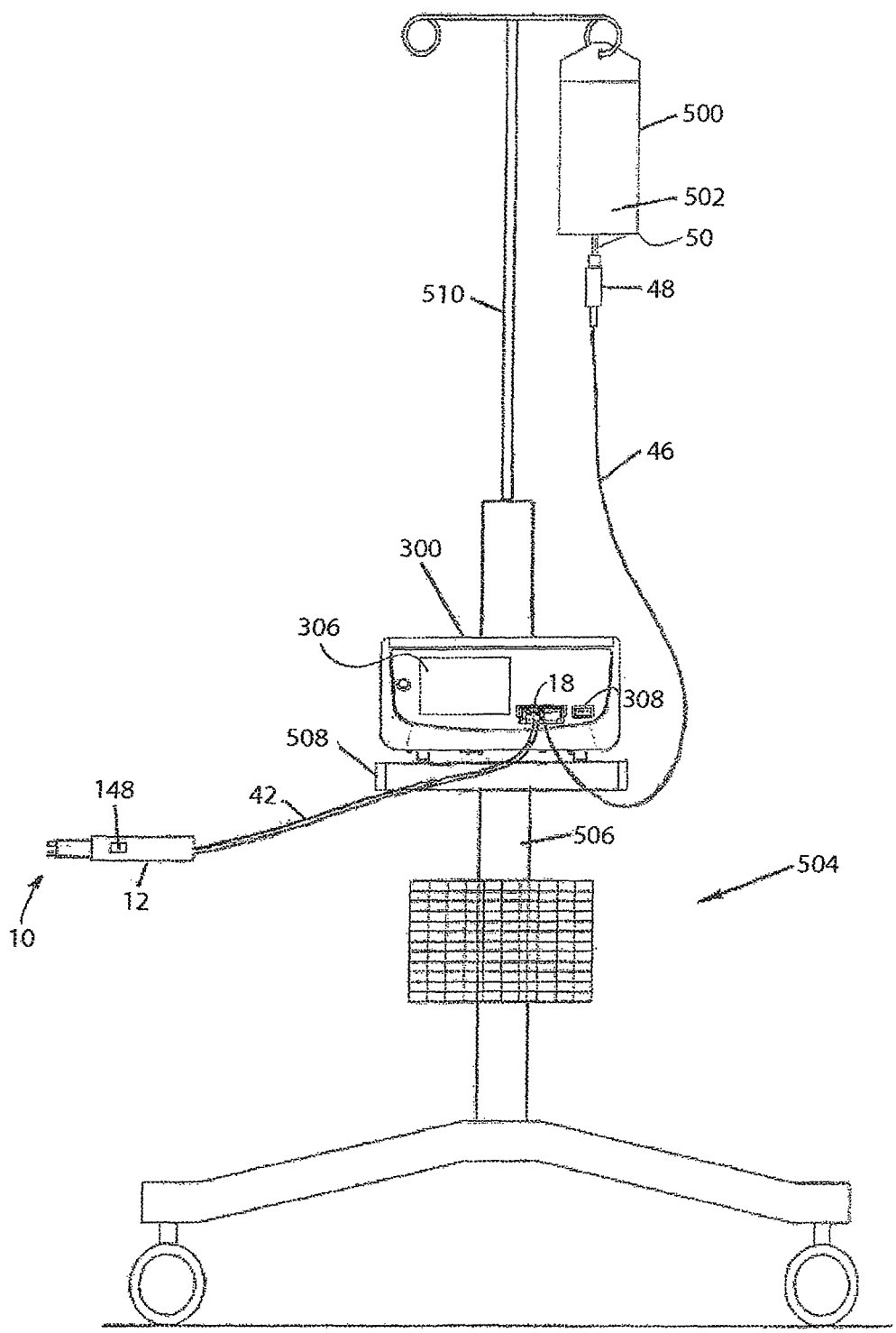
FIG. 37 is a front view of one embodiment of a system of the present invention having electro surgical unit in combination with a fluid source and handheld electro surgical device.

Referring briefly to FIG. 37, when device 10 is connected to other components as part of a system, fluid 502 from a fluid source 500, such as a bag of saline solution, may be communicated through an enclosed fluid passage provided by various structures. Fluid 502 flows from the fluid source 500 into cartridge member 18 of cartridge assembly 16 through lumen 44 of flexible fluid delivery tubing segment 46. At one end, fluid delivery tubing segment 46 preferably couples to fluid source 500 through a drip chamber 48 after the fluid source 500 may be penetrated with a spike 50 located at the end of the drip chamber 48 in a known manner. In other embodiments, drip chamber 48 may be eliminated and tubing segment 46 may be attached directly to a spike 50. Fluid delivery tubing segment 46 may be made of a plastic material, such as flexible polyvinyl chloride (PVC) or other flexible material such as an elastomer.

Figure 4:
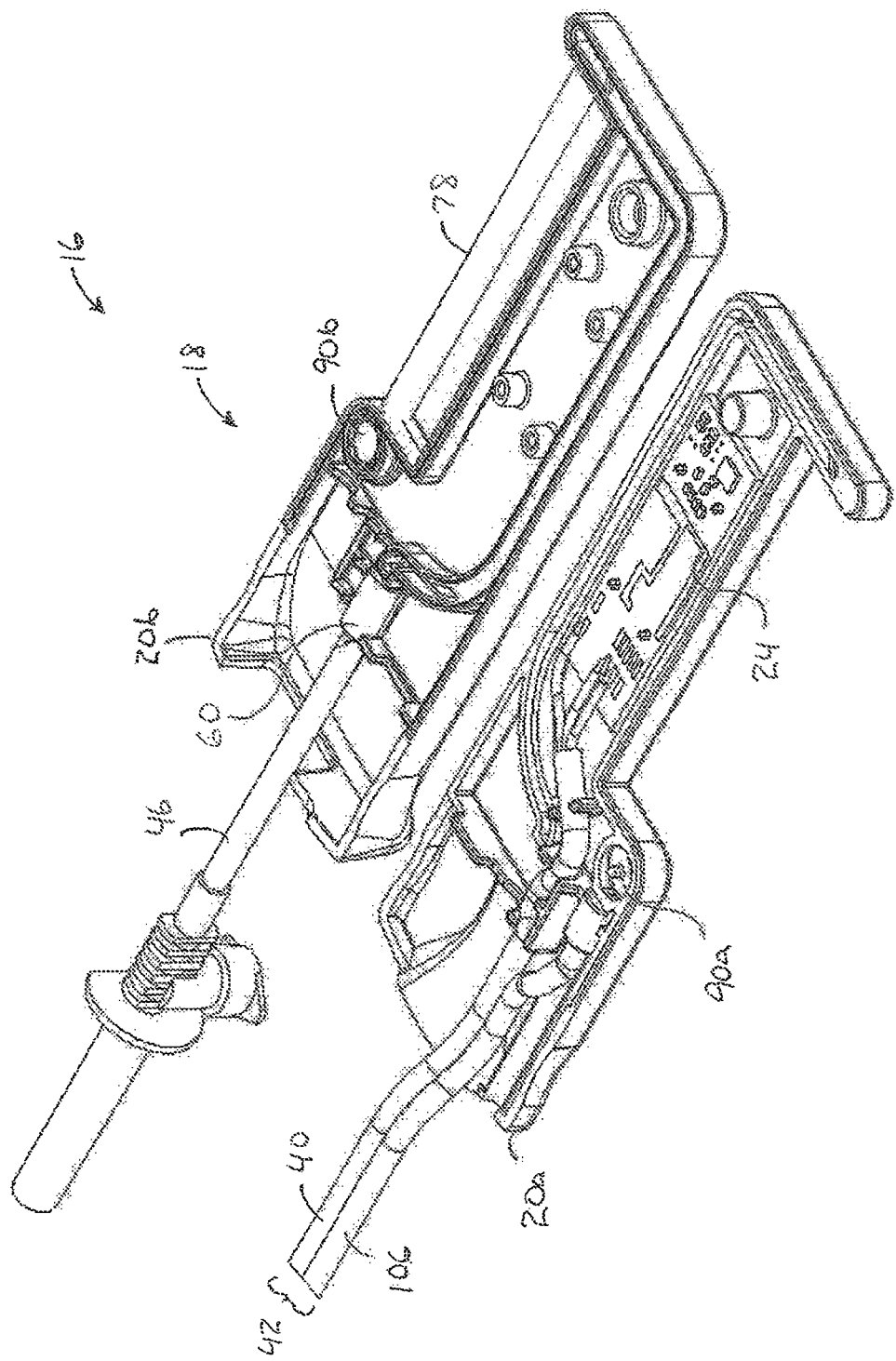
FIG. 4 is a perspective view of the cartridge assembly showing the inner components of the cartridge member.
Figure 5:
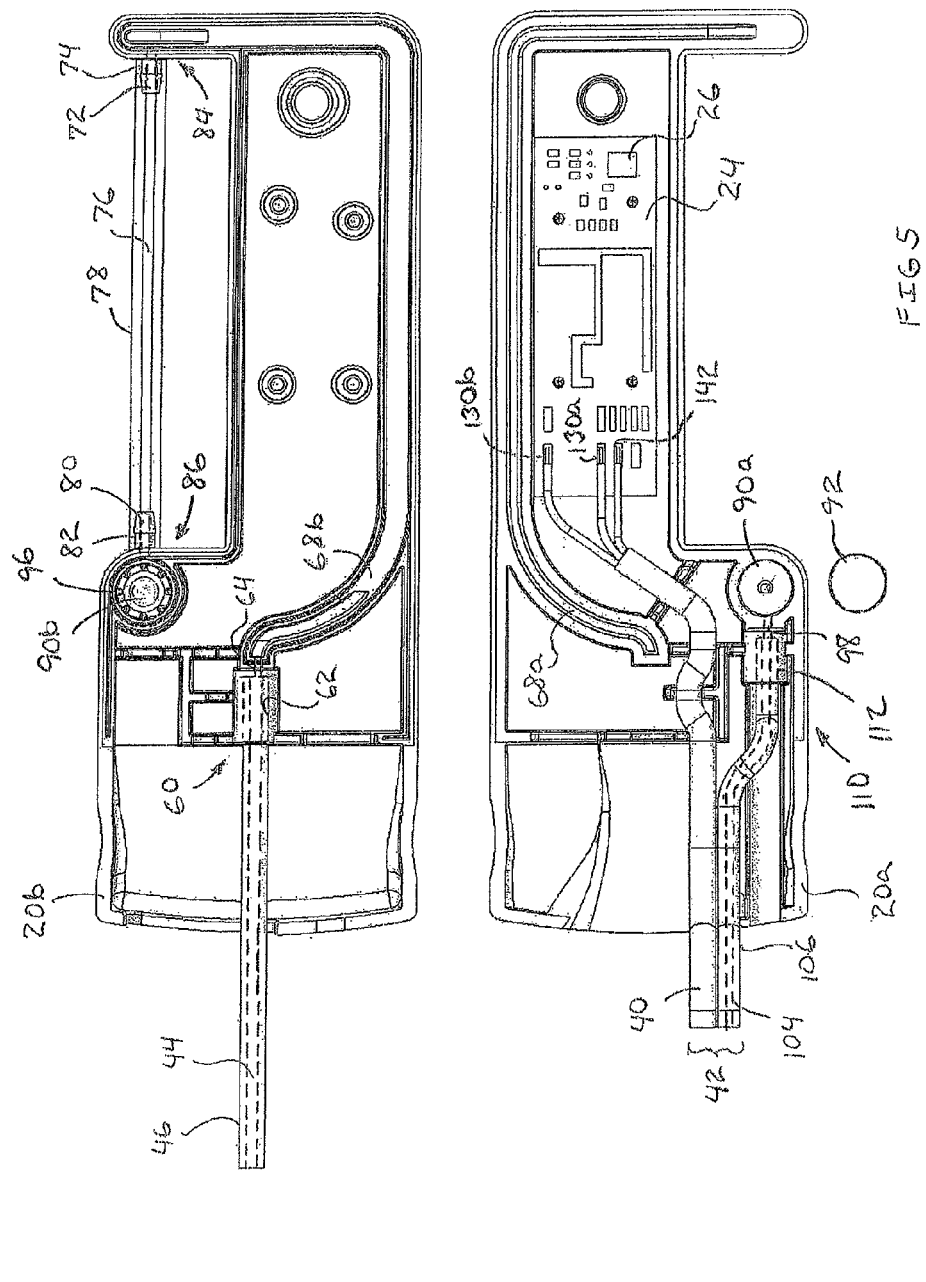
FIG. 5 is a plan view of the cartridge assembly showing the inner components of the cartridge member.

Referring now to FIGS. 4 and 5, at its opposite end, fluid delivery tubing segment 46 may be coupled and tightly fastened with a fluid tight connection to cartridge body 20b of cartridge member 18 via a female connector portion 60. More particularly, fluid delivery tubing segment 46 may be coupled to cartridge body 20b via a distal end portion of the tubing segment 46 extending into a cylindrical cavity 62 formed in cartridge body 20b to provide a cylindrical receptacle. The outer surface of fluid delivery tubing segment 46 may be configured to mate against and form a press (interference) fit seal with corresponding inner surfaces of connector portion 60 to provide a fluid tight seal there between. An adhesive or solvent bonding may be used there between to further strengthen the seal, or in lieu of the press fit.

Continuing with FIG. 5, from lumen 44 of fluid delivery tubing segment 46, the fluid passage extends through a through hole 64 provided at the base of cavity 62 and may be next provided and defined by an elongated enclosed channel 68 formed by overlying portions of cartridge bodies 20a, 20b. More particularly, channel 68 may be formed by mating a channel portion 68a of cartridge body 20a with a channel portion 68b of cartridge body 20b and forming a continuous hermetic seal there between, particularly by vibration, ultrasonic or other plastic welding method.

From channel 68, the fluid passage thereafter extends through a through hole 72 formed in male connector portion 74, into lumen 76 of fluid delivery tubing segment 78 and thereafter through hole 80 formed in male connector portion 82. As shown in FIG. 5, fluid delivery tubing segment 78 may be coupled and tightly fastened with a fluid tight connection to cartridge body 20b of cartridge member 18 via male connector portions 74 and 82 provided by two spaced, parallel, fixed supports 84 and 86 at the opposite ends thereof. More particularly, fluid delivery tubing segment 78 may be coupled to cartridge body 20b via male connector portions 74 and 82 which extend into the lumen 76 of delivery tubing segment 78. The inner surface of lumen 76 of fluid delivery tubing segment 78 may be configured to mate against and form a press (interference) fit seal with corresponding outer surfaces of connector portions 74 and 82 to provide a fluid tight seal there between. An adhesive or solvent bonding may be used there between to further strengthen the seal, or in lieu of the press fit. Similar to fluid delivery tubing segment 46, fluid delivery tubing segment 78 may be made of a plastic material, such as flexible polyvinyl chloride (PVC) or other flexible material such as an elastomer.

It may be possible to replace fluid delivery tubing segment 78 to Increase or decrease the fluid flow output of fluid delivery apparatus 420 (discussed in greater detail below) by changing the size (diameter) of lumen 76 of delivery tubing segment 78. Furthermore, fluid delivery tubing segment 78 may require a thicker cross-section and durability than the other fluid delivery tubing segments, such as fluid delivery tubing segment 46. For example, in a particular embodiment discussed in greater detail below, fluid delivery tubing segment 78 may be configured to be compressed by a fluid delivery apparatus 422 contained within electrosurgical unit 300, to force fluid 502 through the lumen 76 thereof in a known manner. In such instance, the thicker portion of the fluid delivery tubing for device 10 may be limited to fluid delivery tubing segment 78.

Continuing with FIG. 5, from through hole 80 of connector portion 82, the fluid passage extends into a cylindrical chamber 90 of a one-way (check) diaphragm valve 38 (FIG. 1) provided and defined chamber portions 90a and 90b which are separated by a flat disc shaped plastic membrane 92. With valve 38, fluid 502 only may flow in one direction. In use, when valve 38 is open, membrane 92 may be positioned towards the end of chamber portion 90a and fluid may be allowed to pass through chamber 90 and into through hole 98 to exit chamber 90. In order to inhibit back flow of fluid 502, when valve 38 is closed, membrane 92 may be positioned on seat 96 in a cavity of cartridge body 20b, which closes the fluid passage and fluid communication between the exit port provided by through hole 98 and the inlet port provided by through hole 80. Furthermore, membrane 92 inhibits fluid 502 from flowing through valve 38 if the fluid pressure is less than about 3.5 psi. In this manner, fluid 502 may not flow through valve 38 to handpiece 12 in the event fluid 502 is introduced to the fluid passage before cassette member 18 may be installed in electrosurgical unit 300, but rather will only open to permit flow there through when a pressure of greater than 3.5 is provided by fluid delivery apparatus 420 after cartridge member 18 has been installed in electro surgical unit 300.

From through hole 98, the fluid passage extends into lumen 104 of fluid delivery tubing segment 106. Similar to fluid delivery tubing segment 46, tubing segment 106 may be coupled and tightly fastened with a fluid tight connection to cartridge body 20a of cartridge member 18 via a female connector portion 110. More particularly, fluid delivery tubing segment 106 may be coupled to cartridge body 20a via a distal end portion of the tubing segment 106 extending into a cylindrical cavity 112 formed by cartridge body 20a to provide a cylindrical receptacle. The outer surface of fluid delivery tubing segment 106 may be configured to mate against and form a press (interference) fit seal with corresponding inner surfaces of connector portion 110 to provide a fluid tight seal there between. An adhesive or solvent bonding may be used there between to further strengthen the seal, or in lieu of the press fit. As shown in FIG. 5, tubing segment 106 may be molded and formed unitary with cord 40, such as by plastic co-extrusion, to provide a single cable 42.

Figure 6:
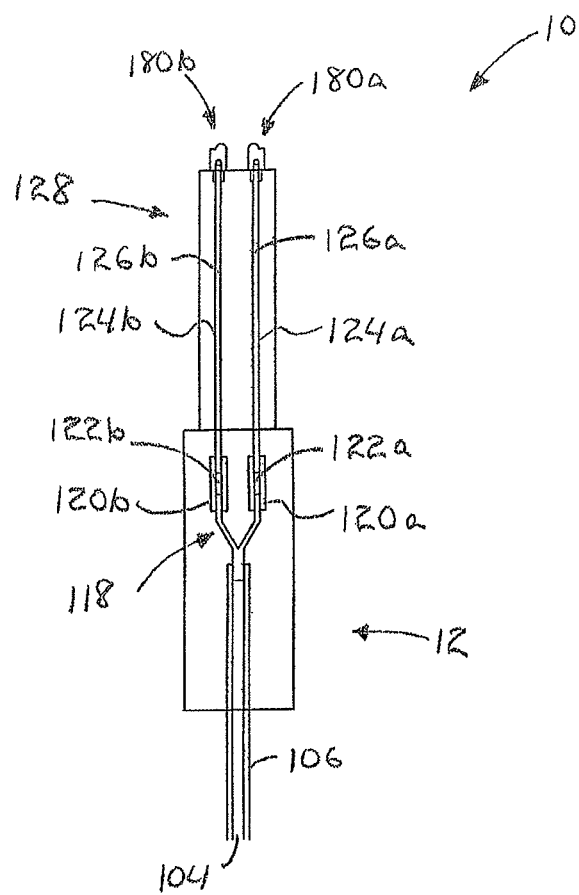
FIG. 6 is a plan view showing certain fluid passages of the electro surgical device.

Referring to FIG. 6, fluid delivery tubing segment 106 enters the proximal end of hand-piece 12 of electro surgical device 10. Within hand-piece 12 of device 10, fluid delivery tubing segment 106 may be connected to the inlet branch of a Y-splitter 118, which thereafter provides two outlet branches which are connected to the proximal ends of fluid delivery tubing segments 120a, 120b. The distal ends of delivery tubing segments 120a, 120b are thereafter connected to the proximal ends of shafts 124a, 124b. To connect fluid delivery tubing segments 120a, 120b to shafts 124a, 124b, the lumens 122a, 122b of the fluid delivery tubing segments 120a, 120b are preferably interference fit over the outside diameter of shafts 124a, 124b to provide an interference fit seal there between. An adhesive or solvent bonding may be used there between to further strengthen the seal, or in lieu of the press fit. Fluid 502 may then flow through the lumens 126a, 126b of shafts 124a, 124b and thereafter exit from device 10 as discussed in greater detail below.

Additionally, device 10 may include an aspiration/suction tubing segment to remove fluid 502 from a tissue treatment site. The suction tubing segment may pass through cartridge member 18 and thereafter be connected to a vacuum source.

In addition to operating in conjunction with a fluid delivery apparatus 422 within electrosurgical unit 300, as discussed in greater detail below, cartridge assembly 16 also operates in conjunction with a radio-frequency power delivery apparatus 440 and other electrical components and circuits within electrosurgical unit 300.

As shown in FIGS. 1 and 2, as well as FIGS. 4 and 5, cartridge member 18 includes a two layer printed circuit board 24, one side of which may be exposed through an aperture 32 in cartridge body 20a of cartridge member 18 to provide an electrical communication with electro surgical unit 300. Printed circuit board 24 may comprise a 0.05-0.07 inch thick base insulator with top and bottom conductive layers deposited thereon. The exposed conductive layers may more particularly comprise 2-6 microns of gold over 100-300 microns of electroless nickel over copper. Detailed drawings of printed circuit board 24 may be found in FIGS. 7-11.

As shown in FIGS. 7-11, printed circuit board 24 includes a plurality of electrical contacts thereon, which may comprise electrical contact pads to electrically couple with corresponding electrical contacts of electro surgical unit 300. Certain of these electrical contacts and their associated function will now be discussed.

Figure 7:
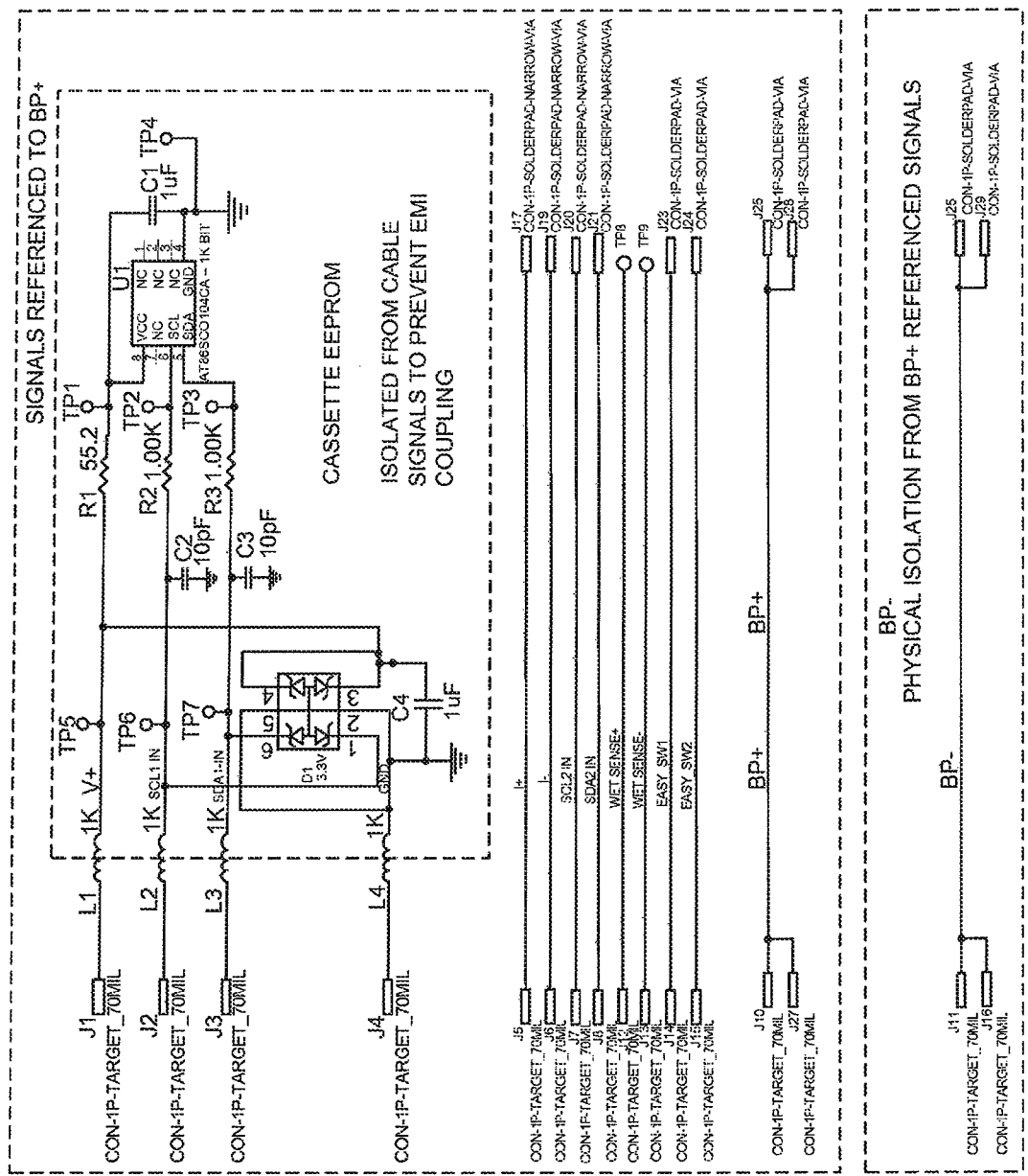
FIG. 7 is a diagram of the various electrical connections of a printed circuit board assembly provided with the cartridge member.
Figure 8:
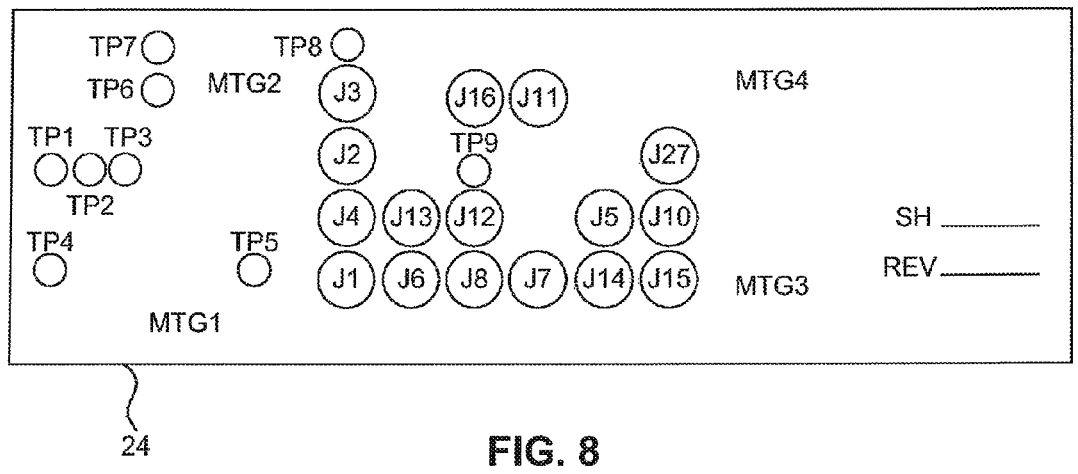
FIG. 8 is a top plan view of the printed circuit board assembly.
Figure 9:
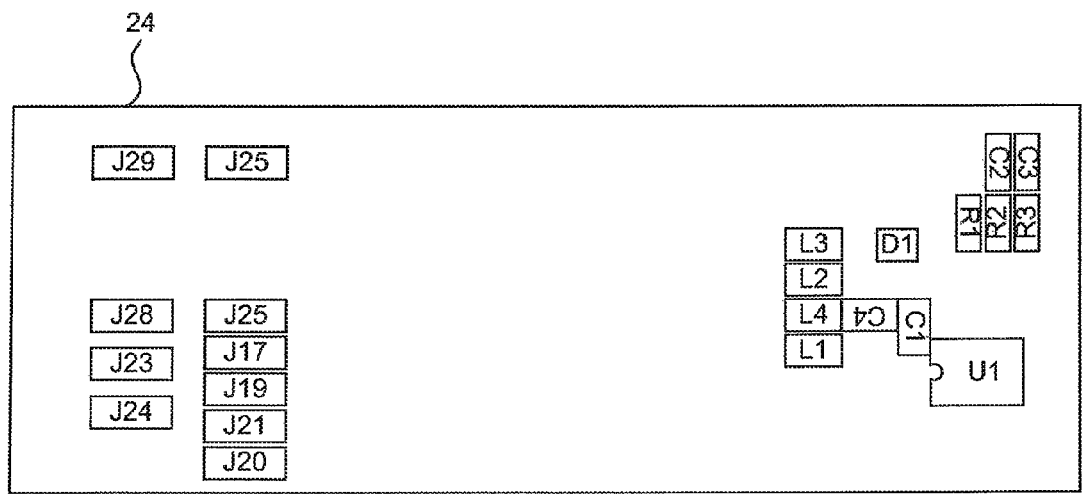
FIG. 9 is a bottom plan view of the printed circuit board assembly.
Figure 10:
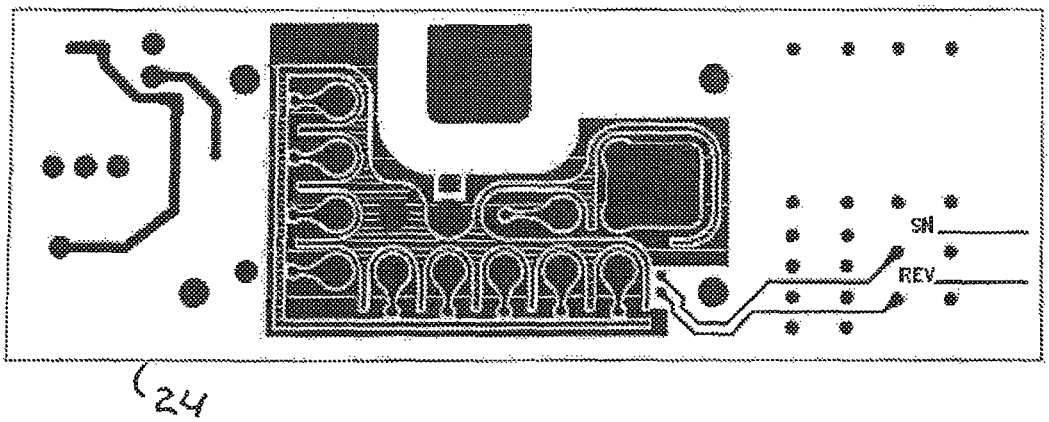
FIG. 10 is a top view of the upper (top) layer of the printed circuit board assembly.
Figure 11:
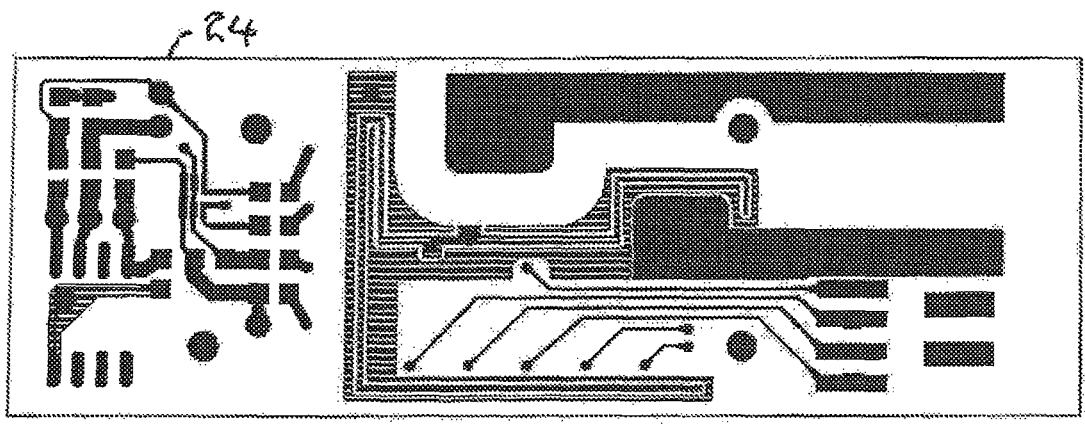
FIG. 11 is a top view of the lower (bottom) layer of the printed circuit board assembly.

Bipolar radio-frequency power from electrosurgical unit 300 may be provided from outputs BP+ and BP-thereof. As shown in FIG. 7, electrical contacts J10/J27 receive power from bipolar power output BP+ which may then communicated along an electrically conductive pathway to electrical contacts J25/J28. Electrical contacts J11/J16 receive power from bipolar power output BP-which may then communicated along an electrically conductive pathway to electrical contacts J26/J29. Electrical contacts J10/J27 and J11/J16 are shown in FIG. 8, while electrical contacts J25/J28 and J26l J29 are shown in FIG. 9.

Figure 12A:
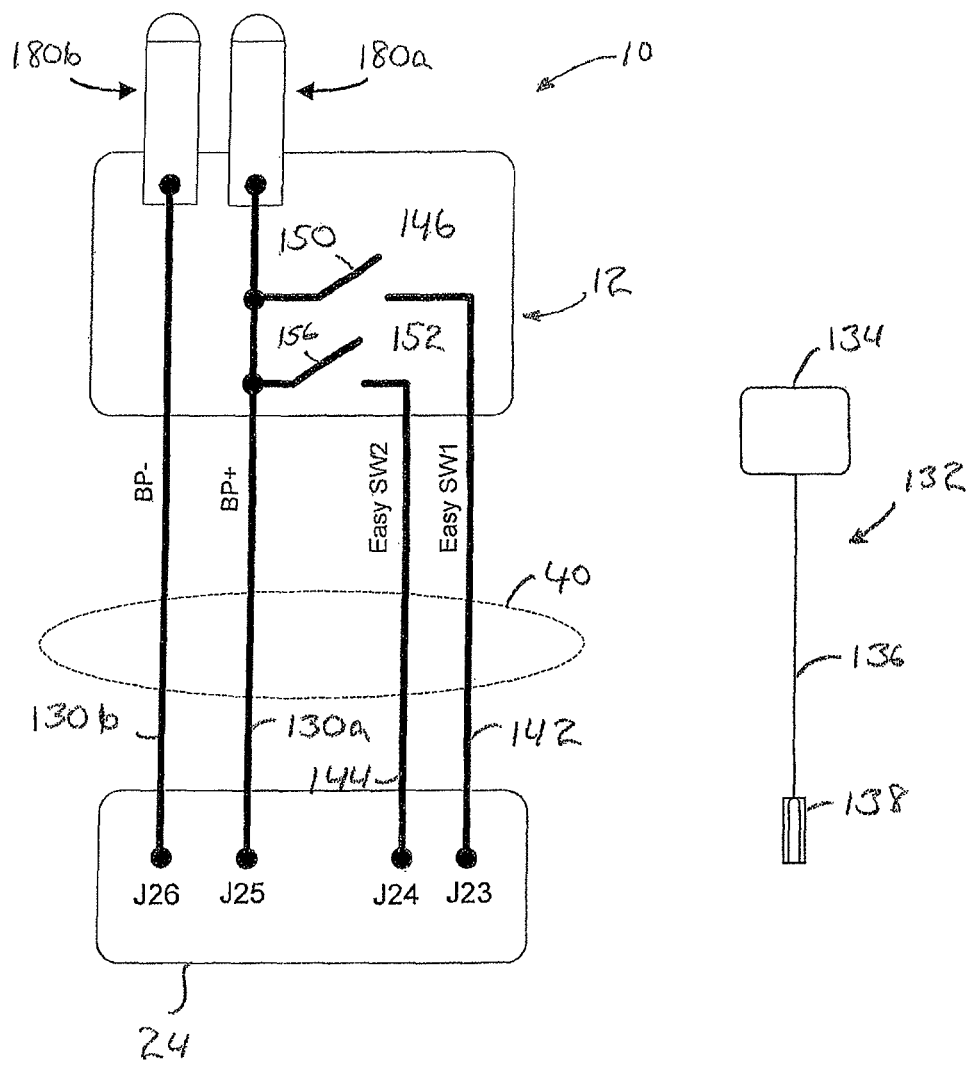
FIG. 12a is a plan view showing certain electrical connections of the electrosurgical device.

As best shown in FIG. 5, electrical contacts J28 and J29 are coupled to the proximal end of insulated wire conductors 130a and 130b, respectively, of electrical cord 40. As shown in FIG. 12, the distal end of insulated wire conductors 130a, 130b ultimately couple with the bipolar electrodes 180a, 180b of device 10 as discussed in greater detail below.

Additionally, electro surgical unit 300 may be operated in a monopolar mode with monopolar power provided through power output BP+, in which case power output BP− is no longer utilized. Rather, as shown in FIG. 12, an additional cord 132 is utilized to connect a ground pad dispersive electrode 134, which is located on the patient, to the electro surgical unit 300 using wire conductor 136 and plug 138 at the end thereof which connects to the ground pad receptacle 308 (as shown in FIGS. 16 and 17).

During monopolar operation, an electrode of device 10 is used in conjunction with ground pad dispersive electrode 134 which is placed on the patient (also known as a patient return electrode or neutral electrode), typically on the back or other suitable anatomical location. An electrical circuit is formed between the electrode of device 10 and ground pad dispersive electrode 134 with electrical current flowing from the device electrode through the patient to ground pad dispersive electrode 134 in a manner known in the art.

During bipolar operation, the ground pad electrode 134 located on the patient is not required, and a second electrode providing an electrical pole is provided as part of device 10. An alternating current electrical circuit is then created between the first and second electrical poles of the device. Consequently, alternating current no longer flows through the patient's body to the ground pad electrode 134, but rather through a localized portion of tissue between the poles of the bipolar electrodes. Monopolar and bipolar power may be provided from electro surgical unit 300 in a manner known in the art.

Returning to FIG. 7, a control signal from electrosurgical unit 300 may be provided to electrical contact J14, which is configured to receive a control signal from electrosurgical unit 300 as part of a control circuit to control bipolar power output. The control signal may then communicated along an electrically conductive pathway to electrical contact J23. As shown in FIG. 5, electrical contact J23 may be coupled to the proximal end of insulated wire conductor 142 of electrical cord 40. As shown in FIG. 12, the distal end of insulated wire conductor 142 may be coupled to a radio-frequency power hand-switch activation assembly 146 within hand-piece 12. Hand-switch assembly 146 may comprise push button 148 which overlies a single pole, single throw, domed switch 150 on a platform comprising a printed circuit board, with the construction and wiring of the hand-switch assembly 146 known in the art. Upon depression of push button 148, the domed switch 150 beneath push button 148 forms a closed circuit which enables the control signal, here comprising a relatively low voltage direct current, to return and be sensed by electro surgical unit 300, generally via wire conductor 142, which then accordingly provides bipolar power. When the button 148 is released, the control circuit opens and the electro surgical unit 300 no longer receives the control signal to activate radio-frequency power. Consequently, the electro surgical unit 300 then deactivates the bipolar radio-frequency power output.

A control signal from electro surgical unit 300 may be provided to electrical contact J15, which is configured to receive a control signal from electrosurgical unit 300 as part of a control circuit to control monopolar power output. The control signal may then communicated along an electrically conductive pathway to electrical contact J24. While not shown in FIG. 5, electrical contact J24 may be coupled to the proximal end of insulated wire conductor 144 of electrical cord 40. As shown in FIG. 12, the distal end of insulated wire conductor 144 may be coupled to a radio-frequency power hand-switch activation assembly 152 within hand-piece 12. Hand-switch assembly 152 may comprise push button 154 which overlies a single pole, single throw, domed switch 156, which may comprise beryllium copper, on a platform comprising a printed circuit board, with the construction and wiring of the hand-switch assembly 152 known in the art. Upon depression of push button 154, the domed switch 156 beneath push button 154 forms a closed circuit which enables the control signal, here comprising a relatively low voltage direct current, to return and be sensed by electro surgical unit 300, generally via wire conductor 144, which then accordingly provides monopolar power. When the button 154 is released, the control circuit opens and the electrosurgical unit 300 no longer receives the control signal to activate radio-frequency power. Consequently, the electrosurgical unit 300 then deactivates the monopolar radio-frequency power output.

Exemplary hand switch assemblies may be found in U.S. Publication No. 2006/0149225, published Jul. 6, 2006, and U.S. Publication No. 2005/0090816, published Apr. 28, 2005, which are assigned to the assignee of the present invention and are hereby incorporated by reference in there entirety to the extent they are consistent.

In certain situations, during monopolar operation of device 10, electrode 180b may be undesirably energized due to capacitive coupling. In this case, monopolar radio-frequency energy traveling from electro surgical unit 300 along wire conductor 130a to electrode 180a may also be transferred to wire conductor 130b and ultimately to electrode 180b by capacitive coupling. In a situation where electrical cord 40 is approximately 10 feet long, and hand-piece 12 is approximately 8 inches long, radio-frequency monopolar energy may be transferred via capacitive coupling over a distance of almost 11 feet of device 10.

A solution to capacitive coupling may be to separate the parallel wire conductors 130a, 130b along their entire length by a suitable distance. However, a suitable distance, for the radio-frequency power levels being considered, would add significant width or diameter to cord 40, and become cumbersome for the user.

Figure 12B:
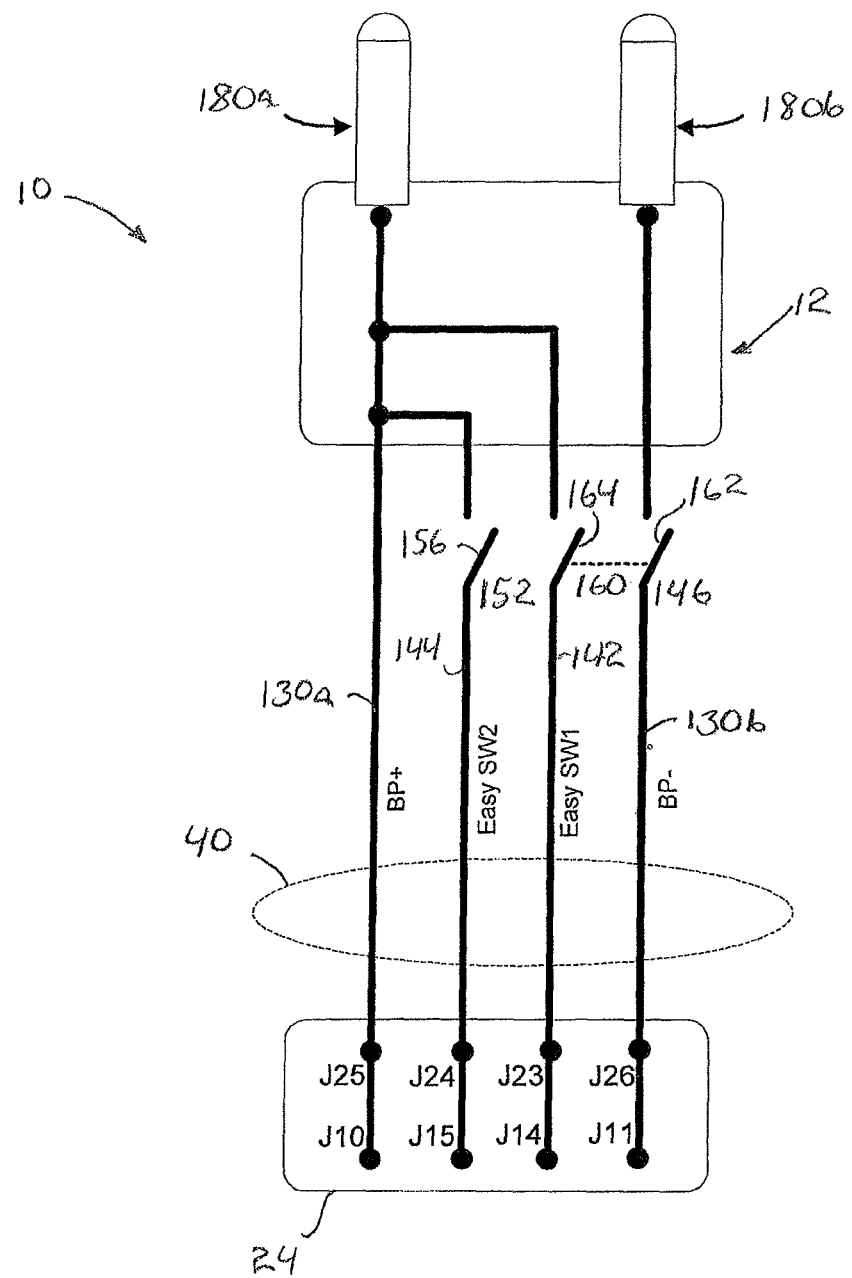
FIG. 12b is a plan view showing alternative electrical connections of the electro surgical device.

Another solution to capacitive coupling may be to introduce an electrical break or interruption in wire conductor 130b to effectively decrease the length of wire conductor 130b along which the transfer of radio-frequency energy to electrode 180b via capacitive coupling may take place. To this end, as shown in FIG. 12b, hand-switch assembly 146 to activate bipolar power is now in direct electrical communication with wire conductor 130b and electrode 180b. Also as shown, switch 150 of hand-switch assembly 146 as been replaced and hand-switch assembly 146 now comprises a double pole, single throw momentary switch 160 which is in series between electrode 180b and a bipolar power output of electro surgical unit 300 to be coupled to the device 10.

In the foregoing manner, during monopolar operation of device 10, radio-frequency energy traveling from electrosurgical unit 300 along wire conductor 130a to electrode 180a which may be transferred to wire conductor 130b by capacitive coupling can no longer travel to electrode 180b given pole 162 of double pole, single throw switch 160 is in the open position. Thus, any transfer of radio-frequency energy traveling from electro surgical unit 300 along wire conductor 130a to electrode 180a which may be transferred to electrode 180b by capacitive coupling may only occur through the portion of the electrical circuit distal to pole 162.

Now, with regards to bipolar operation of device 10, as noted above hand-switch assembly 146 comprises push button 148 which overlies double pole, single throw switch 160 to activate and deactivate bipolar power to the first and second electrodes 180 a, 180 b. Upon depression of push button 148, the double pole, single throw switch 160 beneath push button 148 simultaneously closes and connects two circuits. First, pole 162, initially in an open circuit position, is now placed in a closed and connected circuit position such that the bipolar radio-frequency energy may now be provided to electrode 180 b. Additionally, pole 164, also initially in an open circuit position, is now also placed in a closed and connected circuit position to provide a control circuit which enables the control signal, here comprising a relatively low voltage direct current, to return and be sensed by electrosurgical unit 300, generally via wire conductor 142, which then accordingly activates bipolar power. When the button 148 is released, both poles 162, 164 return to their initial opened positioned and the control circuit disconnects and the electro surgical unit 300 no longer receives the control signal and deactivates radio-frequency power. Consequently, the electrosurgical unit 300 then deactivates the bipolar radio-frequency power output. Furthermore, the circuit to electrode 180 b also opens, thus inhibiting electrode 180 b from receiving monopolar radio-frequency energy during the operation of device 10 in this manner. In this embodiment, the double pole, single throw switch 160 may be provided by two dome switches in overlapping arrangement on opposing sides of a cantilevered printed circuit board. In this manner, push button 148 may act directly upon one of the dome switches, causing the switch to close to form a closed circuit. Push button 148 may also cause the cantilevered printed circuit board to rotate and move the opposing dome switch thereon into contact with a mechanical stop which causes the second dome also to close to form a closed circuit.

Figure 12C:
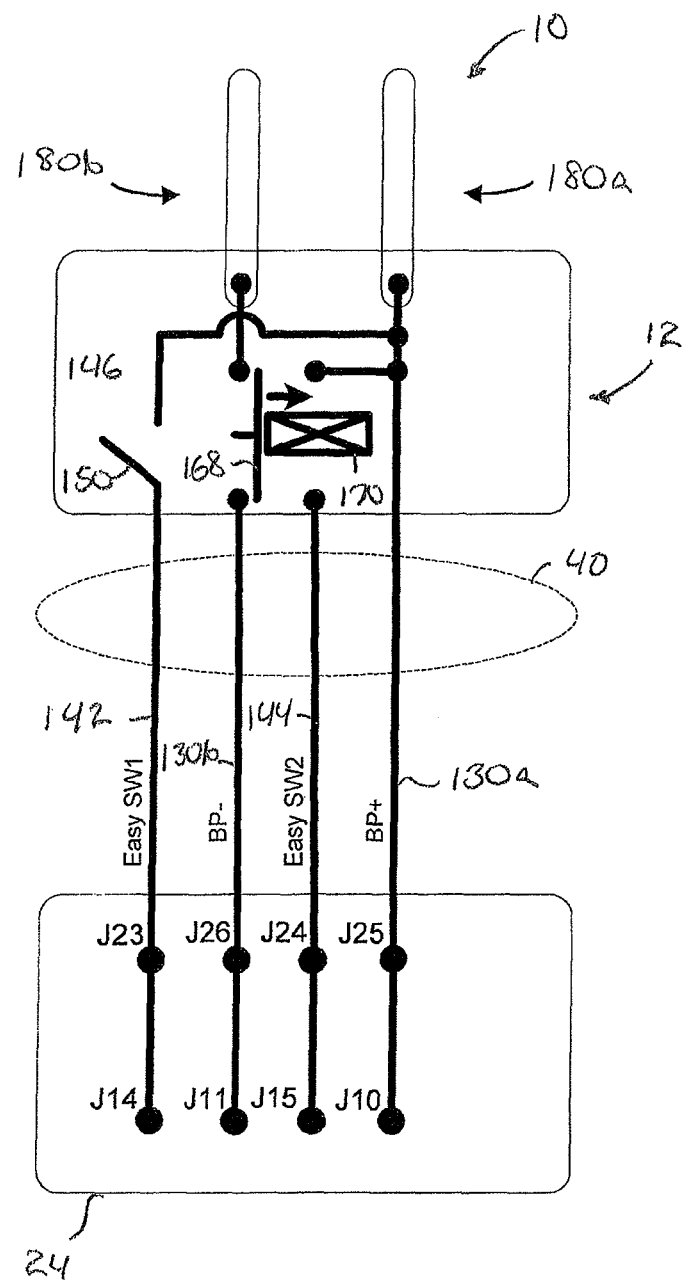
FIG. 12c is a plan view showing alternative electrical connections of the electrosurgical device.

In yet another embodiment, as shown in FIG. 12c, switch 156 of hand-switch assembly 152 has been replaced with switch 168 and includes bias spring 170, which may be a leaf-spring. As shown, when in a first position, switch 168 is in position to deactivate the monopolar power to electrode 180a of device 10 from electro surgical unit 300 as the control circuit for monopolar power is now open, and connect electrode 180b with bipolar power output of electro surgical unit 300. In this manner, when switch 150 is depressed, bipolar power may be provided to electrodes 180a, 180b. After switch 150 is released, switch 168 may be depressed, against the bias of spring 170, to activate monopolar power to electrode 180a, as well as inhibit capacitive coupling of electrode 180b to the monopolar power by disconnecting electrode 180b from conductor 130b. When switch 168 is released monopolar power is deactivated and spring 170 returns switch 168 to its initial position.

Electrosurgical unit 300 may also be configured to receive a stream of serial data including certain operating parameters and other information from device 10 concerning the set-up and use of device 10. In particular, as shown in FIG. 5, printed circuit board 24 may include an electronic memory 26 (also shown at U1 in FIG. 7), and more particularly an electrically erasable programmable read only memory (EEPROM) in which to store such operating parameters and other information.

For example, memory 26 may include a unique identifier (e.g. model number and serial number) and a fixed time period for use of device 10 (e.g. 24 hours) from the time of first radio-frequency activation which is then stored by electro surgical unit 300 for future reference. Memory 26 may include at least one operating parameter such as default settings for radio-frequency power level and fluid flow level for device 10, as discussed in greater detail below. Memory 26 may include settings for a range of radio-frequency power levels and fluid flow levels for device 10, which extend from a minimum radio-frequency power level and minimum fluid flow level to a maximum radio-frequency power level and maximum fluid flow level for device 10. Memory 26 may also include operating parameters such as one or more relationships which relate fluid flow level to the radio-frequency power level over a range of fluid flow levels and radio-frequency power levels for device 10. As shown in FIG. 7, data is received by electrosurgical unit 300 from memory 26 via electrical contacts J1 to J4.

Printed circuit board 24 also may include electrical contacts J12 and J13 which are configured to detect moisture or wetness on printed circuit board 24. Contacts J12 and J13 are configured to be part of a moisture monitoring circuit provided with a predetermined impedance. If the impedance between the contacts J12 and J13 decreases, such as may occur if fluid 502 where to form a bridge between the contacts thus electrically coupling the contacts, electrosurgical unit 300 may cease operation until the predetermined impedance value is attained.

Cartridge member 18, and in particular printed circuit board 24, also may include electrical contacts which are configured to receive power for additional features and accessories of device 10 including, for example a light, such as a light emitting diode (LED) or fiber optic light, to illuminate a tissue treatment site during a surgical procedure. The LED may require a relatively low power, such as a magnitude of 4-5 volts DC (direct current).

Cartridge member 18, and in particular printed circuit board 24 may also include electrical contacts which are configured to provide connection and transmit signals to a video recording source to record video, for example, of a tissue treatment site during a surgical procedure, which may be viewed by a video camera, such as a digital or fiber optic video camera, provided with device 10.

Having discussed the electrical and fluid communication of device 10 with electrosurgical unit 300 and fluid source 500, attention will now be directed to end effector of device 10 used for the treatment of tissue.

As previously discussed, the distal end of insulated wire conductors 130a, 130b are coupled to a proximal portion of shafts 124a, 124b of shaft member assembly 128 within hand-piece 12. Now, referring to FIG. 13, shaft member assembly 128 comprises two parallel, self-supporting, electrically conductive hollow shafts 124a, 124b, which comprise metal such as stainless steel tubing. Carried by and connected to the distal ends of shafts 124a, 124b are two laterally and spatially separated (by empty space) stationary contact elements comprising electrodes 180a, 180b which may be configured as mirror images in size and shape, and have a blunt distal end with a surface devoid of edges (to provide a uniform current density) to treat tissue. In the present embodiment electrodes 180a, 180b comprise an electrically conductive metal, such as stainless steel. Other suitable materials may include titanium, gold, silver and platinum.

In certain embodiments, one or both shafts 124a, 124b may be made of electrically non-conducting material except for the portion at the distal end that comes in contact with electrodes 180a, 180b. In these embodiment, an insulated wire conductor would extend and be joined to the electrically conducting portion of shaft 124a, 124b. In still other embodiments, shafts 124a, 124b may completely comprise electrically non-conducting material, in which case an insulated wire conductor would extend and be joined directly to electrodes 180a, 180b.

As shown in FIG. 13, each electrode 180a, 180b comprises an elongated portion 182a, 182b. With respect to length, in the present embodiment, elongated portion 182a, 182b has a length in the range of and any increment between 2 mm to 6 mm, and more specifically have a length of in the range of and any increment between 3 mm to 5 mm. With respect to spacing, in the present embodiment the spatial gap separation GS between electrodes 180a, 180b in the range of and any increment between 0.1 mm to 4 mm, and more specifically in the range of and any increment between 1 mm to 2.5 mm, and more specifically in the range of and any increment between 1.5 mm to 2.3 mm.

Figure 14:
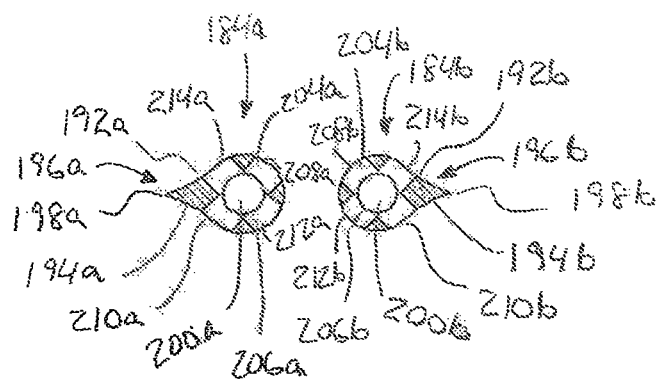
FIG. 14 is a close-up cross-sectional view of the electrodes of the device of FIG. 1 taken along line 14-14 of FIG. 13.

As best shown in FIG. 14, opposing concave sides 192a1194a of elongated portion 182a, and opposing concave sides 192b1194b of elongated portion 182b converge laterally to provide a wedge shaped blade portion 196a, 196b which terminates in a lateral cutting edge 198a, 198b which extends longitudinally along a length of each electrode 180a, 180b. As shown in FIG. 13, lateral cutting edge 198a, 198b transitions smoothly onto the distal end of each electrode 180a, 180b and forms a portion of the distal end of each electrode 180a, 180b.

Lateral cutting edge 198a, 198b may be configured to cut tissue electro surgically in the presence of monopolar radio frequency energy from electro surgical unit 300, without any fluid 502 being provided from fluid source 500. However, in other embodiments, lateral cutting edge 198a, 198b may be configured to cut tissue with fluid 502 being provided simultaneously from device 10, or be configured to cut tissue mechanically without electro surgical energy. Furthermore, while two cutting edges 198a, 1988b are shown, only one of the edges 198a or 198b may be configured to cut tissue electrosurgically or mechanically. In such instance, the blade portion of one electrode may be eliminated and the elongated portion may be completely cylindrical.

As shown in FIG. 13, electrodes 180a, 180b and elongated portions 182a, 182b terminate in distal end portion 186a, 186b. The distal end portion 186a, 186b of electrodes 180a, 180b are configured to move and slide with painting action across a tissue surface in the presence of bipolar radio frequency energy from electrosurgical unit 300 and fluid 502 from the fluid source 500. As shown, the distal end portion 186a, 186b of each electrode 180a, 180b has a blunt, rounded shape which provides a smooth contour surface. More specifically, as shown, distal end portion 186a, 186b of each electrode 180a, 180b comprises a spherical portion 190a, 190b. In the present embodiment, spherical portion 190a, 190b has a radius in the range of and any increment between 0.5 mm to 1.5 mm, and more specifically in the range of and any increment between 0.75 mm to 1.15 mm.

Figure 15:
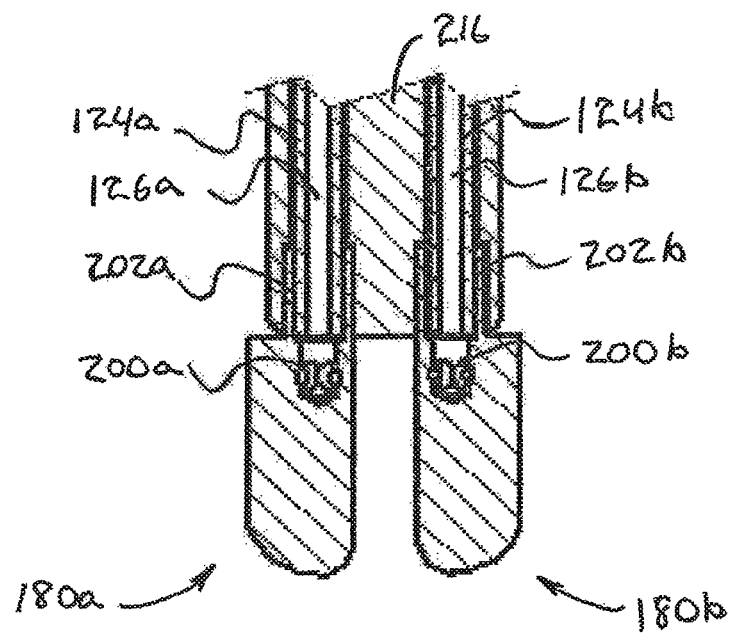
FIG. 15 is a close-up cross-sectional view of a distal end portion of the device of FIG. 1 taken perpendicular to line 14-14 of FIG. 13.

As best shown in FIGS. 14 and 15, within a cylindrical portion 184a, 184b of each electrode 180a, 180b proximal to distal end portion 186a, 186b, each electrode 180a, 180b includes a longitudinally oriented linear blind bore 200a, 200b and counter bore 202a, 202b. As shown in FIG. 15, the outside diameter of a distal end portion of each shaft 124a, 124b may be configured to extend into counter bore 202a, 202b of electrodes 180a, 180b and fit with the diameter of counter bore 202a, 202b, with the distal end of each shaft 124a, 124b in contact with the bottom of the counter bore. The electrodes 180a, 180b and shafts 124a, 124b may then be welded together. In alternative embodiments, the outside diameter of shafts 124a, 124b may be configured to fit with the diameter of counter bore 202a, 202b to form a press (interference) fit to provide a secure connection. In other alternative embodiments, electrodes 180a, 180b may be assembled to shafts 124a, 124b by threaded engagement. In still other embodiments, electrodes 180a, 180b may be detachably assembled to shafts 124a, 124b such that they may be removed from the shafts 124a, 124b, preferably manually by human hand.

In addition to blind bore 200a, 200b and counterbore 202a, 202b, as shown in FIG. 14, electrodes 180a, 180b also include a through bores 204a1206a and 204b1206b which perpendicularly intersects bore 200a, 200b and perpendicularly intersect one another to provide outlets 208a1210a1212a1214a and 208b/210b/212b1214b for fluid 502. Thus, after fluid 502 flows through the lumens 126a, 126b of shafts 124a, 124b, fluid 502 then flows through into the tubular passage provided by blind bore 200a, 200b and then into the tubular passage provided by through bores 204a1206a and 204b/206b where it thereafter exits device 10 from fluid outlets 208a1210a1212a1214a and 208b/210b1212b1214b, which are all proximal to distal end portion 186a, 186b of electrodes 180a, 180b. As shown in FIG. 14, fluid outlets 208a1212a and 208b/212b are defined by the cylindrical portion 184a, 184b of electrodes 180a, 180b, while fluid outlets 210a11214a and 210b1214b are defined by sides of 192a1194a and 192b1194b of blade portion 196a, 196b and adjacent cutting edge 198a, 198b.

As best shown in FIGS. 13 and 15, a portion of the lengths of shafts 124a, 124b are surrounded by and encapsulated in a common outer member 216, which may comprise a flexible plastic material. Outer member 216 electrically insulates the exposed length of shafts 124a, 124b.

Outer member 216 may be formed by injection molding. During the injection molding process, a sub-assembly comprising electrodes 180a, 180b and shafts 124a, 124b may be placed in an injection mold prior to the introduction of the plastic material. Thereafter, the mold may be closed and a thermoplastic may be injected into the unoccupied portions of the mold cavity to overmold and mold-in place portions of the sub-assembly as shown in FIG. 13. During the injection molding process, retainer clips (not shown) may provide the benefit of retaining shafts 124a, 124b in position relative to each other to better ensure that the shafts 124a, 124b are centrally located within the polymer molding.

To be hand shapeable by surgeons and other users of device 10, so that the device 10 may be used in a greater multitude of angles and locations, at least a portion of shafts 124a, 124b of device 10 may be malleable to provide a malleable shaft member assembly 128. Also, in this manner, a distal portion of shafts 124a, 124b may be bendable at an angle relative to the longitudinal axis of the proximal portion of shafts 124a, 124b during manufacturing of device 10 so they may be provided to users of device 10 at various angles. For example, angle may range from 5 degrees to 90 degrees, and more specifically, 15 degrees to 45 degrees, and even more specifically 30 degrees. As used herein, malleable means able to be shaped, particularly by bending (without a mechanical mechanism, such as a hinge or joint). It should be understood that shaft member assembly 128 may independently maintain the shape associated with the selected bent shape, and does not require additional components (e.g., pull wires, etc.) to maintain the selected bent shape. Furthermore, shaft member assembly 128 may maintain the selected, shape such that when device 10 is used to treat tissue, and will not overtly deflect from the selected shape. Furthermore, shaft member assembly 128 may be constructed such that a user can readily re-shape the shafts back to a straight state and/or other desired bent configurations.

Outer member 216, in addition to electrically insulating shafts 124a, 124b from one another, has been found to be particularly useful in facilitating the hand shaping of shafts 124a, 124b of shaft member assembly 128 simultaneously and with a similar contour without cracking and maintaining the tip spacing. In this manner, surgeons and other users of device 10 need not bend the shafts 124a, 124b individually.

To provide malleability, shafts 124a, 124b preferably have an outer wall diameter of about 0.063 inches and an inner wall diameter of about 0.032 inches. Shafts 124a, 124b also preferably are made from 304 stainless steel with a temper from about ½ to ¾hard, 130,000 to 150,000 psi. (pounds per square inch) tensile strength) and an elongation at break of about 40%. Shafts 124a, 124b with the foregoing properties provide sufficient stiffness as not to be too pliable during normal use of device 10, while at the same time inhibiting the shafts 124a, 124b from kinking or breaking when shaped for application. When the wall thickness may be too thin, shafts 124a, 124b may kink, and when the wall thickness may be too thick, the shafts 124a, 124b may be too stiff. Furthermore, a shaft 124a, 124bb with a larger diameter may also kink more than a shaft of smaller diameter. Shafts 124a, 124b may also be malleable for a portion of the length or full length depending on application. For example, the shafts 124a, 124b can be made with variable stiffness along the length and be malleable only for a distal portion thereof. This may be performed by controlled annealing of the shafts 124a, 124b only in the area where malleability may be desired.

Another embodiment of device 10 is shown in FIGS. 16a-16g which shows an alternative hand-piece 12a. In comparison to hand-piece 12, the electrodes 180a, 180b shown with hand-piece 12a are narrower with less mass as to provide a narrower incision when cutting tissue, making the device less obtrusive, and also enhancing visibility.

As best shown in FIG. 16b and FIG. 16c, each elongated portion 182a, 182b of electrodes 180a, 180b still may comprise a blade portion and have a lateral edge configured and arranged to operate in similar fashion to the previous embodiment. However, unlike the electrodes 180a, 180b of FIG. 13, the cylindrical portion 184a, 184b has been eliminated. The elongated portion 182a, 182b provides a blade shaped member with an elongated substantially planar body having a length significantly greater than its width, and a width significantly greater than its thickness. Here, for example, the length may be in the range of and any increment between 6 mm to 15 mm, the width may be in the range of and any increment between 2 mm to 3 mm, and the thickness may be in the range of and any increment between 0.25 mm to 0.75 mm. With respect to spacing, in the present embodiment the spatial gap separation GS between the electrodes 180a, 180b is the same as for the previous embodiment. As shown, to provide a self-supporting single layer construction, each electrode 180a, 180b may be formed from planar metal in the form of a metal strip and, more specifically, sheet metal which may be formed by stamping or otherwise formed using a stamping die or other forming die.

Figure 16A:
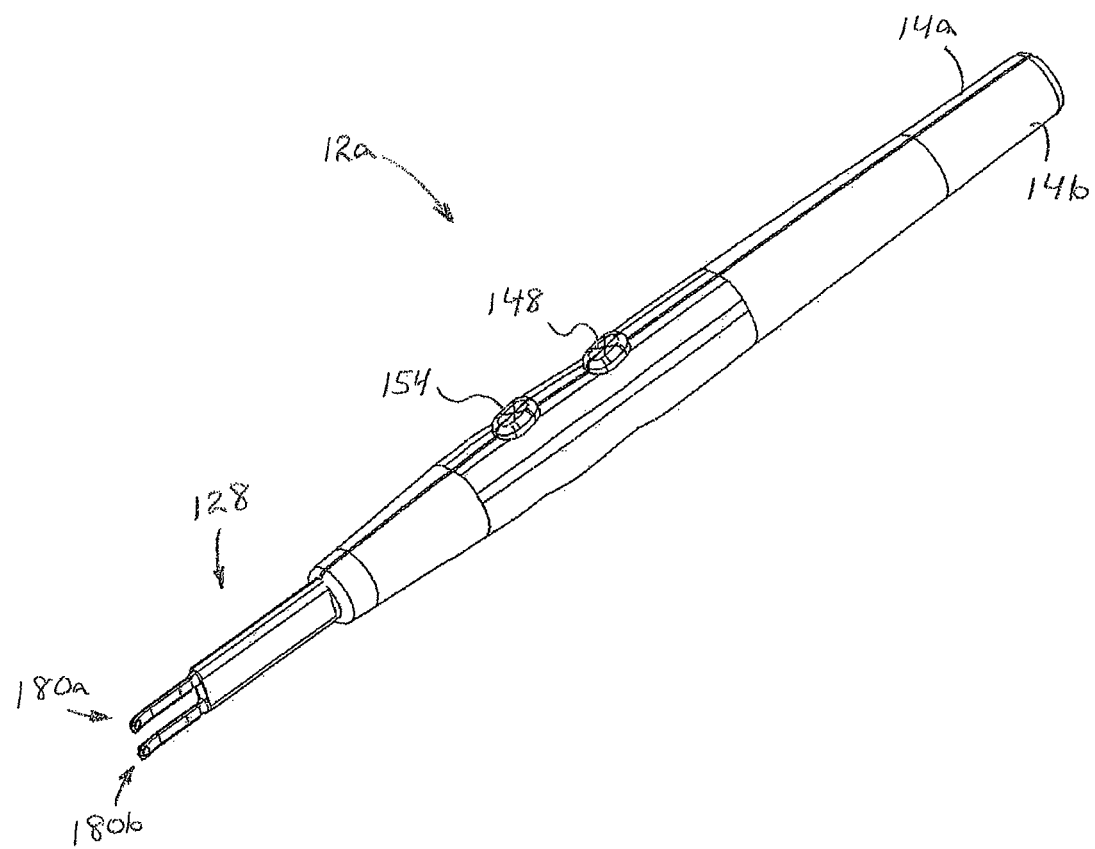
FIG. 16a is a perspective view of an electro surgical device according to another embodiment of the invention.
Figure 16D:
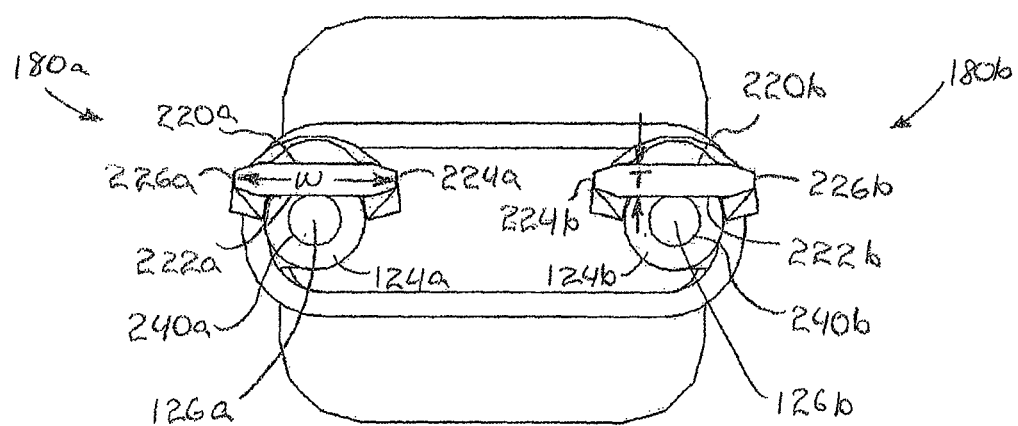
FIG. 16d is a close-up cross sectional view of the device of FIG. 16a taken perpendicular to line 16d-16d of FIG. 16c.

As best shown in FIG. 16d, each elongated portion 182a, 182b comprises opposing sides 220a/222a, 220b/222b; a medial edge 224a, 224b and a lateral edge 226a, 226b. To better clarify orientation, the thickness T of each elongated portion 182a, 182b is shown to separate sides 220a, 220b from sides 222a, 222b, while the width W of each elongated portion 182a, 182b is shown to separate the medial edges 224a, 224b from the lateral edges 226a, 226b.

Lateral edge 226a, 226b may further include a bevel on either or both sides thereof to provide a single or double bevel lateral edge, respectively. As shown, elongated portion 182a includes a bevel 227a, 229a on each side 220a, 222a, respectively, to provide double bevel edge 226a. Similarly, elongated portion 182b includes a bevel 227b, 229b on each side 220b, 222b, respectively, to provide double bevel edge 226b.

Lateral edge 226a, 226b, as well as distal end 228a, 228b may be configured to cut tissue electro surgically in the presence of monopolar radio frequency energy from electro surgical unit 300, without any fluid 502 being provided from fluid source 500. However, in other embodiments, lateral cutting edge 226a, 226b may be configured to cut tissue with fluid 502 being provided simultaneously from device 10, or be configured to cut tissue mechanically without electrosurgical energy. Furthermore, while two cutting edges 226a, 226b are shown, only one of the edges 226a or 226b may be configured to cut tissue electro surgically or mechanically.

Medial edges 224a, 224b are also shown to include a bevel on both sides thereof to provide a double bevel medial edge. However, unlike double bevel lateral edge 226a, 226b, double bevel medial edge 224a, 224b is not intended to be used to cut tissue and the double bevel exists predominately as a result of electrodes 180a, 180b being interchangeable for ease of manufacturing.

Referring back to FIGS. 16b and 16c, each electrode 180a, 180b is shown to have a distal (terminal) end 228a, 228b which is rounded, particularly from each medial edge 224a, 224b to the lateral edge 226a, 226b of the elongated portion 182a, 182b of each electrode 180a, 180b. More particularly, each rounded distal end 228a, 228b may be defined by a uniform radius. In this manner, the distal end of the device is void of sharp corners which could inadvertently snag, pierce or otherwise damage tissue.

As best shown in FIGS. 16e and 16f, each electrode 180a, 180b (only electrode 180a is shown, electrode 180b is similar) may further include a distal portion 230a, 230b which is at an obtuse angle A relative to side 220a, 220b and proximal portion 232a, 232b, with the obtuse angle A having a vertex which extends across the width of each electrode 180a, 180b. In this manner, each electrode 180a, 180b may have the general shape of a ski tip. In certain embodiments, the obtuse angle A may be in a range of and any increment between 91 degrees to 179 degrees and more particularly in a range of and any increment between 120 degrees to 175 degrees and even more particularly in a range of and any increment between 145 degrees to 170 degrees (e.g. 165 degrees). In this manner, the electrodes 180a, 180b are better configured to move across tissue during the treatment thereof as described in greater detail below. In various embodiments, the electrodes 180a, 180b may be malleable (e.g. made from Y4 to % hard stainless steel) to better facilitate bending of electrodes 180a, 108b to change the obtuse angle.

Figure 16G:
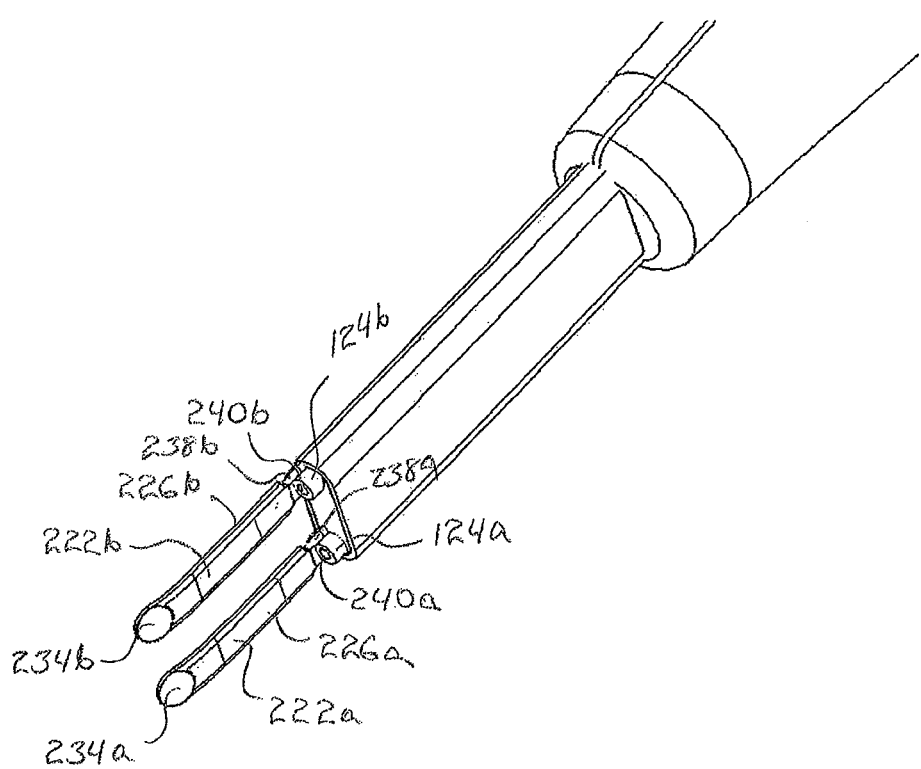

As best shown in FIGS. 16f and 16g, the distal portion 230a, 230b of each electrode 180a, 180b may further include a protrusion 234a, 234b located on side 222a 222b, which is opposite the side 220a, 220b of the obtuse angle, but on the same side as outlets 240a, 240b described in greater below. Stated another way, protrusion 234a, 234b is located on side 222a 222b of distal portion 230a, 230b which is at a reflex angle B relative to proximal portion 232a, 232b. Here, the reflex angle B may be in the range of and any increment between 181 degrees to 269 degrees, and may be calculated by subtracting the value of the obtuse angle A from 360 degrees.

As show, each protrusion 234a, 234b here comprises a convex curvature, shaped like a circular dimple, which provides a blunt, rounded shape which provides a smooth contour surface. In the present embodiment, the convex curvature has a diameter in the range of and any increment between 0.5 mm to 1.5 mm, and more specifically in the range of and any increment between 0.75 mm to 1.15 mm. Protrusion 234a, 234b may be formed by stamping or otherwise forming a recess 236a, 236b, here a concave curvature, in distal portion 230a, 230b on side 220a, 220b using a stamping die or other forming die.

As discussed in greater detail below, protrusions 234a, 234b of electrodes 180a, 180b may be used to move and slide electrodes 180a, 180b with painting action across a tissue surface in the presence of bipolar radio frequency energy from electro surgical unit 300 and fluid 502 from the fluid source 500, while, at the same time functioning as standoffs to separate lateral edges 226a, 226b from contacting the tissue surface and inhibit edges 226a, 226b from cutting the tissue when the device 10 is used in this orientation. In this orientation, sides 220a, 220b may be referred to as the upper sides relative to the tissue being treated while sides 222a, 222b may be referred to the lower sides.

In order to best facilitate use of the hand-piece 12a in the foregoing manner, electrodes 180a, 180b are shown to be coplanar (i.e. a thickness of each electrode 180a, 180b is in a common plane). More particularly, at least a portion of at least one of the opposing sides 220a/222a of electrode 180a is parallel and coplanar with opposing sides 220b/222b of electrode 180b, respectively. Even more particularly, at least a portion of each side 220a/222a of electrode 180a is parallel and coplanar with a corresponding side 220b/222b of electrode 180b, respectively.

With regards attachment to shafts 124a, 124b of shaft member assembly 128, electrodes 180a, 180b include a semi-circular tab portion 238a, 238b which may be welded to the side of shafts 124a, 124b. As shown, tabs 238a, 238b are welded to shafts 124a, 124b such that electrodes 180a, 180b extend distally from shafts 124a, 124b and fluid from the lumens 126a, 126b is expelled from fluid outlets 240a, 240b located at the distal end of shafts 124a, 124b and adjacent the electrodes 180a, 180b on the same side as protrusions 234a, 234b.

Figure 16H:
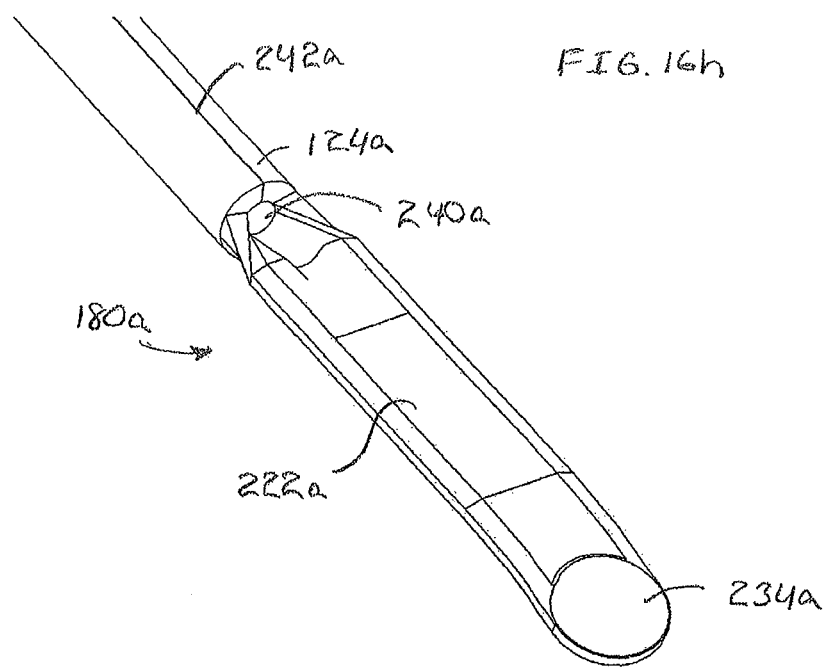
Figure 16I:
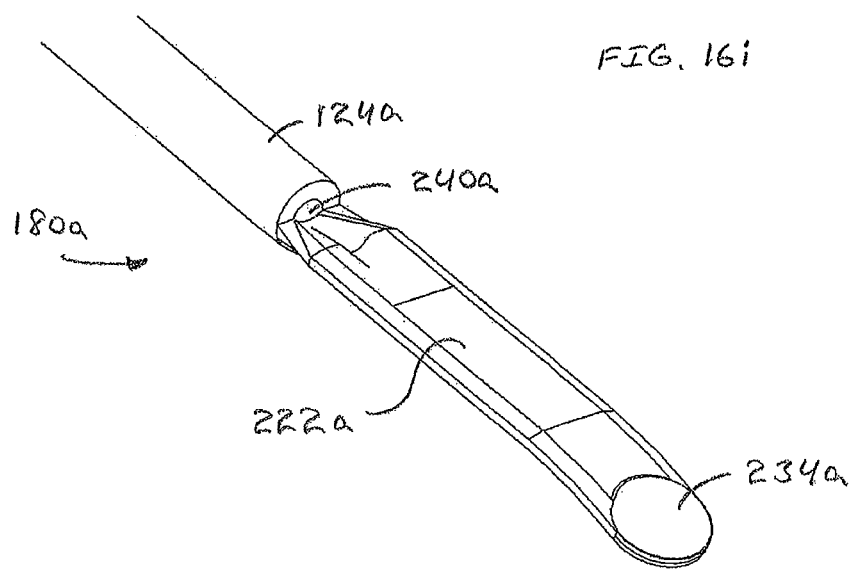

In alternative embodiments, electrodes 180a, 180b and shafts 124a, 124b may be unitary and continuous. In other words, may be formed from a single piece of metal which is uninterrupted. For example, the metal used to provide electrodes 180a, 180b, such as planar metal which may be in the form of a metal strip (such as sheet metal), may include a proximal portion which may be formed into the shape of a tube, as shown in FIG. 16h (only electrode 180a shown, electrode 180b similar), such as by roll forming, and thereafter welded along the longitudinal seam 242a to provide a sealed tube. Alternatively, a distal end portion of the metal shafts 124a, 124b, such as stainless steel tubes, may be flattened and shaped to provide the form and function of electrodes 180a, 180b as shown in FIG. 16i (only electrode 180a shown, electrode 180b similar). In this manner, an opening would also be provided in the side wall of shafts 124a, 124b adjacent the flattened portion to provide fluid outlets 240a, 240b.

Figure 16J:
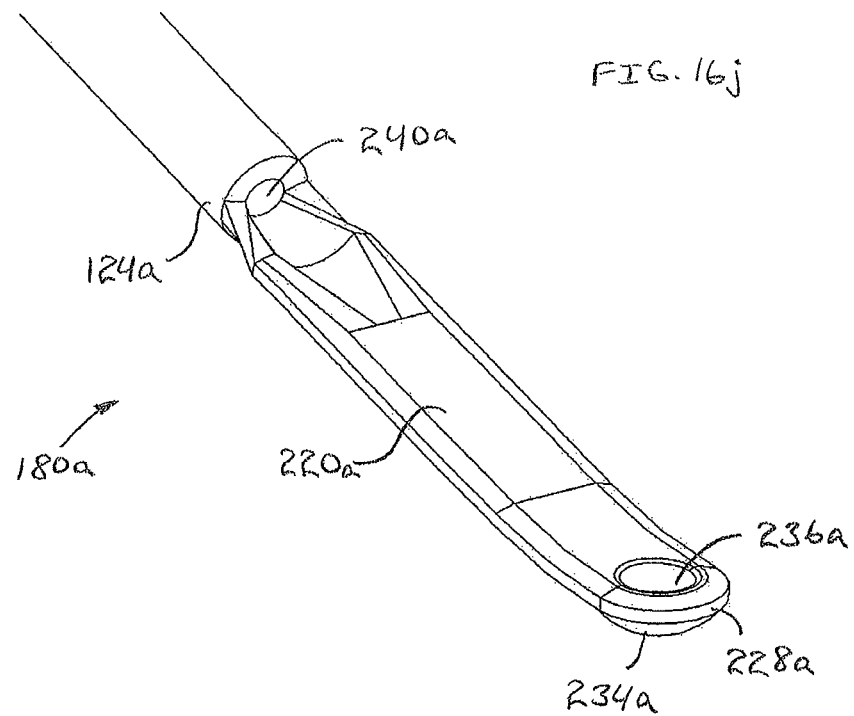
Figure 16K:
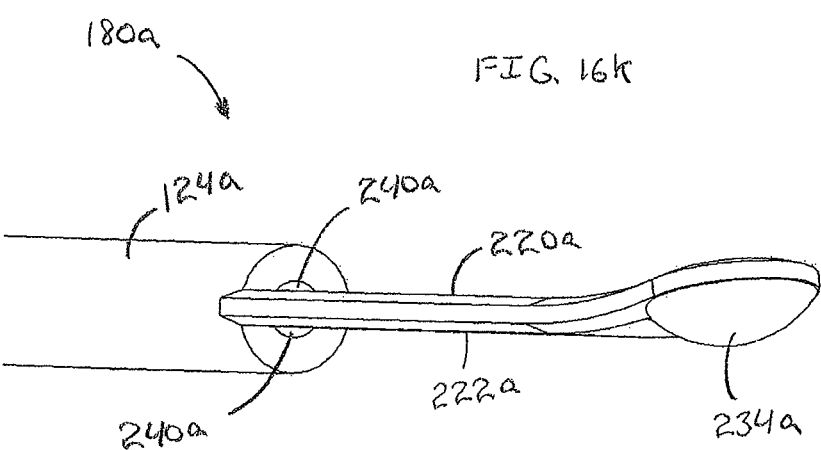

Also in alternative embodiments, fluid outlets 240a, 240b may be located on the opposite side of protrusions 234a, 234b, as shown in FIG. 16j (only electrode 180a shown, electrode 180b similar). In this manner, fluid from fluid outlets 240a, 240b may flow distally on surfaces 220a, 220b to recesses 236a, 236b. Thereafter, once recesses 236a, 236b are filled with fluid, the fluid may overflow the recesses 236a, 236b and flow out of the recesses to protrusions 234a, 234b. In yet another alternative embodiment, electrodes 180a, 180b may be positioned relative to the fluid outlets 240a, 240b such that fluid outlets 240a, 240b are located on both sides 220a, 220b and 222a, 222b as shown in FIG. 16k (only electrode 180a shown, electrode 180b similar).

Figure 16L:
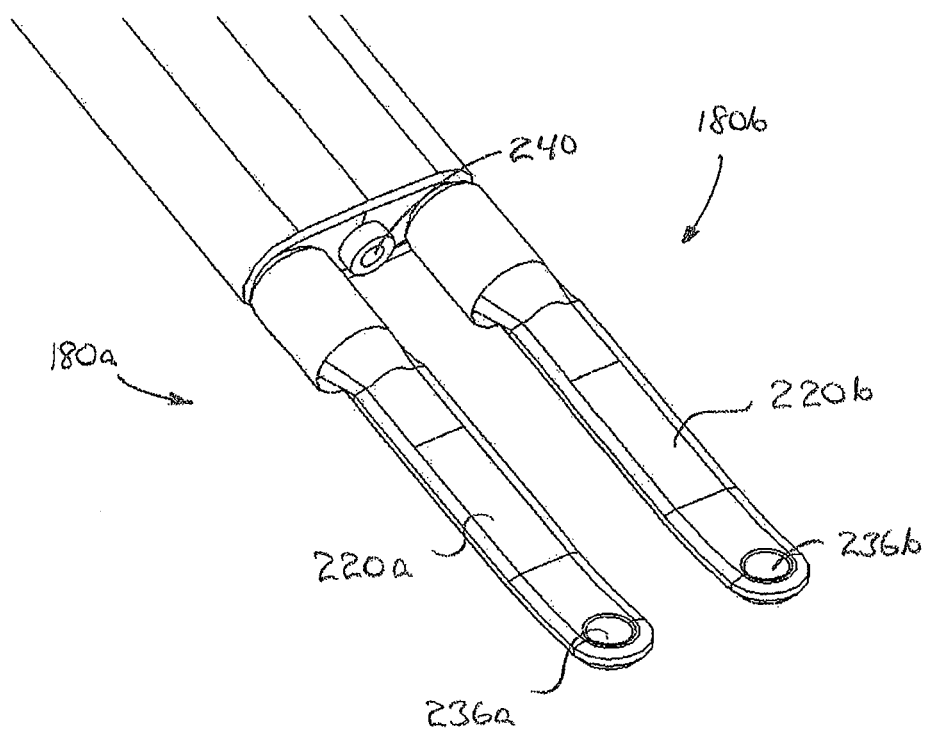

Also in alternative embodiments, fluid outlets 240a, 240b may be eliminated and a single fluid outlet 240 may be provided between electrodes 180a, 180b as shown in FIG. 16l.

Figure 17A:
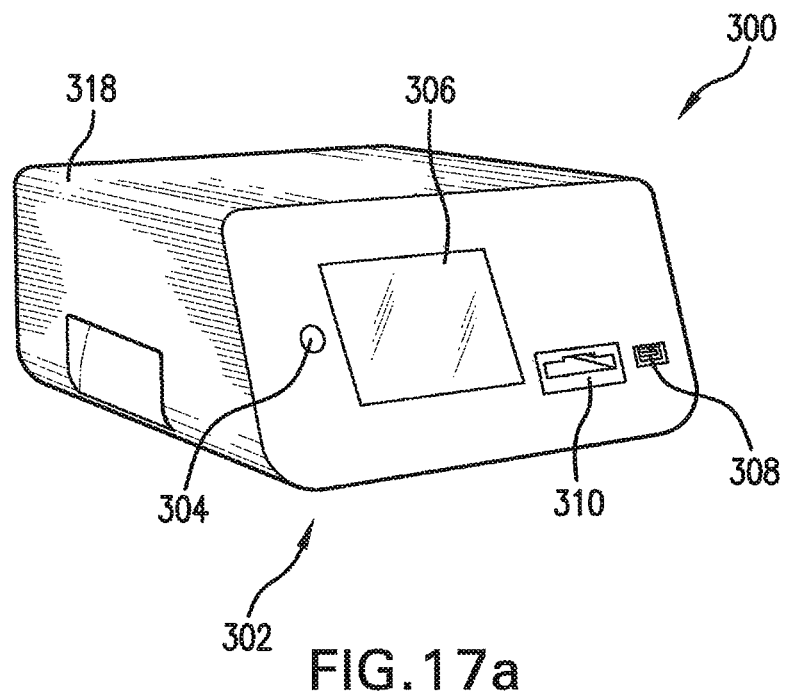
FIG. 17a is a perspective view of an electrosurgical unit according to one embodiment of the invention.
Figure 17B:
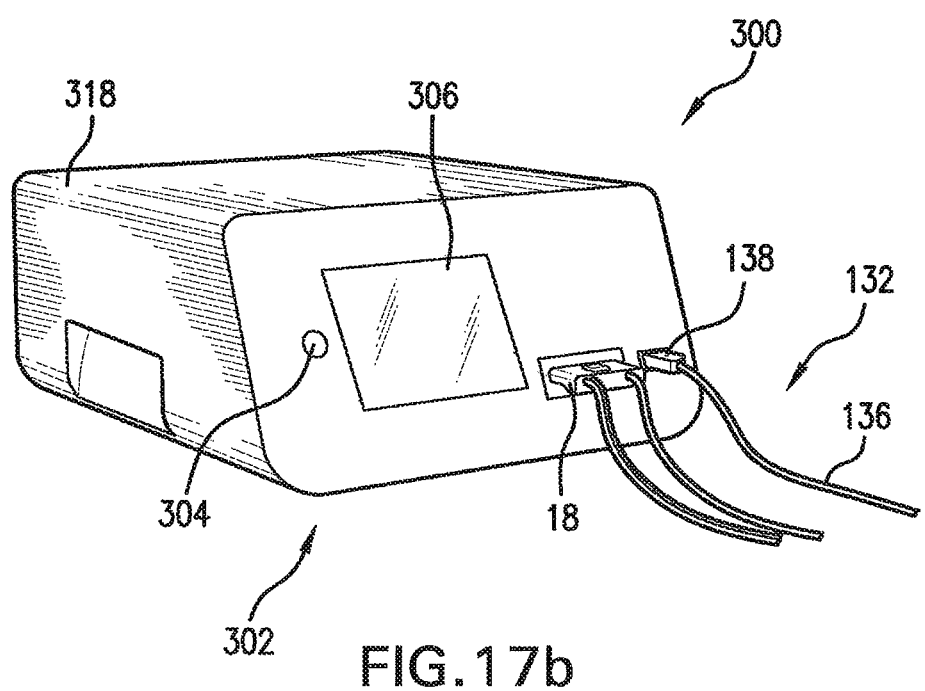
FIG. 17b is a perspective view of the electro surgical unit with the cartridge member of the cartridge assembly installed.

Having discussed electro surgical device 10 in detail, attention will now be directed to electrosurgical unit 300 shown starting at FIG. 17a. As shown in FIGS. 17a and 17b, electrosurgical unit 300 includes a front control panel 302. Front control panel 302 includes a power (on/off) switch 304 and touchscreen graphical user interface (GUI) 306. Front panel 302 also includes a ground pad receptacle 308 as well as a cartridge receptacle 310 configured to receive cartridge member 18 of cartridge assembly 16, which is shown installed in FIG. 17b.

Figure 18:
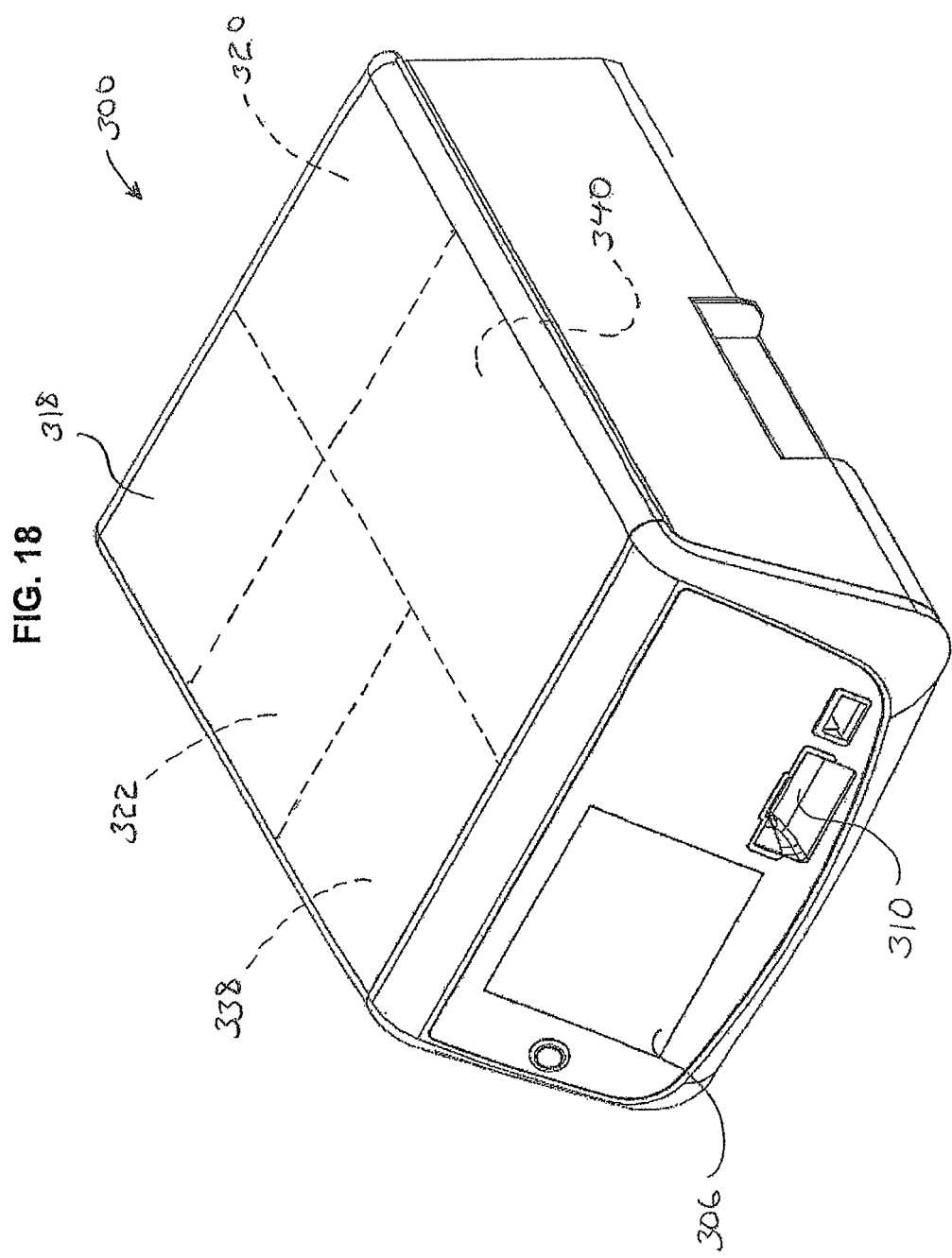
FIG. 18 is a perspective view of the electro surgical unit.

As shown in FIG. 18, electro surgical unit 300 includes an AC power supply 320, radio-frequency power source/generator 322, controller 338, including a central processing unit (CPU) and memory, and cartridge docking assembly 340 all interconnected and designed to communicate and function as an electro surgical unit which provides radio-frequency power in a manner known in the art.

Figure 19:
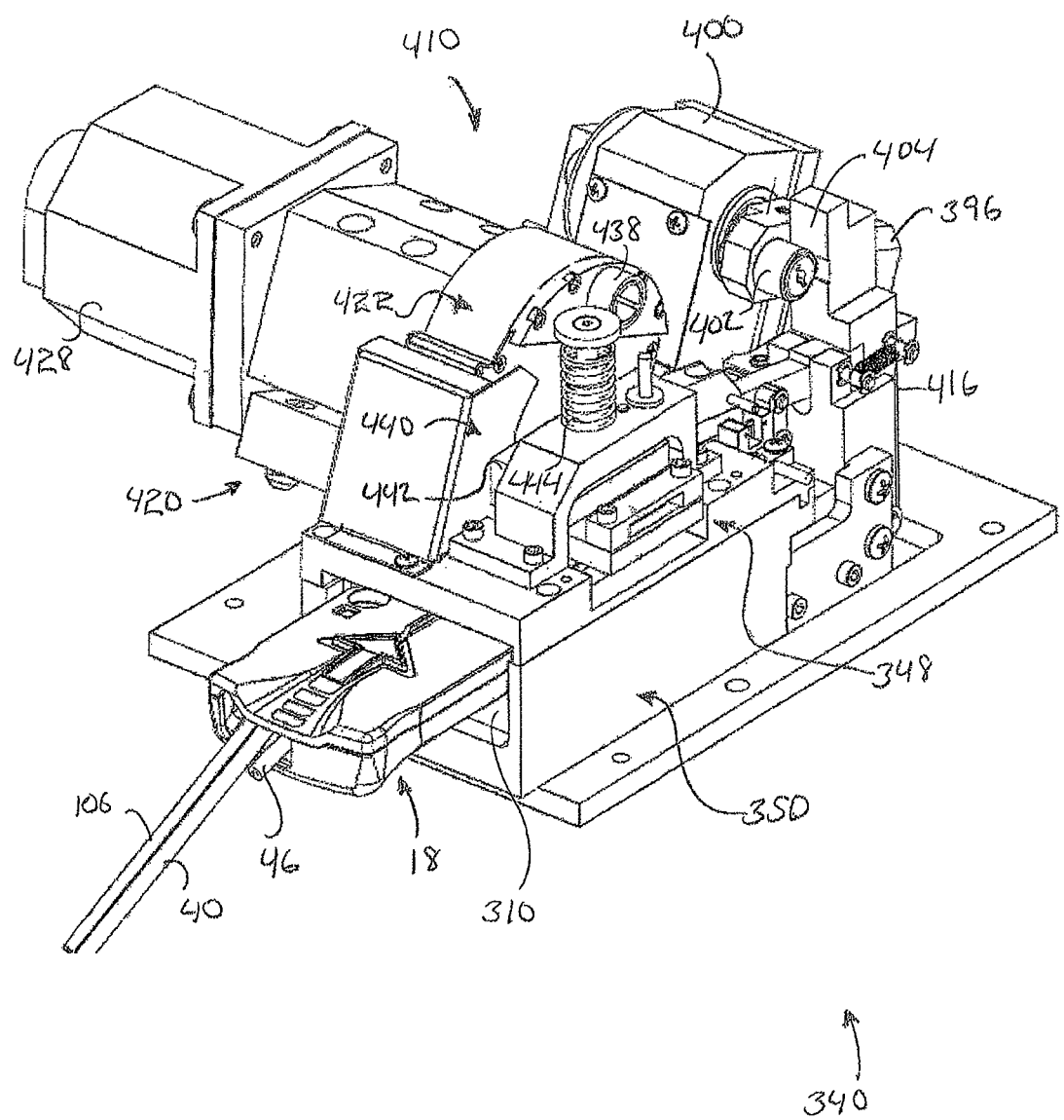
FIG. 19 is a front perspective view of the electro surgical unit's docking assembly with a movable docking mechanism in the up (non-use) position prior to the docking mechanism engaging with the cartridge member.
Figure 20:
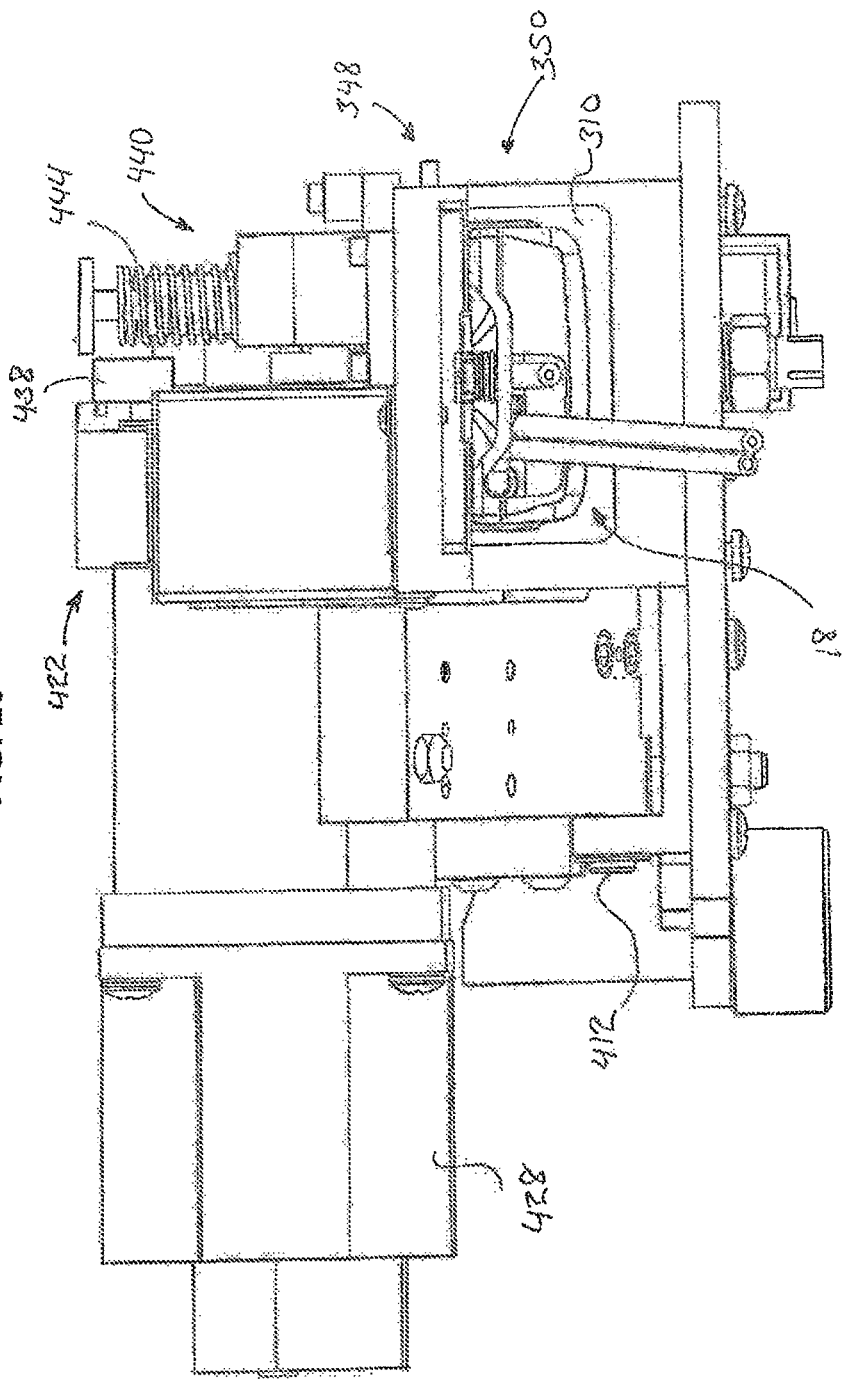
FIG. 20 is a front view of the docking assembly with the docking mechanism in the up position.
Figure 21:
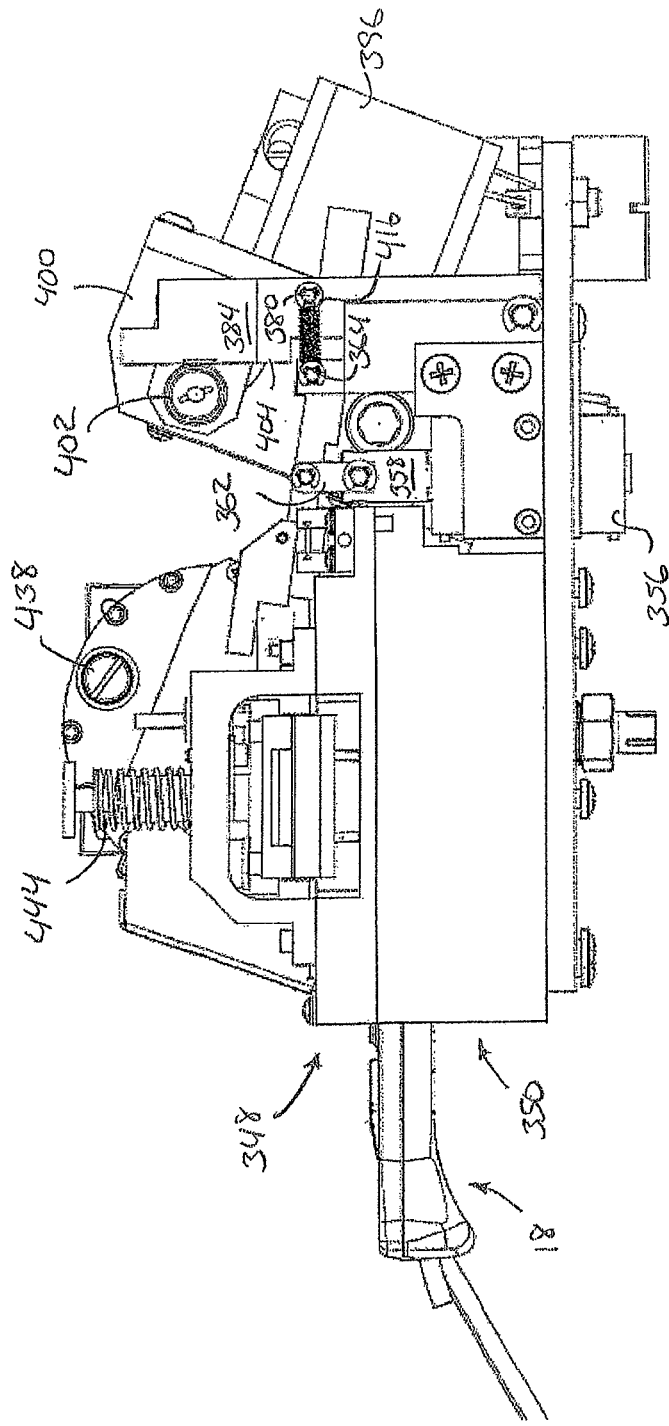
FIG. 21 is a right side view of the docking assembly with the docking mechanism in the up position.
Figure 22:
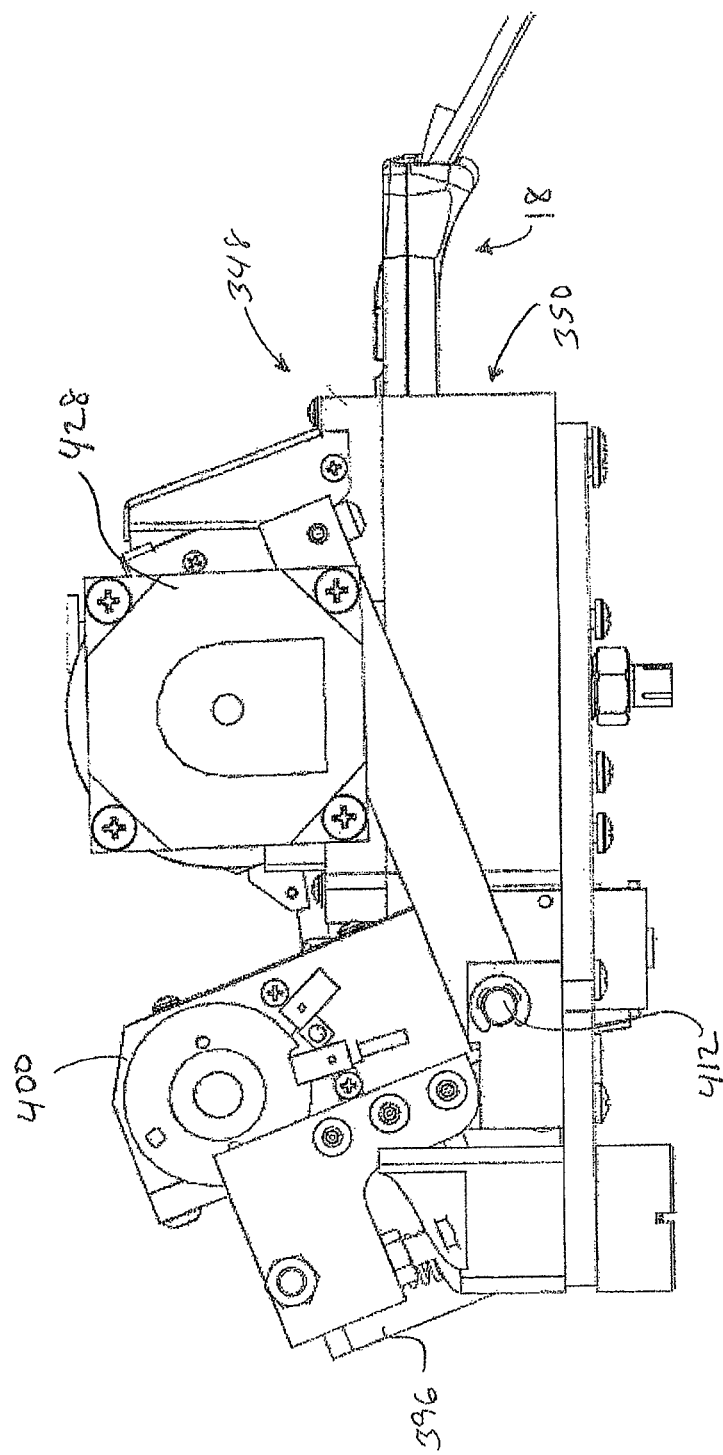
FIG. 22 is a left side view of the docking assembly with the docking mechanism in the up position.
Figure 23:
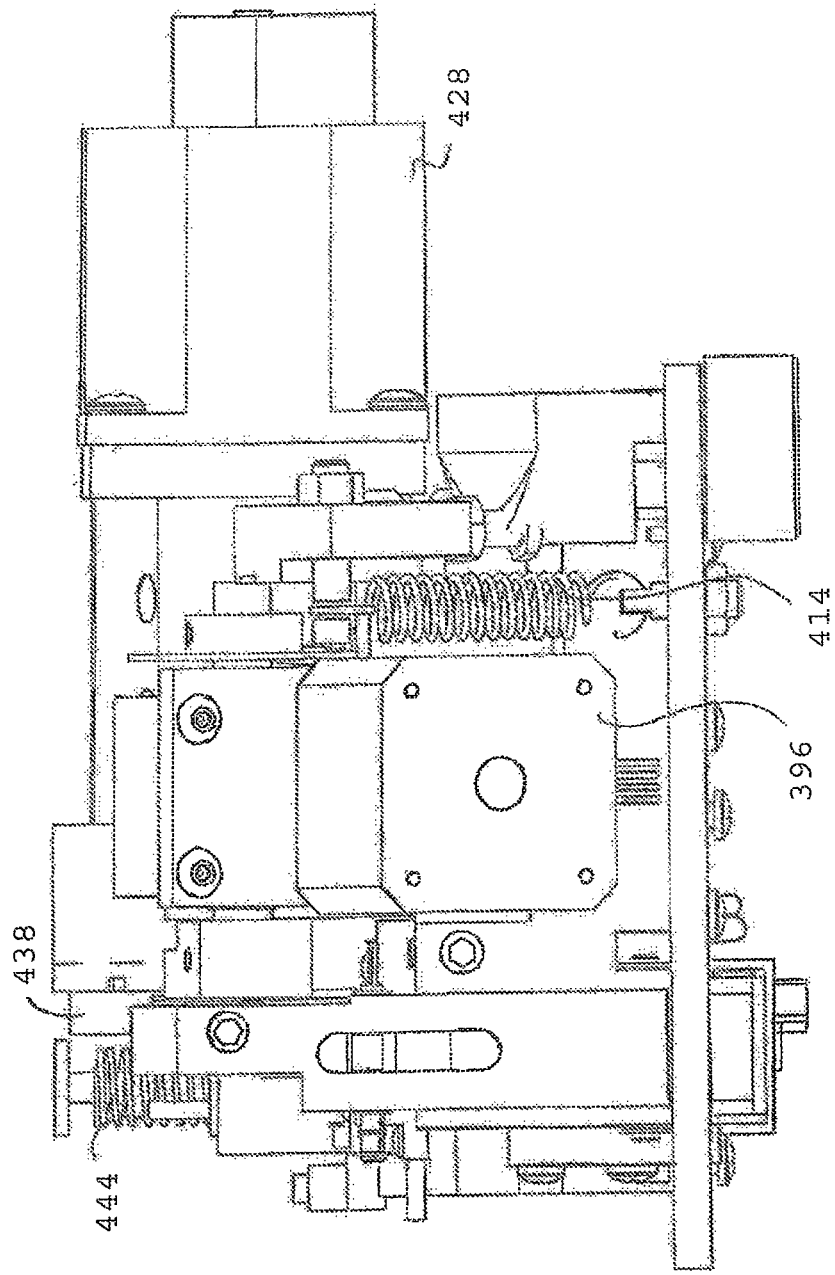
FIG. 23 is a rear view of the docking assembly with the docking mechanism in the up position.
Figure 24:
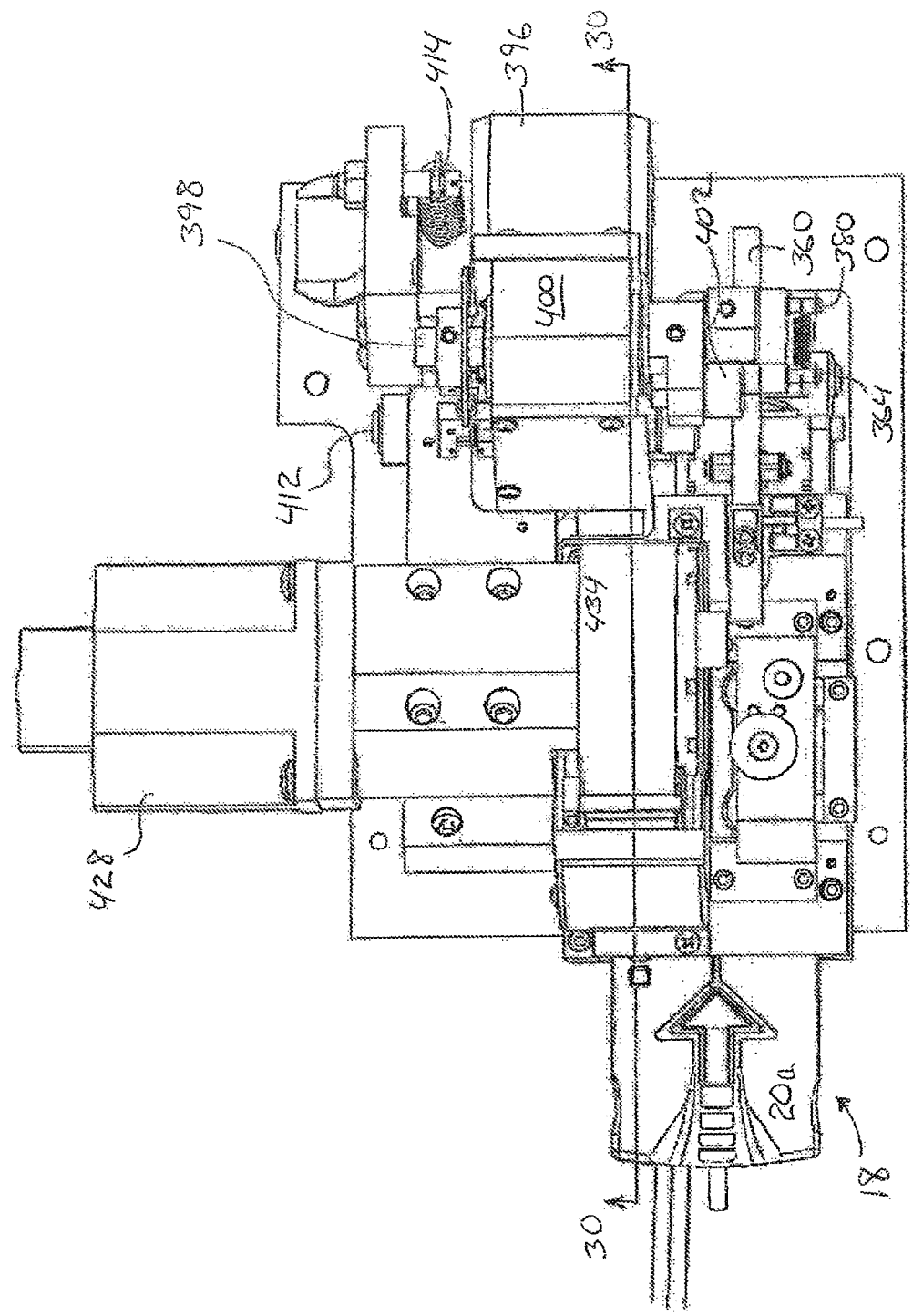
FIG. 24 is a top view of the docking assembly with the docking mechanism in the up position.

As shown in FIG. 19, electrosurgical unit 300 includes a docking assembly 340 with cartridge member 18 placed between upper receptacle enclosure 348 and lower receptacle enclosure 350. Front, right side, left side, rear and top views of the docking assembly 340 with a moveable docking mechanism 410 in the up (non-use) position prior to engaging with cartridge member 18 are shown in FIGS. 20-24, respectively. Operation of the docking assembly 340 will now be discussed in greater detail, with FIGS. 20-24 presented as needed.

Figure 25:
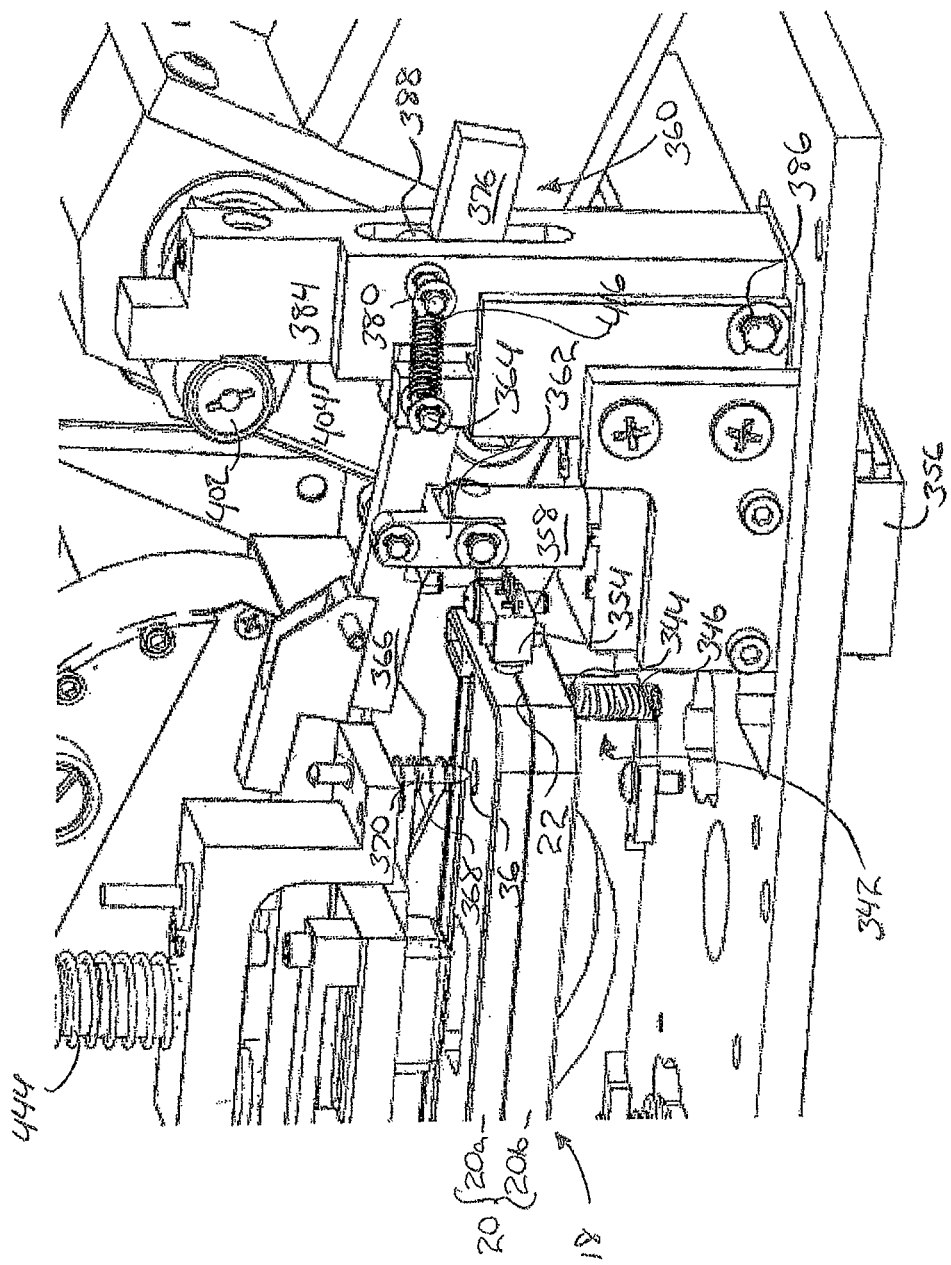
FIG. 25 is a rear perspective view of the docking assembly with the docking mechanism in the up position.

Referring to FIG. 25, upper receptacle enclosure 348 and lower receptacle enclosure 350 have been hidden to better show the operation of docking assembly 340. As shown in FIG. 25, near the end of insertion of cartridge member 18, the distal end 22 of cartridge member 18 first interacts with engagement mechanism 342, which is to inhibit the cartridge member 18 from inadvertently sliding out of receptacle 310 and separating from electrosurgical unit 300, as well as releasably engage the cartridge member 18 when sufficient removal force may be applied to the engagement mechanism 342 to disengaged the cartridge member 18 and retract it from receptacle 310.

As shown, the engagement mechanism 342 comprises a spring loaded ball 344 which may enter a detent 34 (shown in FIG. 3) which may be provided as part of the lower cartridge enclosure 350 (not shown). Engagement mechanism 342 acts to hold the cartridge member 18 in a temporary fixed use position relative to the electrosurgical unit 300. As the cartridge member 18 is inserted into receptacle 342, the lower surface of cartridge body 20b slides over the spring loaded ball 344 with a sufficient insertion force to overcome the bias/compression force of the spring 346 and retract the ball 344. As the cartridge member 18 thereafter reaches its use position, the ball 344 enters a detent 34 formed in cartridge body 20b (shown in FIG. 3) which, under the force of compressed spring 346, now acts to hold the cartridge member 18 and electrosurgical unit 300 at their relative positions. Furthermore, the engagement mechanism 342 provides the user with tactile feedback that the cartridge member 18 has been properly received by electro surgical unit 300. Alternately, after ejection may be selected and a removal force is applied to cartridge member 18 sufficient to overcome the retention force applied by the spring 346, the spring 346 may again be compressed and the ball 344 removed from the detent 34 to facilitate removal of the cartridge member 18 from the electrosurgical unit 300.

As the ball 344 enters detent 34, the distal end 22 of cartridge member 18 now makes contact with a two position contact switch 354 which, when cartridge member 18 is absent, is in the open position. As cartridge member 18 is more fully inserted into cartridge receptacle 310 with an insertion force sufficient to close switch 354, an electrical circuit in the electrosurgical unit 300 may be closed which provides a signal to a controller 338 within electro surgical unit 300 that a cartridge member 18 has been fully inserted into cartridge receptacle 310. Upon receipt of the signal that a cartridge member 18 has been fully inserted into the cartridge receptacle 310, electro surgical unit 300 may now energize a solenoid 356.

Figure 26:
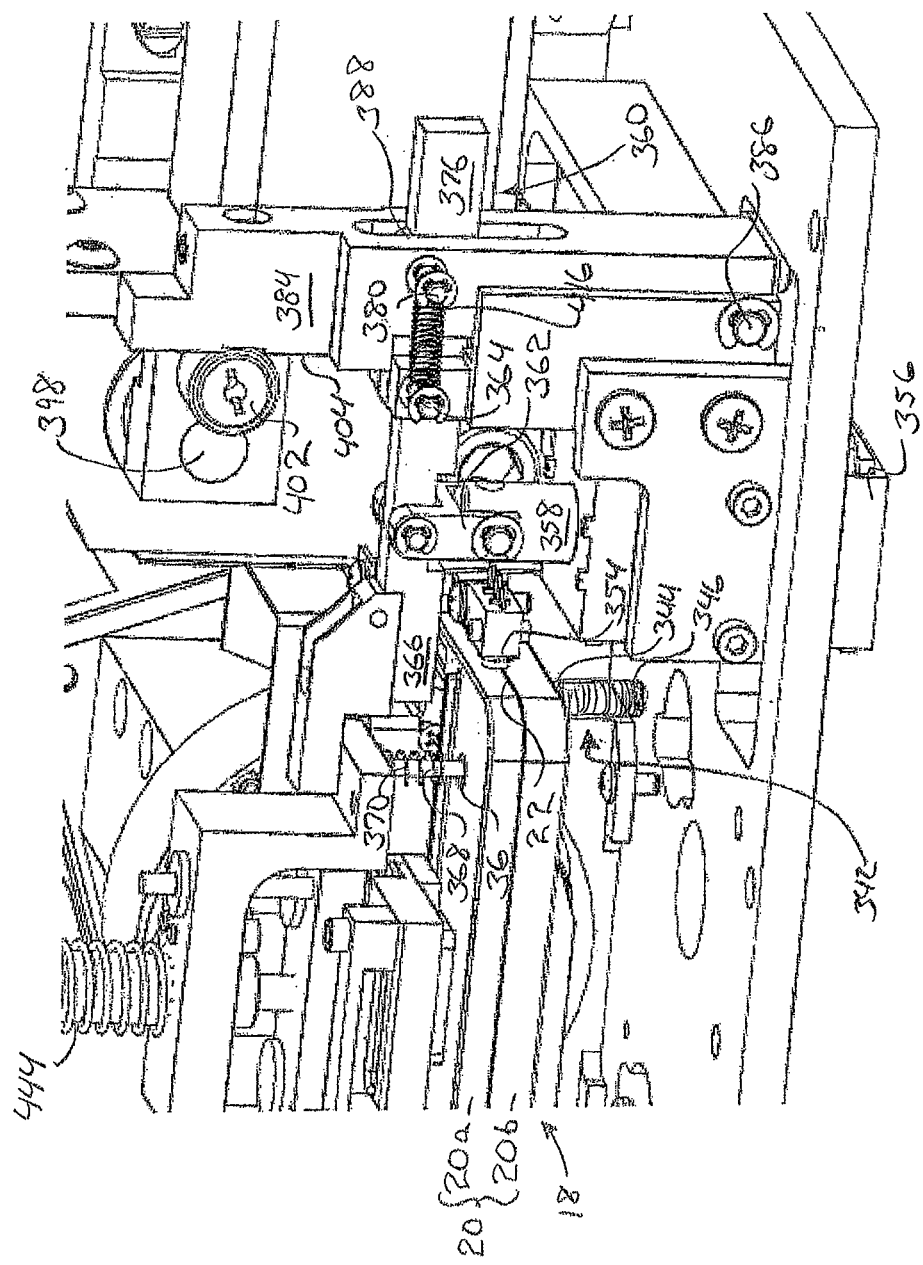
FIG. 26 is a rear perspective view of the docking assembly with the docking mechanism in the down (use) position.

Referring now to FIG. 25 and FIG. 26, solenoid 356 retracts armature 358, which may be coupled to lever 360 by pull bar 362. Consequently, upon retraction of armature 358, lever 360 may be rotated about pivot 364 and lever portion 366 rotates downward from its non-use (unengaged) position, as shown in FIG. 25, to its use (engaged) position, as shown in FIG. 26. As lever portion 366 rotates downward, pin 368 enters cylindrical cavity 36 formed in cartridge body 20a. Pin 368 performs multiple functions. First, pin 368 provides a locking mechanism to prevent inadvertent removal or dislodging of cartridge member 18 while electro surgical unit 300 is ready for operation. Pin 368 also provides a locating/positioning mechanism to further position cartridge member 18 relative to electro surgical unit 300 in addition to engagement mechanism 342.

Lever 360 may be pulled downward to its use (engaged) position with sufficient force to overcome the bias/compression force of spring 370, which thereafter returns lever 360 to its non-use position when power is removed from solenoid 356 and armature 358 is free to extend.

As lever 360 is rotated about pivot 364, lever portion 376, which is opposite lever portion 366, rotates upward about pivot 364. As shown in FIG. 27 and FIG. 28, lever portion 376 includes a catch 378 in the form of a notch into which locking pin 380 with roller 388 enter and are now captured as a result of the rotation of lever 360.

As a result of pin 380 and roller 388 entering catch 378 as shown in FIG. 28, lever 384 (shown in phantom in FIGS. 27 and 28), which rotates about pivot 386, may only travel rearward based on the length of catch 378. In other words, once pin roller 388 makes contact with the rearward surface 382 of catch 378, lever 384 may now be prevented from further rearward travel relative to lever 360 due to roller 388 contacting lever 384.

Returning to FIG. 26, once lever 360 is in its use position, an optical sensor then provides a signal to a controller within the electro surgical unit 300 that lever 360 is in such position. Upon receipt of the signal that lever 360 is now in its use position, electrosurgical unit 300 now activates electric motor 396 which turns shaft 398 via a gearbox 400. Shaft 398 provides an axle for cam 402 which, as a result of the rotation of shaft 398, contacts surface 404 of lever 384.

Upon rotation of cam 402 against surface 404 of lever 384, lever 384 may travel rearward until roller 388 makes contact with the rearward surface 382 of catch 378. As the position of lever 384 may now be fixed against moving rearwards by roller 388 fixated on contacting lever 384, surface 404 now provides a fixed load bearing surface against cam 402. As a result, upon further rotation of cam 402 against surface 404, movable docking mechanism 410 rotates downward and moves radially about pivot 412 (shown in FIG. 22) against the bias/tension force of spring 414 (shown in FIG. 23) until it reaches its use position as sensed by an optical sensor. Docking mechanism 410 is now in its use (engaged) position. In other words, ready to deliver radio-frequency power and fluid as designed. After use of electro surgical unit 300 is complete, a user may eject cartridge member 18 from unit 300 by selecting such control on unit 300, and the reverse of the docking procedure may be performed.

Should power be removed from solenoid 356 while docking mechanism 410 is in its use position, for instance if unit 300 is unplugged, electro surgical unit 300 may be configured to return docking mechanism 410 upward to its non-use position and allow cartridge member 18 to be removed. As indicated above, when power is removed from solenoid 356, armature 358 may be free to extend and lever portion 366 of lever 360 rotates upward about pivot 364 due to the force of spring 370 to remove pin 368 from cylindrical cavity 36 formed in cartridge body 20a. Simultaneously, lever portion 376 of lever 360 rotates downward about pivot 364 to disengage locking pin 380 with roller 388 from catch 378. Upon the disengaging of locking pin 380 and roller 388 from catch 378, lever 384 may now be free to move rearward about pivot 386. The force of spring 414 then overcomes the force of spring 416 and moves lever 384 rearward, releasing cam 402 from acting on surface 404. As cam 402 releases from surface 404, docking mechanism 410 is rotated upwards about pivot 412 due to the force of spring 414. As docking mechanism 410 returns to its non-use position, and cam 402 rotates back to the not in use position, lever 384 moves forward about pivot 386 due to the force of spring 416. In this manner, locking pin 380 and roller 388 are now positioned to be received by catch 378.

Figure 29:
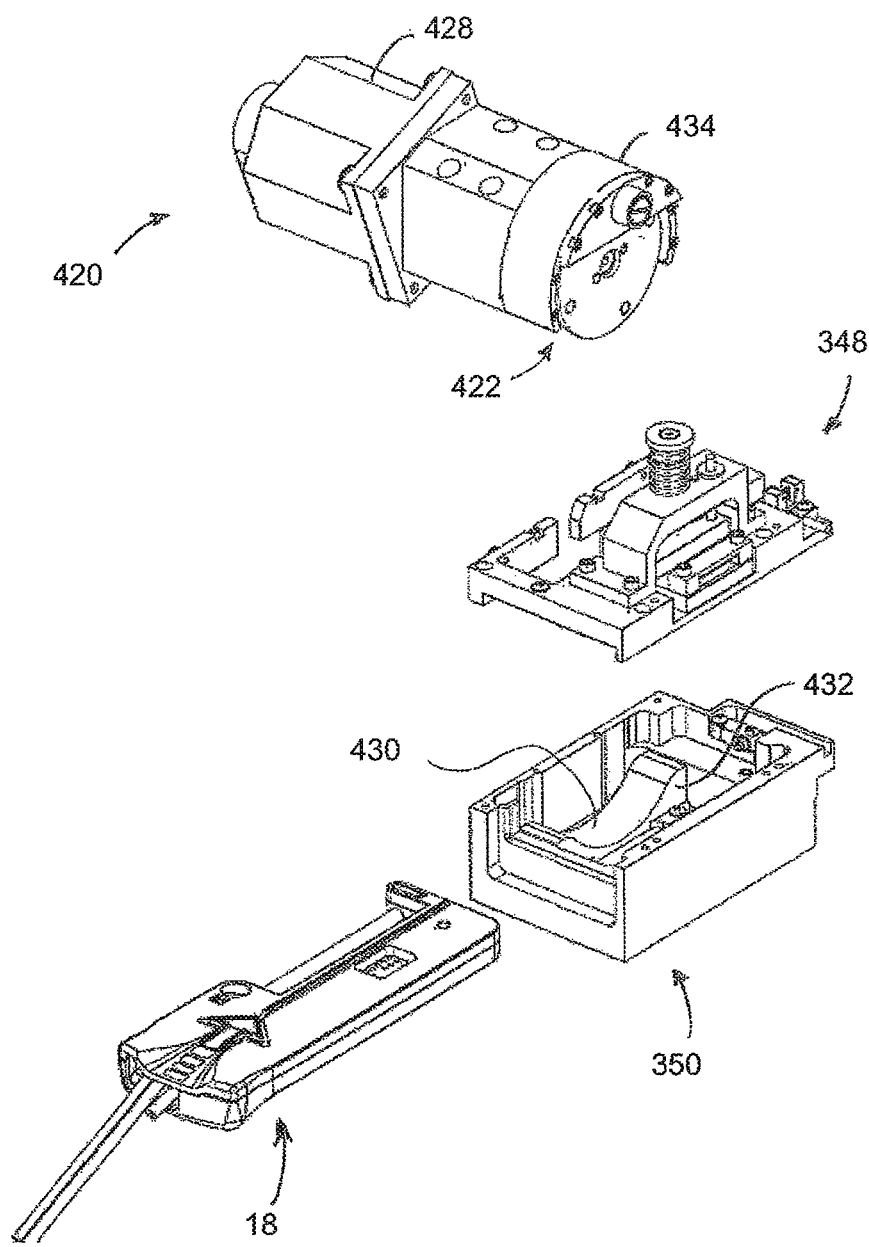
FIG. 29 is an exploded view of the cartridge member, upper receptacle enclosure, lower receptacle enclosure and a fluid delivery apparatus.
Figure 30:
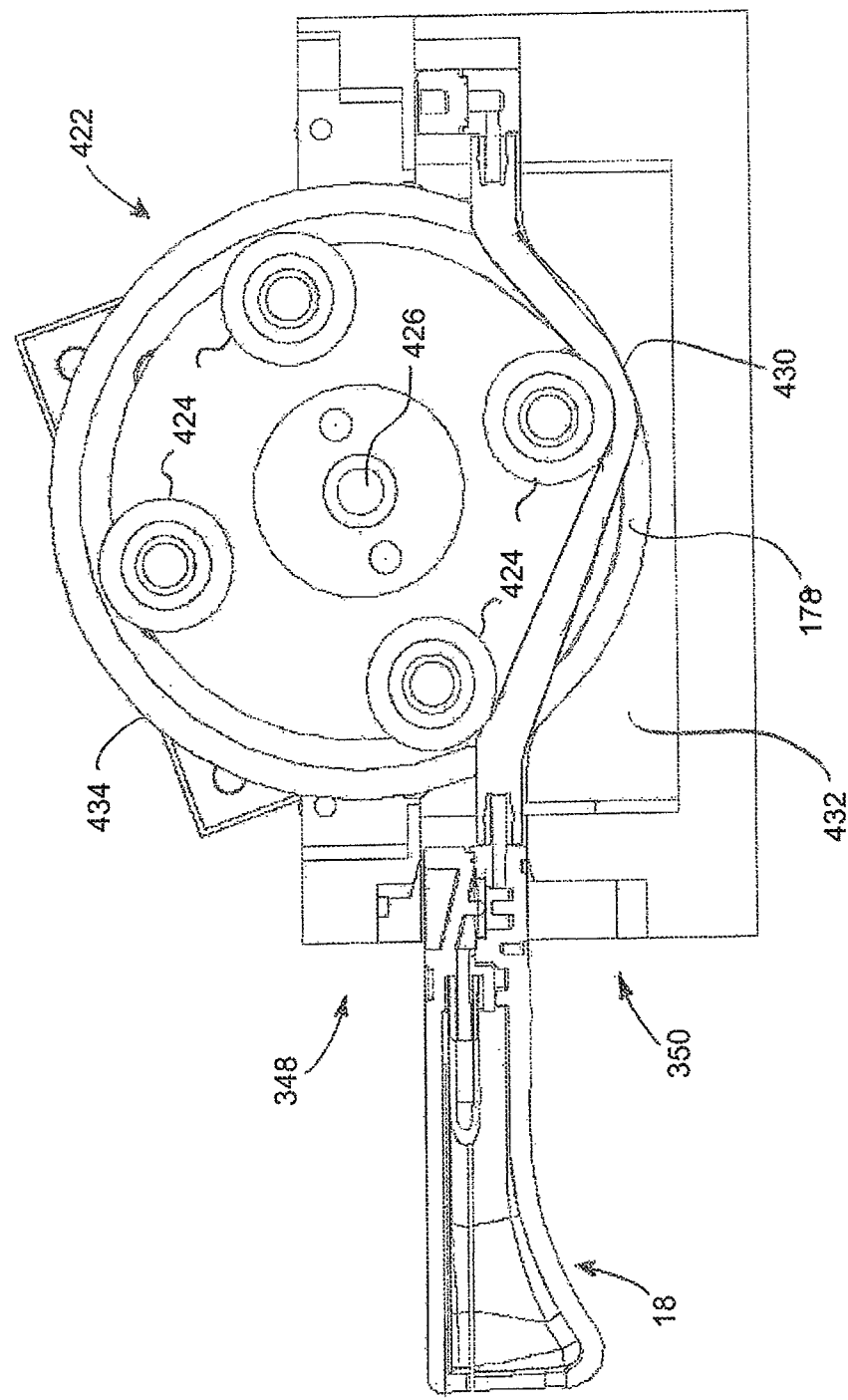
FIG. 30 is a cross sectional view taken through cartridge member, upper receptacle enclosure, lower receptacle enclosure and a fluid delivery apparatus at line 3030 of FIG. 24.

Referring now to FIG. 29, FIG. 29 shows an exploded view of the cartridge member 18, upper receptacle enclosure 348, lower receptacle enclosure 350 and a fluid delivery apparatus 420. Fluid delivery apparatus 420 comprises a peristaltic pump assembly 422, and more specifically a rotary peristaltic pump assembly. As shown in FIG. 30, compression elements shown as pinch rollers 424 of pump head 434 rotate about shaft 426 which may be turned by motor 428. As shown, when assembly is in its use position, rollers 424 engage and compress pump tubing segment 78 in a known manner against opposing load bearing surface 430 of semi-circular shoe/base 432 to pump fluid 502 from the fluid source 500 to the hand-held device 10.

Fluid 502 may be conveyed by peristaltic pump assembly 422 by waves of contraction placed externally on the delivery tubing segment 78 which are produced mechanically by rotating pinch rollers 424 which rotate on drive shaft 426 and intermittently compress the delivery tubing segment 78 against support surface 430. Peristaltic pumps are generally preferred, as the electro-mechanical force mechanism, here rollers 424 driven by electric motor 428, does not make contact with the fluid 502, thus reducing the likelihood of inadvertent contamination.

Figure 31:
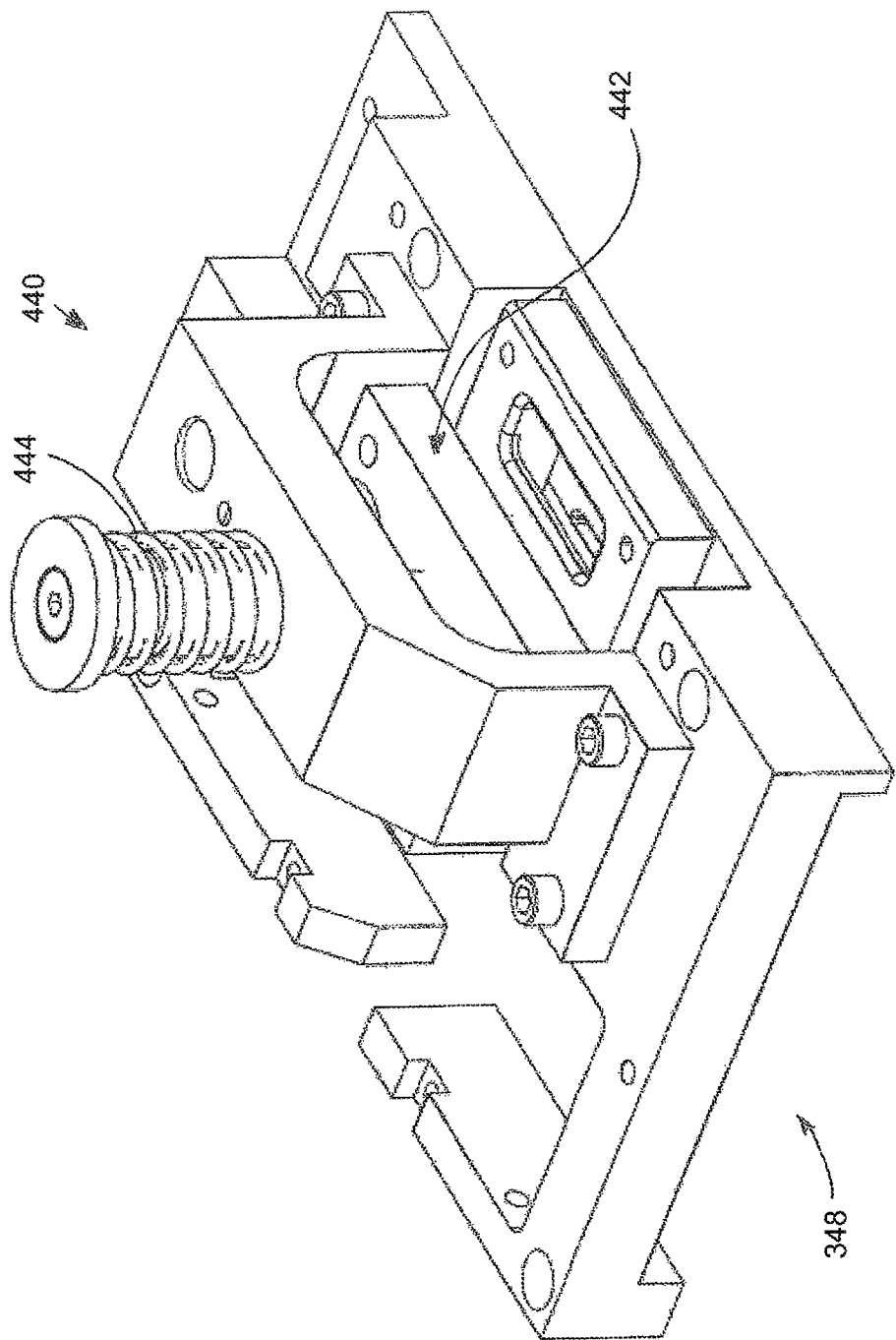
FIG. 31 is a perspective view of the upper receptacle enclosure with a radio-frequency power delivery apparatus.

Referring to FIG. 19 and FIG. 31, as docking mechanism 410 rotates downwards towards its use position, drive coupling 438 contacts radio-frequency power delivery apparatus 440 and pushes an electrical contact assembly 442 linearly downwards towards printed circuit board 24 of cartridge member 18 against the bias/compression force of spring 444. Conversely, upon docking mechanism 410 rotating upwards towards its non-use position, spring 444 raises electrical contact assembly 442 away from printed circuit board 24 and to its non-use position.

In the above manner, both power delivery apparatus 440 and fluid delivery apparatus 420 move simultaneously to save time as compared to if they were to move sequentially, as well jointly, thus requiring only one shared drive mechanism, here comprising motor 396, rather than two separate drive mechanisms.

Figure 32:
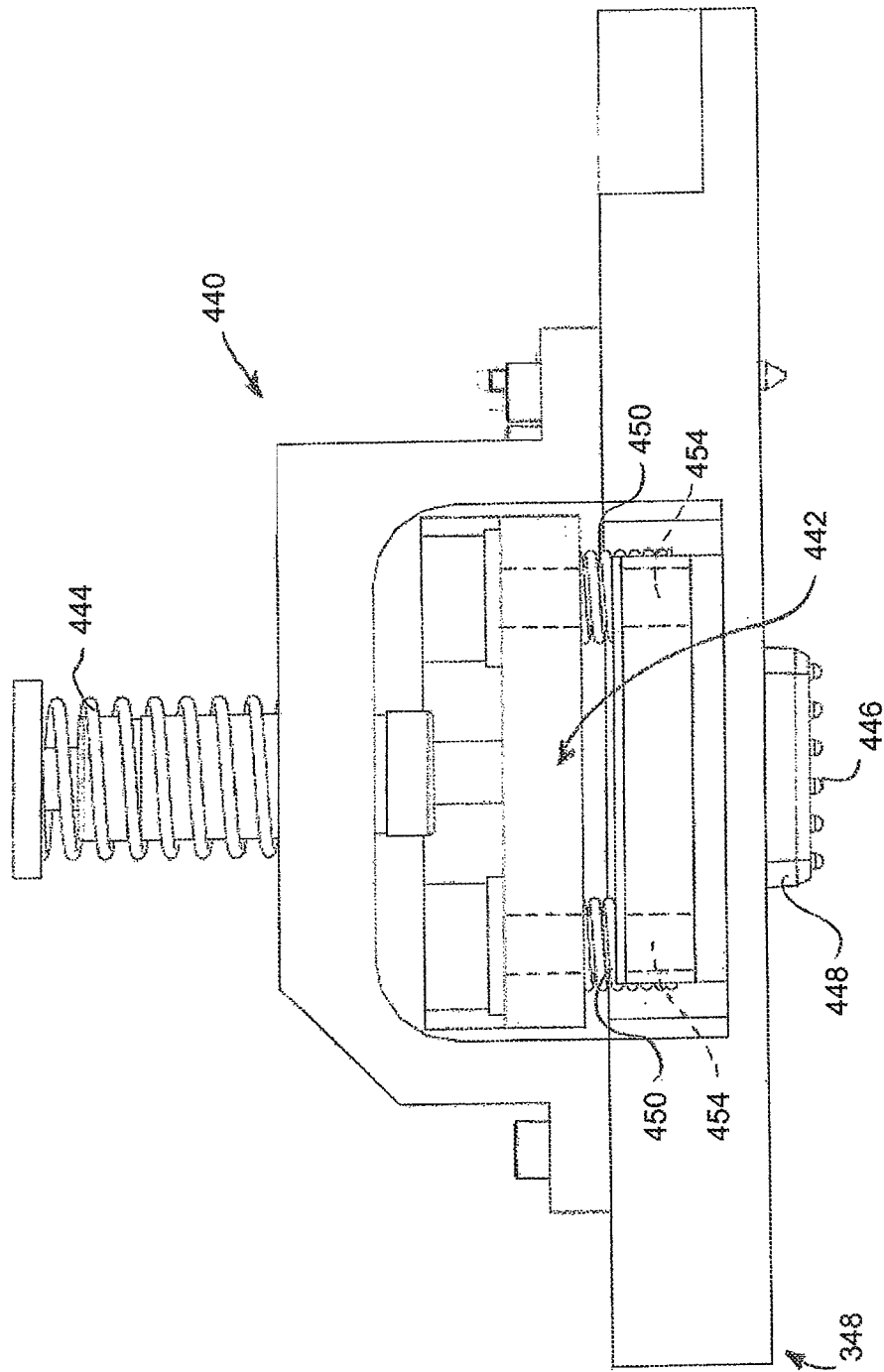
FIG. 32 is a side view of the upper receptacle enclosure with the radio-frequency power delivery apparatus.
Figure 33:
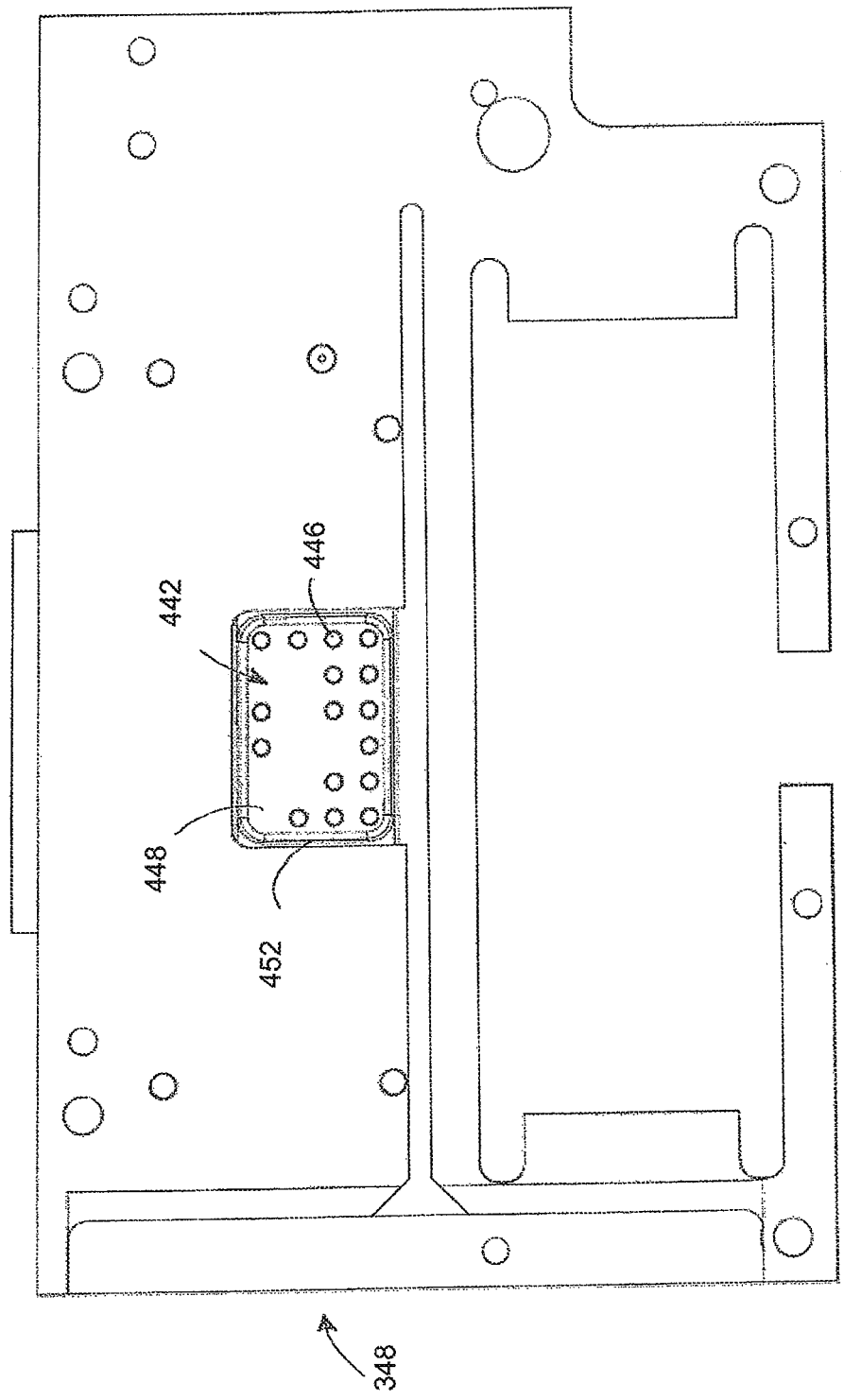
FIG. 33 is a bottom view of the upper receptacle enclosure with a radio-frequency power delivery apparatus.
Figure 34:
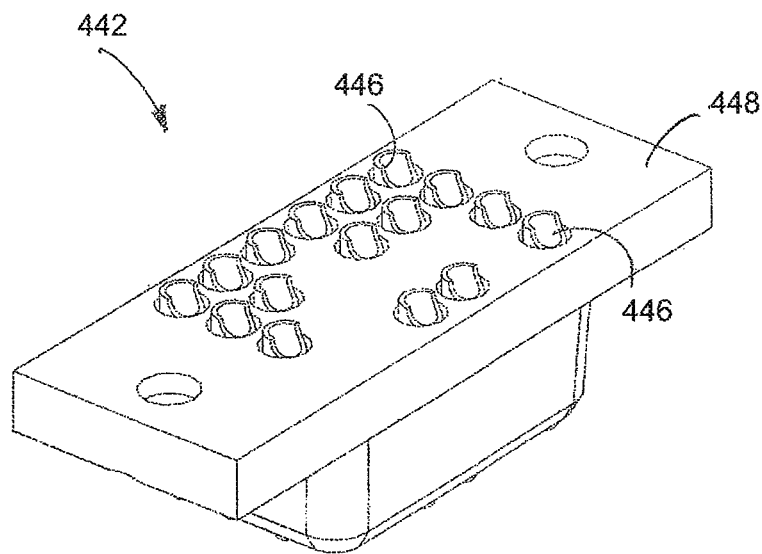
FIG. 34 is a perspective view of an electrical contact assembly for the radio-frequency power delivery apparatus comprising an electrical insulator/carrier and electrical contacts.
Figure 35:
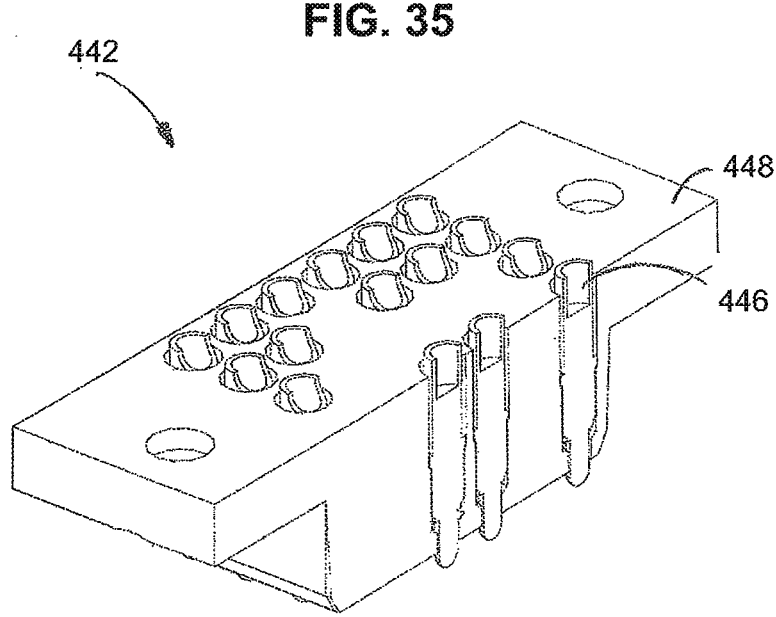
FIG. 35 is a cross sectional perspective view of the electrical contact assembly of FIG. 34.

As shown in FIG. 32 and FIG. 33, electrical contact assembly 442 extends through an aperture 452 in upper receptacle enclosure 348. As shown in FIG. 34 and FIG. 35, electrical contact assembly 442 comprises a plurality of electrical contacts 446 which extend through an electrical insulator/carrier 448.

Figure 36:
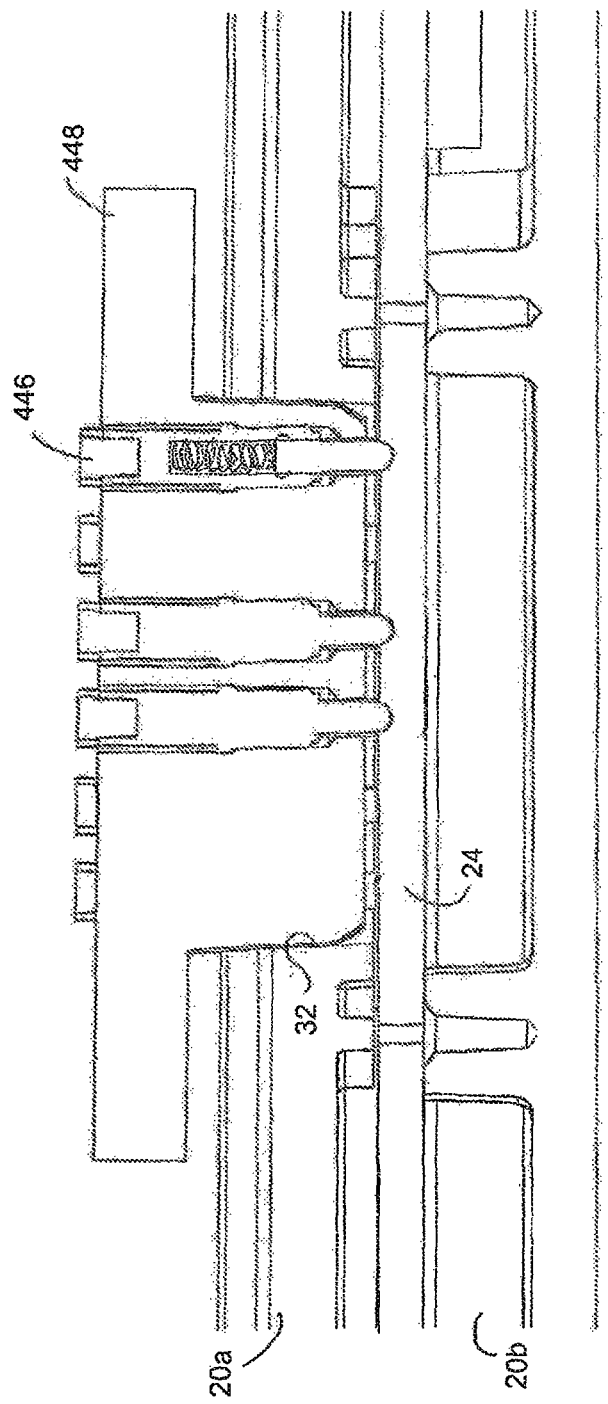
FIG. 36 is a cross sectional view of the electrical contact assembly and cartridge member.

As shown in FIG. 36, electrical contacts 446 are configured to mate and electrically communicate with the electrical contacts of printed circuit board 24, as well as the electric components and circuitry of electrosurgical unit 300 in a manner known in the art.

Electrical contacts 446 comprise a plurality of pogo (spring loaded) pins. As the pogo pins 446 make contact with printed circuit board 24, the pins 446 retract under load in a known manner until electrical insulator/contact carrier 448 may be positioned in contact with printed circuit board 24 and the pins 446 substantially retract into carrier 448. As shown in FIG. 36, an end portion of electrical contact carrier 448 may be configured to fit within aperture 32 of cartridge member 18.

Returning to FIG. 32, should electrical contact carrier 448 make contact with printed circuit board 24, radio-frequency power delivery apparatus 440 includes springs 450 which will compress upon reaching a load sufficient to overcome the bias/compression force of springs 450, with such force being lower than the force which may damage printed circuit board 24. In this manner, printed circuit board 24 may be protected from damage upon engagement with electrical contact assembly 442. Apparatus 440 also has the function of aligning contact carrier 448 to aperture 32 of cartridge member 18. In particular, the springs 450 and pins 454 (shown in phantom) are designed to allow the contact carrier 448 to float and align to the aperture 32 of cartridge member 18 as carrier 448 enters aperture 32, then return the contact carrier 448 to a straight position when retracted.

Having discussed electrosurgical unit 300 in detail, attention will now be directed to a system in which electro surgical device 10 and electro surgical unit 300 may be arranged and used, with FIG. 37 showing a view of one embodiment of a system of the present invention having exemplary electro surgical unit 300 in combination with a fluid source 500 and a handheld electro surgical device 10. FIG. 37 shows a movable cart 504 having a support member 506 comprising a hollow cylindrical post which carries a platform 508 comprising a pedestal table to provide a flat, stable surface for location of the electro surgical unit 300.

As shown, cart 504 further comprises a fluid source carrying pole 510 having a height which may be adjusted by sliding the carrying pole 510 up and down within the support member 506 and thereafter secured in position with a set screw. On the top of the fluid source carrying pole 510 is a cross support provided with loops at the ends thereof to provide a hook for carrying fluid source 500.

As shown in FIG. 37, fluid source 500 may comprise a bag of fluid from which the fluid 502 flows through drip chamber 48 after the bag is penetrated with a spike 50 located at the end of the drip chamber 48. In other embodiments, drip chamber 48 may be eliminated and tubing segment 46 may be attached directly to a spike 50. Thereafter, fluid 502 flows through flexible delivery tubing segment 46, cartridge member 18 and delivery tubing segment 106 of cable 42 to hand-piece 12 electro surgical device 10.

In the present embodiment the fluid 502 comprises saline solution, and even more specifically, normal (physiologic) saline. Although the description herein may make reference to saline as the fluid 502, other electrically conductive fluids can be used in accordance with the invention.

While an electrically conductive fluid having an electrically conductivity similar to normal saline is preferred, as will become more apparent with further reading of this specification, fluid 502 may also comprise an electrically non-conductive fluid. The use of a non-conductive fluid, while not providing all the advantage of an electrically conductive fluid, still provides certain advantages over the use of a dry electrode including, for example, reduced occurrence of tissue sticking to the electrodes 180a, 180b of device 10 and cooling of the electrodes and/or tissue. Therefore, it is also within the scope of the invention to include the use of a non-conducting fluid, such as, for example, deionized water.

As indicated above, electrosurgical unit 300 is configured to provide both monopolar and bipolar power output. However, electro surgical unit 300 preferably includes a lock out feature which prevents both monopolar and bipolar output from being activated simultaneously.

Figure 38:
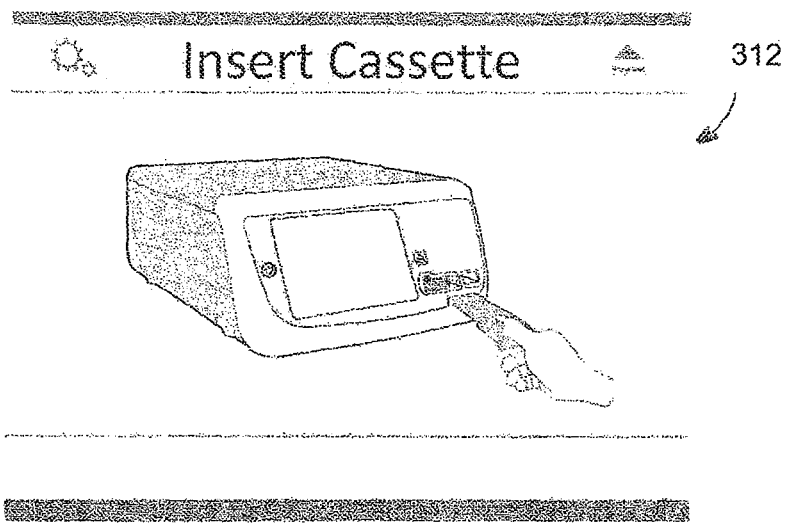
FIG. 38 is a display screen for the electro surgical unit requesting insertion of the cartridge member.

When the power switch 304 is turned on electro surgical unit 300, a number of touch control screens are presented to the user from the graphical user interface 306 to set up the use of device 10. As shown in FIG. 38, after performing an initial system check, a display 312 is presented to the user requesting insertion of cartridge member 18. Upon cartridge member 18 being placed in cartridge receptacle 310, controller 338 receives a signal of the presence thereof from a sensor. Controller 338 then initiates the movement of docking mechanism 410 from its non-use (unengaged) position to its use (engaged) position.

Upon reaching its use (engaged) position, controller 338 receives another signal to indicate such from another sensor. After receiving the signal, controller 338 now may access the memory 26 of cartridge member 18 for certain information stored thereon concerning device 10.

As indicated above, electro surgical unit 300 may be configured to receive and read a stream of serial data including certain process parameters and other information from device 10. Controller 338 may determine if memory 26 includes a unique identifier such as a serial number for device 10. If so, the controller 338 may read and store the serial number to its own memory. Controller 338 may also determine if a fixed time period (e.g. 24 hours) for use of device 10 is included in memory 26. If so, controller 338 may apply the time period to an internal countdown clock, which may begin counting the time period down after the first radio-frequency power activation of unit 300 with device 10 therein. Thereafter, once the time period has expired, controller 338 may be programmed to associate the serial number with an expired device 10 and no longer operate device 10. In this manner, use of device 10 with cartridge 18 may be limited as intended to a single use disposable to better assure patient safety.

Figure 39:
FIG. 39 is a display screen for the electro surgical unit requesting priming of the electrosurgical device with fluid.

As shown in FIG. 39, after electrosurgical unit 300 senses the insertion of cartridge member 18, a display 314 is presented to the user to confirm that that fluid source 500 has been spiked, and to initiate priming of electro surgical device 10 with fluid 502. Priming is desirable to inhibit radio-frequency power activation without the presence of fluid 502 in device 10.

Figure 40:
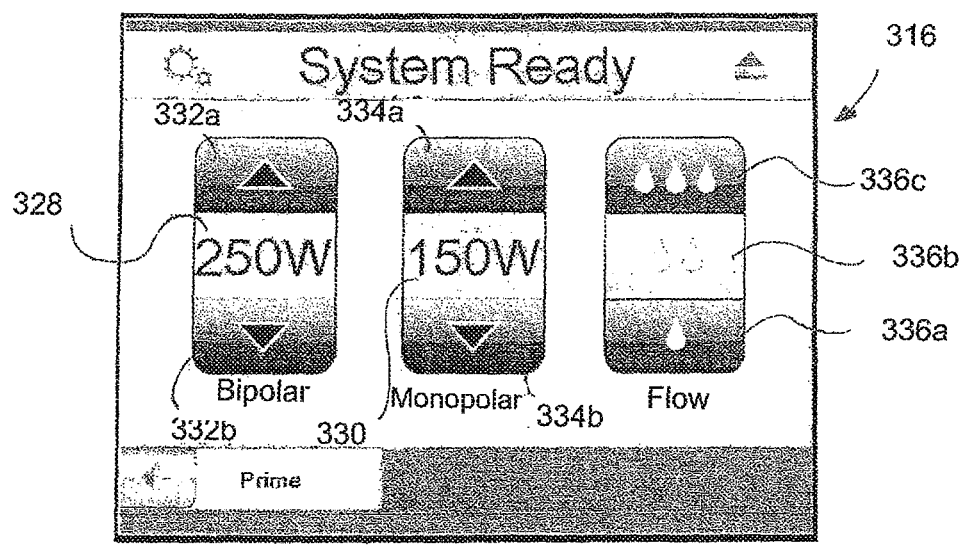
FIG. 40 is a display screen for the electrosurgical unit showing the electrosurgical unit and system is ready for operation.
Figure 41:
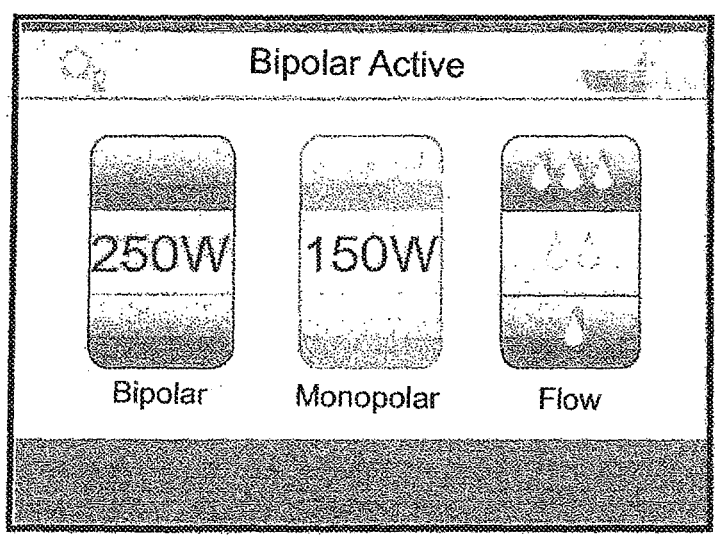
FIG. 41 is a display screen for the electro surgical unit showing radio-frequency power is being provided from the unit.

After priming is complete, as shown in FIG. 40, display 316 is presented to the user indicating that the system is now ready for use. Additionally, display 316 presents the user with a default radio-frequency power level settings 328 and 330 numerically in watts, which may be thereafter increased or decreased by touching radio-frequency power level selectors 332a, 334a and 332b, 334b, respectively. RF power output may be set in 1 watt increments in the range of 1 to 40 watts, 5 watt increments in the range of 40 to 100 watts and 10 watt increments in the range of 100 to 300 watts. When radio-frequency power is activated, the system ready portion of the display will change to visually indicate that radio-frequency power is active as shown in FIG. 41.

In addition to display 316 presenting a user with a default radio-frequency power level setting, display 316 also presents the user with a plurality of fluid flow settings 336a, 336b and 336c, which correspond to fluid flow settings of low (represented by one fluid droplet), medium (represented by two fluid droplets) and high (represented by three fluid droplets), respectively. The appropriate setting will illuminate when selected to visual indication of such to the user, with the medium (or intermediate) setting generally being the default setting.

Controller 338 of electro surgical unit 300 may also be programmed to obtain and read the default settings for radio-frequency power level and fluid flow level for device 10 which may be stored in memory 26 and thereafter set the unit 300 to these settings and present these default settings on display 316.

Controller 338 of electrosurgical unit 300 may be programmed to obtain and read a maximum power level for use of device 10 which is stored in memory 26. In this manner, electro surgical unit 300 would not activate its radio-frequency power for device 10 should the user wish to select a radio-frequency power level greater than the maximum power level allotted.

Controller 338 of electrosurgical unit 300 may also be programmed to obtain and read data from memory 26 which relates a speed of the pump assembly 422, and therefore the throughput of fluid 502 expelled by fluid delivery apparatus 420, to a particular radio-frequency power level as well as a particular fluid flow setting. In this manner, the fluid flow from device 10 for a particular radio-frequency power level and fluid level may be better controlled and a greater power level would not be available for selection.

Figure 42:
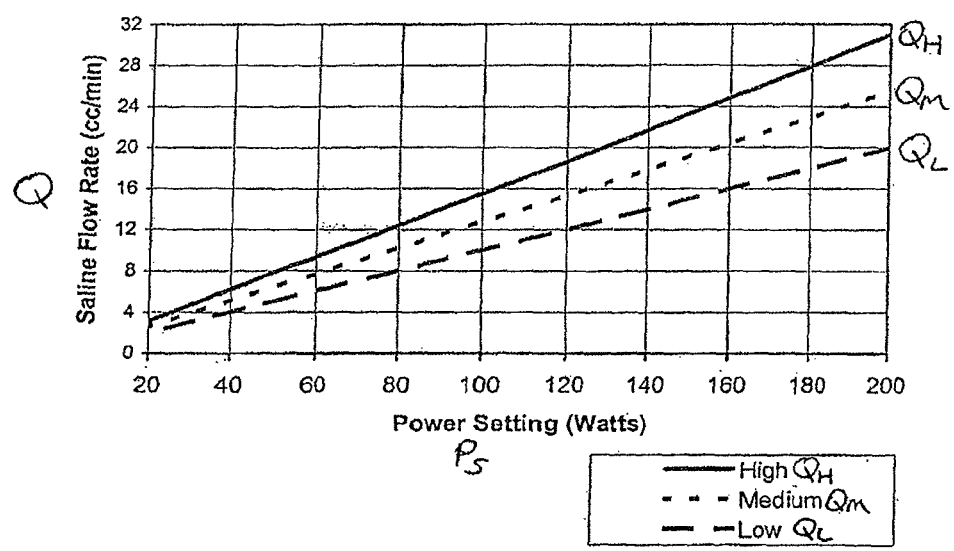
FIG. 42 is an exemplary graph showing a relationship of fluid flow rate Q in units of cubic centimeters per minute (cc/min) on the Y-axis, and the RF power setting $P_s$ in units of watts on the X-axis.

Exemplary functional relationships of fluid flow rate Q in units of cubic centimeters per minute (cc/min) on the Y-axis, and the bipolar RF power setting Ps in units of watts on the X-axis as shown in FIG. 42. The relationships may be engineered to inhibit undesirable effects such as tissue desiccation, electrode sticking, smoke production and char formation, while at the same time not providing a fluid flow rate Q at a corresponding RF power setting Ps which is so great as to provide too much electrical dispersion and cooling at the electrode/tissue interface. While not being bound to a particular theory, a more detailed discussion on how the fluid flow rate interacts with the radio frequency power, modes of heat transfer away from the tissue, fractional boiling of the fluid and various control strategies may be found in U.S. Publication No. 200110032002, published Oct. 18, 2001, assigned to the assignee of the present invention and hereby incorporated by reference in its entirety to the extent it is consistent.

As shown in FIG. 42, exemplary relationships QL, QM and QH are configured to increase the fluid flow rate Q linearly with an increasing radio-frequency power level setting Ps for each of three fluid flow rate settings of low, medium and high, respectively. Conversely, the relationships QL, QM and QH are configured to decrease the fluid flow rate Q linearly with a decrease RF power setting Ps for each of three fluid flow rate settings of low, medium and high, respectively. Accordingly, the data stored in the memory 26 of device 10 is to set a speed of the pump assembly 422 for a particular radio-frequency power level and a particular fluid flow level such that the throughput of fluid delivery apparatus 420 corresponds to the relationships provided in FIG. 42. The data may be stored in the form of equations, or as numerical data points as part of a database look-up table.

Figure 43:
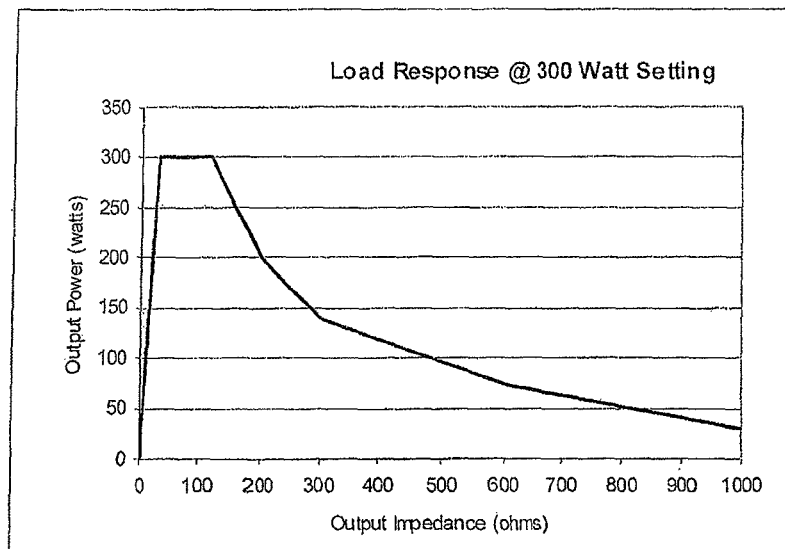
FIG. 43 is an exemplary graph of the bipolar RF power output versus impedance for the electrosurgical unit.

An exemplary bipolar radio-frequency power output curve of electrosurgical unit 300 is shown in FIG. 43. Impedance Z, shown in units of ohms on the X-axis and output power Po is shown in units of watts on the Y-axis. In the illustrated embodiment, the bipolar electrosurgical power (RF) is set to 300 watts. As shown in the figure, for an RF power setting Ps of 300 watts, the output power Po will remain constant with the set RF power Ps as long as the impedance Z stays between the low impedance cut-off of 30 ohms and the high impedance cut-off of 120 ohms. Below an impedance Z of 30 ohms, the output power Po will decrease as shown by the low impedance ramp. Above an impedance Z of 120 ohms, the output power Po will also decrease as shown by the high impedance ramp.

Figure 44:
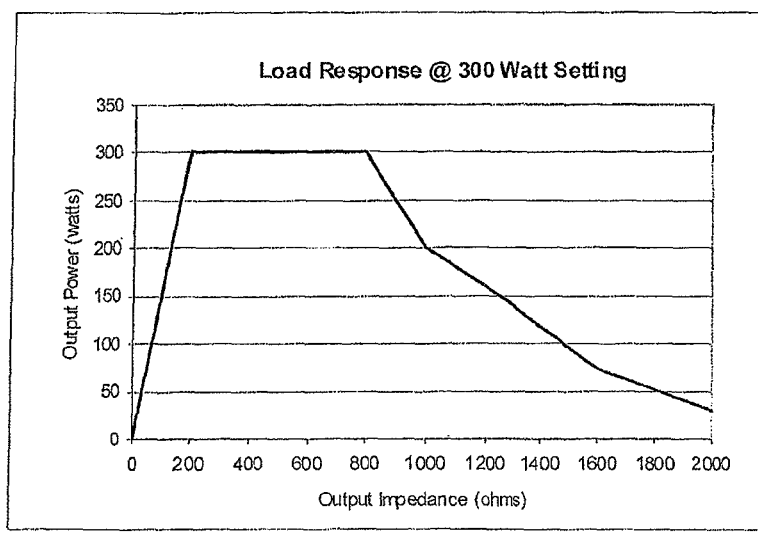
FIG. 44 is an exemplary graph of the bipolar RF power output versus impedance for the electrosurgical unit.

With respect to monopolar power output, an exemplary monopolar radio-frequency power output curve of electrosurgical unit 300 is shown in FIG. 44. Impedance Z, shown in units of ohms on the X-axis and output power Po is shown in units of watts on the Y-axis. In the illustrated embodiment, the bipolar electro surgical power (RF) is set to 300 watts. As shown in the figure, for an RF power setting Ps of 300 watts, the output power Po will remain constant with the set RF power Ps as long as the impedance Z stays between the low impedance cut-off of 200 ohms and the high impedance cut-off of 800 ohms. Below an impedance Z of 200 ohms, the output power Po will decrease as shown by the low impedance ramp.

Above an impedance Z of 800 ohms, the output power Po will also decrease as shown by the high impedance ramp.

Figure 45:
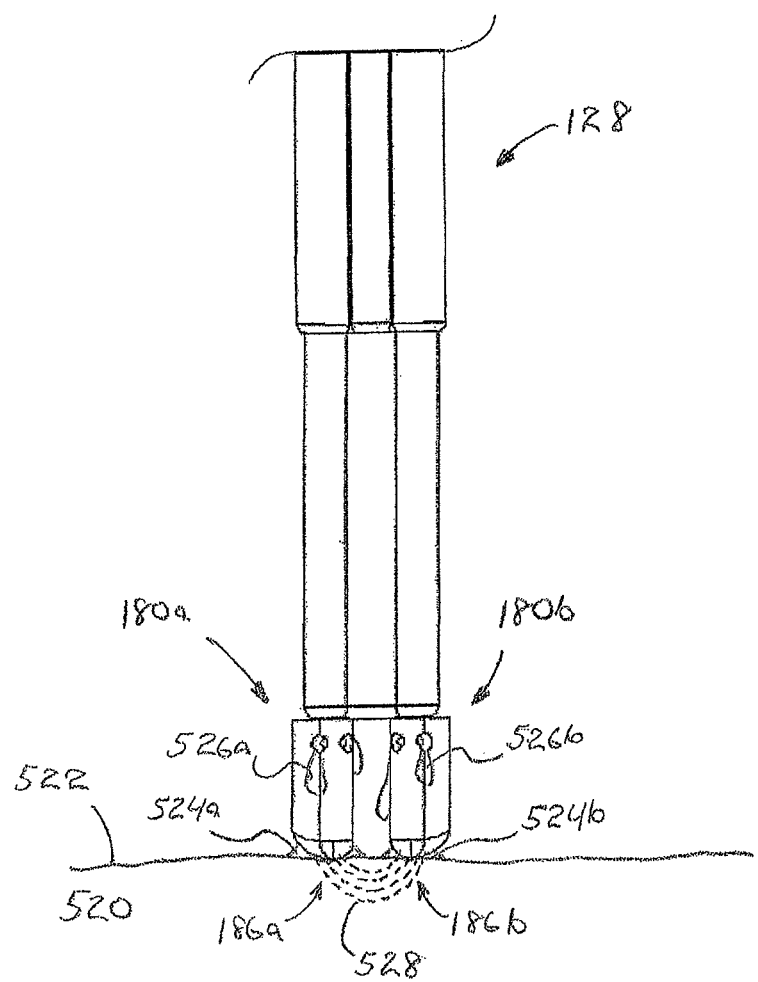
FIG. 45 is a close-up view of a distal end portion of the device of FIG. 1 with an exemplary fluid coupling to a tissue surface of tissue.

Having discussed a system in which electrosurgical device 10 and electrosurgical unit 300 may be arranged and used, attention will now focus on an application of electro surgical device 10 to treating tissue. As shown in FIG. 45, one way in which device 10 with hand-piece 12 may be used is with the longitudinal axis of electrodes 180a, 180b vertically orientated, and the distal end portion 186a, 186b of electrodes 180a, 180b laterally spaced adjacent tissue surface 522 of tissue 520. When device 10 is used in this manner, electrodes 180a, 180b are connected to electrosurgical unit 300 and receive bipolar radio frequency power which forms an alternating current electrical field 528 in tissue 520 located between electrodes 180a, 180b. In the presence of alternating current, the electrodes 180a, 180b alternate polarity between positive and negative charges with current flow from the positive to negative charge. Without being bound to a particular theory, heating of the tissue is performed by electrical resistance heating.

Fluid 502, in addition to providing an electrical coupling between the device 10 and tissue 520, lubricates surface 522 of tissue 520 and facilitates the movement of electrodes 180a, 180b across surface 522 of tissue 520. During movement of electrodes 180a, 180b, electrodes 180a, 180b typically slide across the surface 522 of tissue 520. Typically the user of device 10 slides electrodes 180a, 180b across surface 522 of tissue 520 back and forth with a painting motion while using fluid 502 as, among other things, a lubricating coating. The thickness of the fluid 502 between the distal end portions 186a, 186b of electrodes 180a, 180b and surface 522 of tissue 520 at the outer edge of couplings 524a, 524b may be in the range of and any increment between 0.05 mm to 1.5 mm. Also, in certain embodiments, the distal end portion 186a, 186b of electrodes 180a, 180b may contact surface 522 of tissue 520 without any fluid 502 in between.

As shown in FIG. 45, fluid 502 expelled from fluid outlets 208a/210a/212a/214a and 208b1210b/212b1214b may form into droplets 526a, 526b which flow distally on electrodes 180a, 180b. As shown in FIG. 45, droplets 526a, 526b may form at varying times from fluid 502 expelled from anyone of the fluid outlets. Also, fluid 502 may be expelled in varying quantity from each of the fluid outlets, depending on, for example, device orientation, pressure, flow rate and varying fluid outlet sizes. With use of device 10, the size of droplets 526a, 526b may also vary due to changes in the surface finish of the electrodes 180a, 180b, for example, as a result of being contaminated by blood and tissue.

Figure 46:
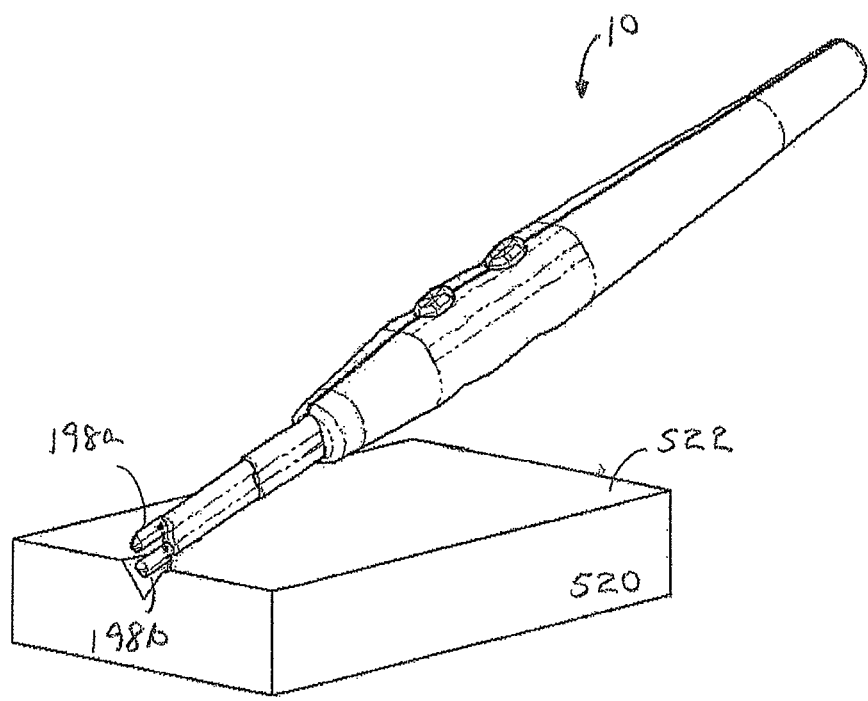
FIG. 46 is a perspective view of the device of FIG. 1 cutting tissue.

As shown in FIG. 45, fluid couplings 524a, 524b comprise discrete, localized webs and more specifically comprise triangular shaped webs or bead portions providing a film of fluid 502 between surface 522 of tissue 520 and electrodes 180a, 180b. When the user of electrosurgical device 10 places electrodes 180a, 180b at a tissue treatment site and moves electrodes 180a, 180b across the surface 522 of the tissue 520, fluid 502 is expelled from fluid outlets 208a/210a/212a/214a and 208b1210b/212b1214b around the surfaces of electrodes 180a, 180b and onto the surface 522 of the tissue 520 via couplings 524a, 524b. At the same time, radio-frequency electrical energy, shown by electrical field lines 528, is provided to tissue 520 at tissue surface 522 and below tissue surface 522 into tissue 520 through fluid couplings 524a, 524b. As shown in FIG. 46, hand-piece 12 of device 10 may be used to cut tissue by applying either cutting edge 198a or 198b to tissue 520, depending which electrode 180a, 180b is utilized.

With regards to hand-piece 12a, as shown in FIG. 47, when the user of electro surgical device 10 places electrodes 180a, 180b at a tissue treatment site and moves electrodes 180a, 180b across the surface 522 of the tissue 520, fluid 502 is expelled from fluid outlets 240a and 240b onto surfaces 222a, 222b of electrodes 180a, 180b and onto the surface 522 of the tissue 520 via couplings 524a, 524b. At the same time, radio-frequency electrical energy, shown by electrical field lines 528, is provided to tissue 520 at tissue surface 522 and below tissue surface 522 into tissue 520 through fluid couplings 524a, 524b. In this manner, device 10 may be used to seal and/or shrink blood vessels in tissue 520 to inhibit blood loss therefrom. Similar to FIG. 46, hand-piece 12a of device 10 may be used to cut tissue by applying either cutting edge 226a or 226b to tissue 520, depending which electrode 180a, 180b is utilized.

Device 10 may be used to perform a solid organ resection such as a liver resection. Edge 198a or 198b may be first used to score the outer capsule of the liver along the planned line of resection. Thereafter, the distal end portions 186a, 186b of electrodes 180a, 180b may be moved back and forth along the line, with radio frequency power and the flow of fluid on, resulting in coagulation of the liver parenchyma beneath the scored capsule. As the tissue is coagulated under and around the electrode surfaces, the electrodes 180a, 180b may be used to separate and blunt dissect the coagulated parenchyma and enter the resulting crevice. As the distal end portions 186a, 186b of electrodes 180a, 180b treat the parenchyma, the treated parenchyma looses integrity and becomes easier to separate, either alone or in conjunction with separation force applied by electrodes 180a, 180b from the user of the device.

Blunt dissection of the coagulated parenchyma IS performed by continuous abrading or splitting apart of the parenchyma with substantially the same back and forth motion as coagulation and with the device 10 being held substantially in the same orientation as for coagulation of the liver parenchyma. However, with blunt dissection, the surgeon typically applies more force to the tissue. In various embodiments, once the liver parenchyma is coagulated, blunt dissection may be performed with or without monopolar radio frequency power (i.e., on or off) and/or with or without the presence of fluid from device 10. Additionally or alternatively, the tissue on opposing sides of the line of resection may be placed into tension perpendicular to the line of resection to facilitate resection. Furthermore, resection may also be accomplished by sharp dissection with edge 198a or 198b of electrodes 180a, 180b. Thus, with device 10, a surgeon may perform a resection procedure in a number of different ways.

As the parenchyma is resected, blood vessels within the parenchyma may be uncovered which extend across or transverse the line of resection. Device 10 may be used to shrink and seal these vessels by heating and shrinking the collagen contained in the walls of the vessels thus decreasing the diameter of the lumen of these vessels. For vessels with a diameter too large to completely occlude the lumen, the vessels may tied with suture on each side of the line of resection and thereafter severed therebetween. If such vessels are not first uncovered by removing the surrounding parenchyma tissue and without being severed, they may bleed profusely and require much more time to stop the bleeding. Consequently, it may be desirable to avoid separation by sharp dissection in situations where large vessels are not first uncovered and exposed.

This technique can also be used on other parenchymal organs such as the pancreas, the kidney, and the lung. In addition, it may also be useful on muscle tissue and subcutaneous fat. Its use can also extend to tumors, cysts or other tissue masses found in the urological or gynecological areas. It would also enable the removal of highly vascularized tumors such as hemangiomas.

The devices disclosed herein are particularly useful as non-coaptive devices that provide cutting of tissue, as well as coagulation, hemostasis and sealing of tissue to inhibit blood and other fluid loss during surgery. In other words, grasping of the tissue is not necessary to shrink, coagulate, cut and seal tissue against blood loss, for example, by shrinking collagen and associated lumens of blood vessels (e.g., arteries, veins) to provided the desired hemostasis of the tissue. Furthermore, the control system of the electro surgical unit 300 is not necessarily dependent on tissue feedback such as temperature or impedance to operate. Thus, the control system of electrosurgical unit 300 may be open loop with respect to the tissue which simplifies use.

Device 10 disclosed herein are particularly useful to surgeons to achieve hemostasis after cutting through soft tissue, as part of hip or knee arthroplasty. The distal end portions 186a, 186b can be painted over the raw, oozing surface 522 of tissue 520 to seal the tissue 520 against bleeding, or focused on individual larger bleeding vessels to stop vessel bleeding. As part of the same or different procedure, device 10 is also useful to stop bleeding from the surface of cut bone, or osseous, tissue as part of any orthopaedic procedure that requires bone to be cut.

As is well known, bone, or osseous tissue, is a particular form of dense connective tissue consisting of bone cells (osteocytes) embedded in a matrix of calcified intercellular substance. Bone matrix mainly contains collagen fibers and the minerals calcium carbonate, calcium phosphate and hydroxyapatite. Among the many types of bone within the human body are compact bone and cancellous bone. Compact bone is hard, dense bone that forms the surface layers of bones and also the shafts of long bones. It is primarily made of haversian systems which are covered by the periosteum. Compact bone contains discrete nutrient canals through which blood vessels gain access to the haversian systems and the marrow cavity of long bones. For example, Volkmann's canals which are small canals found in compact bone through which blood vessels pass from the periosteum and connect with the blood vessels of haversian canals or the marrow cavity. Devices 30a-30e disclosed herein may be particularly useful to treat compact bone and to provide hemostasis and seal bleeding vessels (e.g. by shrinking to complete close) and other structures associated with Volkmann's canals and Haversian systems.

In contrast to compact bone, cancellous bone is spongy bone and forms the bulk of the short, flat, and irregular bones and the ends of long bones. The network of osseous tissue that makes up the cancellous bone structure comprises many small trabeculae, partially enclosing many intercommunicating spaces filled with bone marrow. Consequently, due to their trabecular structure, cancellous bones are more amorphous than compact bones, and have many more channels with various blood cell precursors mixed with capillaries, venules and arterioles. Device 10 disclosed herein may be particularly useful to treat cancellous bone and to provide hemostasis and seal bleeding structures such as the above micro-vessels (i.e. capillaries, venulesand arterioles) in addition to veins and arteries. Device 10 may be particularly useful for use during orthopedic knee, hip, shoulder and spine procedures (e.g. arthroplasty).

During a knee replacement procedure, the condyle at the distal epiphysis of the femur and the tibial plateau at the proximal epiphysis of the tibia are often cut and made more planer with saw devices to ultimately provide a more suitable support structure for the femoral condylar prosthesis and tibial prosthesis attached thereto, respectively. The cutting of these long bones results in bleeding from the cancellous bone at each location. In order to seal and arrest the bleeding from the cancellous bone which has been exposed with the cutting of epiphysis of each long bone, bipolar device 10 may be utilized. Thereafter, the respective prostheses may be attached.

Turning to a hip replacement procedure, the head and neck of the femur at the proximal epiphysis of the femur may be removed, typically by cutting with a saw device, and the intertrochantic region of the femur may be made more planer to provide a more suitable support structure for the femoral stem prosthesis subsequently attached thereto. With respect to the hip, a ball reamer may be used to ream and enlarge the acetabulum of the innominate (hip) bone to accommodate the insertion of an acetabular cup prosthesis therein, which will provide the socket into which the head of the femoral stem prosthesis fits. The cutting of the femur and reaming of the hip bone typically results in bleeding from the cancellous bone at each location. In order to seal and arrest the bleeding from the cancellous bone which has been cut and exposed, device 10 may be utilized. Thereafter, as with the knee replacement, the respective prostheses may be attached.

Device 10 may be utilized for treatment of connective tissues, such as for shrinking intervertebral discs during spine surgery. Intervertebral discs are flexible pads of fibrocartilaginous tissue tightly fixed between the vertebrae of the spine. The discs comprise a flat, circular capsule roughly an inch in diameter and about 0.25 inch thick, made of a tough, fibrous outer membrane called the annulus fibrosus, surrounding an elastic core called the nucleus pulposus.

Under stress, it is possible for the nucleus pulposus to swell and herniate, pushing through a weak spot in the annulus fibrosus membrane of the disc and into the spinal canal. Consequently, all or part of the nucleus pulposus material may protrude through the weak spot, causing pressure against surrounding nerves which results in pain and immobility.

Device 10 may be utilized to shrink protruding and herniated intervertebral discs which, upon shrinking towards normal size, reduces the pressure on the surrounding nerves and relieves the pain and immobility. Device 10 may be applied via posterior spinal access under surgeon control for focal shrinking of the annulus fibrosus membrane.

Where an intervertebral disc cannot be repaired and must be removed as part of a discectomy, device 10 may be particularly useful to seal and arrest bleeding from the cancellous bone of opposing upper and lower vertebra surfaces (e.g. the cephalad surface of the vertebral body of a superior vertebra and the caudad surface of an inferior vertebra). Where the disc is removed from the front of the patient, for example, as part of an anterior, thoracic spine procedure, device 10 may also be particularly useful to seal and arrest bleeding from segmental vessels over the vertebral body.

Device 10 may be utilized to seal and arrest bleeding of epidural veins which bleed as a result of the removal of tissue around the dural membrane during, for example a laminectomy or other neurosurgical surgery. The epidural veins may start bleeding when the dura is retracted off of them as part of a decompression. Also during a laminectomy, device 10 may be used to seal and arrest bleeding from the vertebral arch and, in particular the lamina of the vertebral arch.

As established above, device 10 of the present invention may inhibit such undesirable effects of tissue desiccation, electrode sticking, char formation and smoke generation. The use of the disclosed devices can result in significantly lower blood loss during surgical procedures. Such a reduction in blood loss can reduce or eliminate the need for blood transfusions, and thus the cost and negative clinical consequences associated with blood transfusions, such as prolonged hospitalization.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner(s) in which the invention may be claimed, or that all recited features are necessary.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner(s) in which the invention may be claimed, or that all recited features are necessary.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner(s) in which the invention may be claimed, or that all recited features are necessary.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

What is claimed is:

1. An electrosurgical device, the device comprising:
a first electrode and a second electrode, each electrode to receive radio frequency power from first and second wire conductors, respectively; and
a switch having a first position connected to the first electrode to activate monopolar power to the first electrode of the device from a radio-frequency generator to be coupled to the device and to disconnect the second electrode from the second wire conductor.

2. The device of claim 1 wherein:
the switch has a second position disconnected from the first electrode to deactivate the monopolar power to the first electrode of the device from a radio-frequency generator to be coupled to the device and to connect the second electrode to the second wire conductor.

3. The device of claim 2 wherein:
the switch forms a first closed circuit comprising the first electrode in the first position and a second closed circuit comprising the second electrode in the second position.

4. The device of claim 1 wherein:
the switch forms a first control circuit in the first position to provide a control signal from the device via a third conductor, the control signal causing the radio-frequency generator to activate monopolar power to the first electrode.

5. The device of claim 1 wherein:
the switch is activated by a push button.

6. An electrosurgical device, the device comprising:
a first electrode configured to receive radio frequency power from a first conductor;
a second electrode configured to receive radio frequency power from a second conductor; and
a switch having a first position connected to the first electrode to activate monopolar power to the first electrode from a radio-frequency generator to be coupled to the device, the switch being configured to inhibit capacitive coupling of the second electrode to the monopolar power by disconnecting the second electrode from the second conductor in the first position.

7. The device of claim 6 wherein:
the switch has a second position disconnected from the first electrode to deactivate the monopolar power to the first electrode from the radio-frequency generator, the second position connecting the second electrode with a bipolar power output of the radio-frequency generator.

8. The device of claim 7 wherein:
the switch forms a first closed circuit in the first position and a second closed circuit in the second position.

9. The device of claim 8 wherein:
the first closed circuit comprises the first electrode; and the second closed circuit comprises the second electrode.

10. The device of claim 6 wherein:
the switch comprises a bias spring, the bias spring configured to place the switch in the first position when compressed and the second position when decompressed.

11. The device of claim 6 wherein:
the switch comprises a bias spring, the bias spring configured to place the switch in the second position when compressed and the first position when decompressed.

12. The device of claim 6 wherein:
the switch forms a first control circuit in the first position to provide a control signal from the device via a third conductor, the control signal causing the radio-frequency generator to activate monopolar power to the first electrode.

13. The device of claim 6 wherein:
the switch is activated by a push button.

14. An electrosurgical device, the device comprising:
a first electrode and a second electrode;
a switch to activate and deactivate bipolar power to the first and second electrodes from a radio-frequency generator to be coupled to the device, the switch comprising a double pole, single throw switch; and
a switch to activate and deactivate monopolar power to the first electrode from the radio-frequency generator to be coupled to the device, the switch comprising a single pole, single throw switch.

15. The device of claim 14 wherein:
the double pole, single throw switch forms a control circuit with the radio-frequency generator to be coupled to the device;
the control circuit controls activation of the bipolar power from the radio-frequency generator when the double pole, single throw switch is in a closed position; and
the control circuit controls deactivation of the bipolar power from the radio-frequency generator when the double pole, single throw switch is in an open position.

16. The device of claim 15, wherein the double pole, single throw switch in the closed position enables a control signal to return from the device to the radio-frequency generator via the control circuit to activate the bipolar power.

17. The device of claim 16, wherein the double pole, single throw switch in the open position prevents the control signal from returning from the device to the radio-frequency generator via the control circuit, thereby deactivating the bipolar power from the radio-frequency generator.

18. The device of claim 16, wherein the control circuit comprises a conductor via which the control signal returns from the device to the radio-frequency generator, and wherein the conductor is distinct from conductors that provide bipolar power to the first and second electrodes.

19. The device of claim 14 wherein:
the double pole, single throw switch is in series between the second electrode and a bipolar power output of the radio-frequency generator to be coupled to the device.

20. The device of claim 14 wherein:
the double pole, single throw switch connects the second electrode with a bipolar power output of the radio-frequency generator in a closed position and disconnects the second electrode with the bipolar power output of the radio-frequency generator in an open position.

21. The device of claim 14 wherein:
the single pole, single throw switch forms a control circuit with the radio-frequency generator to be coupled to the device;
the control circuit controls activation of the monopolar power from the radio-frequency generator when the single pole, single throw switch is in a closed position; and
the control circuit controls deactivation of the monopolar power from the radio-frequency generator when the single pole, single throw switch is in an open position.

22. The device of claim 21, wherein the single pole, single throw switch in the closed position enables a control signal to return from the device to the radio-frequency generator via the control circuit to activate the monopolar power from the radio-frequency generator.

23. The device of claim 22, wherein the single pole, single throw switch in the open position prevents the control signal from returning from the device to the radio-frequency generator via the control circuit, thereby deactivating the monopolar power from the radio-frequency generator.

24. The device of claim 22, wherein the control circuit comprises a conductor via which the control signal returns from the device to the radio-frequency generator, and wherein the conductor is distinct from a conductor that provides monopolar power to the first electrode.

25. The device of claim 14 wherein:
the switch to activate and deactivate bipolar power and the switch to activate and deactivate monopolar power are both located on a hand-piece of the device.

26. The device of claim 14 wherein:
at least one of the double pole, single throw switch or the single pole, single throw switch is activated and deactivated by a push button.

27. An electrosurgical device, the device comprising:
a first electrode configured to receive radio frequency power from a first conductor;
a second electrode configured to receive radio frequency power from a second conductor;
a first switch to activate and deactivate monopolar power to the first electrode of the device from a radio-frequency generator to be coupled to the device; and
a second switch to activate and deactivate bipolar power to the first and second electrodes from the radio-frequency generator to be coupled to the device, the second switch configured to inhibit capacitive coupling of the second electrode to the monopolar power by disconnecting the second electrode from the second conductor.

28. The device of claim 27 wherein:
the first switch comprises a single pole, single throw switch; and
the second switch comprises a double pole, single throw switch.

29. The device of claim 28 wherein:
at least one of the first switch or the second switch is activated and deactivated by a push button.

30. The device of claim 27 wherein:
the first switch forms a first control circuit with the radio-frequency generator to be coupled to the device;
the first control circuit controls activation of the monopolar power from the radio-frequency generator when the switch is in a closed position; and
the first control circuit controls deactivation of the monopolar power from the radio-frequency generator when the switch is in an open position.

31. The device of claim 30, wherein the first switch in the closed position enables a control signal to return from the device to the radio-frequency generator via the first control circuit to activate the monopolar power from the radio-frequency generator.

32. The device of claim 31, wherein the first switch in the open position prevents the control signal from returning from the device to the radio-frequency generator via the control circuit, thereby deactivating the monopolar power from the radio-frequency generator.

33. The device of claim 31, wherein the first control circuit comprises a conductor via which the control signal returns from the device to the radio-frequency generator, and wherein the conductor is distinct from a conductor that provides monopolar power to the first electrode.

34. The device of claim 27 wherein:
the second switch forms a second control circuit with the radio-frequency generator to be coupled to the device;
the second control circuit controls activation of bipolar power from the radio-frequency generator when the switch is in a closed position; and
the second control circuit controls deactivation of the bipolar power from the radio-frequency generator when the switch is in an open position.

35. The device of claim 34, wherein the second switch in the closed position enables a control signal to return from the device to the radio-frequency generator via the second control circuit to activate the bipolar power from the radio-frequency generator.

36. The device of claim 35, wherein the second switch in the open position prevents the control signal from returning from the device to the radio-frequency generator via the second control circuit, thereby deactivating the bipolar power from the radio-frequency generator.

37. The device of claim 35, wherein the control circuit comprises a conductor via which the control signal returns from the device to the radio-frequency generator, and wherein the conductor is distinct from conductors that provide bipolar power to the first and second electrodes.

38. The device of claim 27 wherein:
the second switch is in series between the second electrode and a bipolar power output of the radio-frequency generator to be coupled to the device.

39. The device of claim 27 wherein:
the second switch connects the second electrode with a bipolar power output of the radio-frequency generator in a closed position and disconnects the second electrode with the bipolar power output of the radio-frequency generator in an open position.

40. The device of claim 27 wherein:
the first switch and the second switch are both located on a hand-piece of the device.

\* \* \* \* \*